(12) United States Patent
Xu

(10) Patent No.: US 6,991,813 B2
(45) Date of Patent: Jan. 31, 2006

(54) PHYSIOLOGICAL TISSUE REPAIR AND FUNCTIONAL ORGAN REGENERATION BY CULTIVATION OF REGENERATIVE STEM CELLS IN VIVO AND IN SITU

(75) Inventor: Rongxiang Xu, 505 Los Altos Ave., Arcadia, CA (US) 91007

(73) Assignee: Rongxiang Xu, Arcadia, CA (US)

( * ) Notice: Subject to any disclaimer, the term of this patent is extended or adjusted under 35 U.S.C. 154(b) by 357 days.

(21) Appl. No.: 10/187,268

(22) Filed: Jun. 28, 2002

(65) Prior Publication Data

US 2003/0021850 A1 Jan. 30, 2003

Related U.S. Application Data

(60) Provisional application No. 60/301,961, filed on Jun. 28, 2001.

(51) Int. Cl.
*A61K 35/78* (2006.01)
(52) U.S. Cl. ............... 424/725; 424/520; 424/400; 424/537; 424/539
(58) Field of Classification Search ........... 424/725, 424/520, 400, 537, 539
See application file for complete search history.

(56) References Cited

U.S. PATENT DOCUMENTS

| 4,016,273 A | * | 4/1977 | Sieger et al. | ......... 514/211.13 |
| 5,405,608 A | * | 4/1995 | Xu | ............. 424/520 |
| 5,817,322 A | * | 10/1998 | Xu | ............. 424/401 |
| 6,685,971 B2 | * | 2/2004 | Xu | ............. 424/725 |

OTHER PUBLICATIONS

Debridement, Dr. Joseph F. Smith Medical Library, http://www.chclibrary.org/micromed/00044870.html.*
Huang qin, DrugDigest, http://www.drugdigest.org/DD/DVH/HerbsWho/0,3923,552023|Huang+Qin,00.html.*
Codex Standard for Named Vegetable Oils, CX-STAND 210-1999, Codex Alimentarius, vol. 8: 11-25, 2001.*

* cited by examiner

*Primary Examiner*—Jean C. Witz
(74) *Attorney, Agent, or Firm*—Shirley Chen; Wilson Sonsini Goodrich & Rosati

(57) ABSTRACT

The present invention provides novel compositions and methods for pharmaceutical or nutraceutical use in an animal, preferably in a human. In one aspect, compositions and methods are provided for promoting cell growth, tissue repair and organ regeneration, preferably in vivo and in situ. The composition comprises a sterol compound dissolved in oil at a concentration at least 0.5% by weight. The compositions may be used in the treatment of various conditions caused by injury, diseases and aging. As shown clinically, the methodology disclosed in the present invention was used successfully to regenerate or clone a new organ through cultivation of regenerative stem cells in vivo and in situ.

37 Claims, 55 Drawing Sheets

Tissue Repair and Organ Regeneration by Cultivation of Stem Cells in vivo and in situ

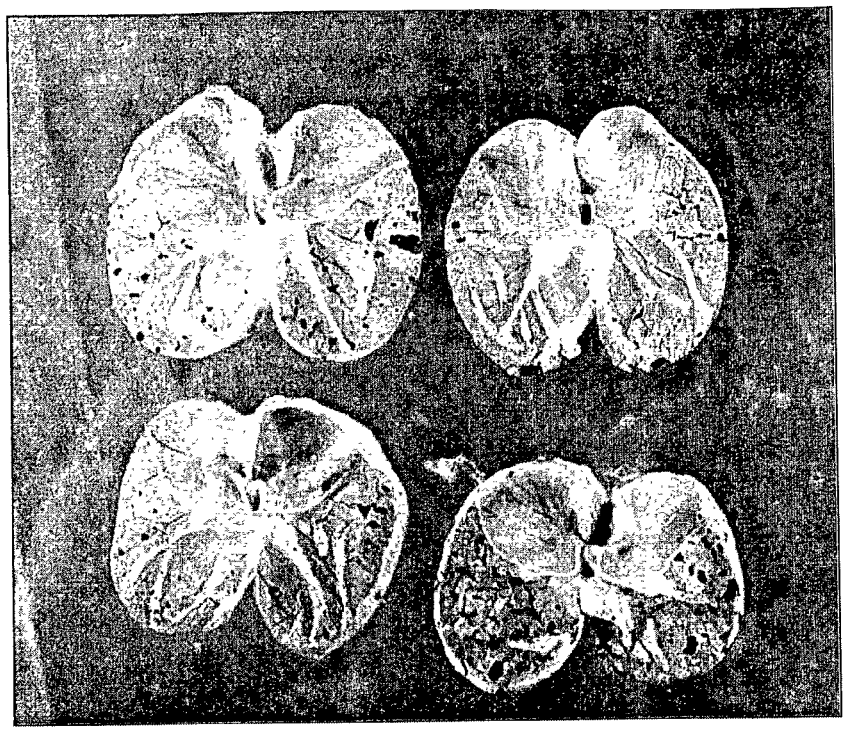
Figure 3-A
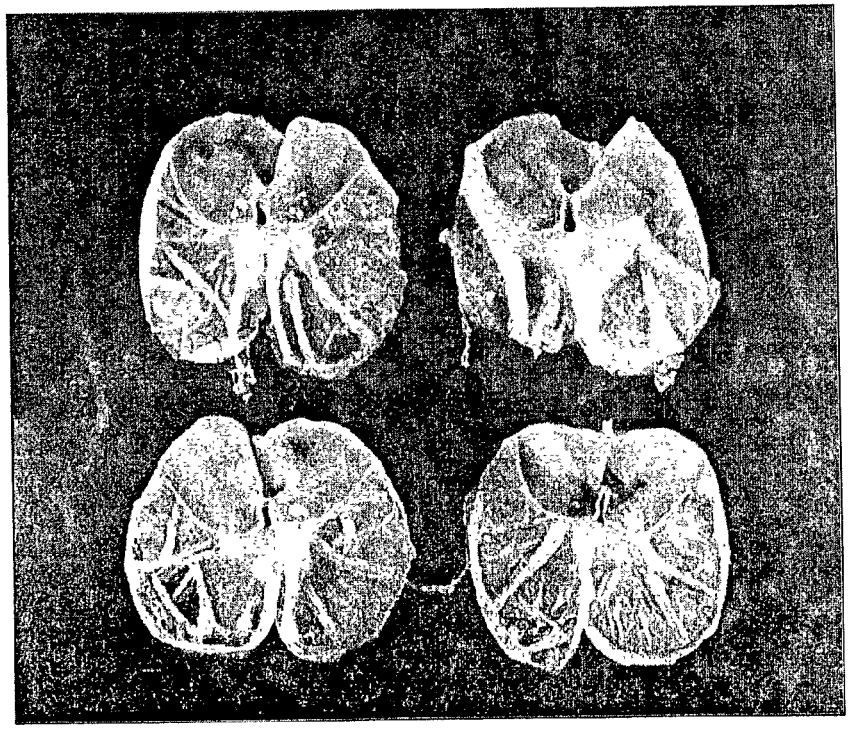
Figure 3-B

Figure 4-A
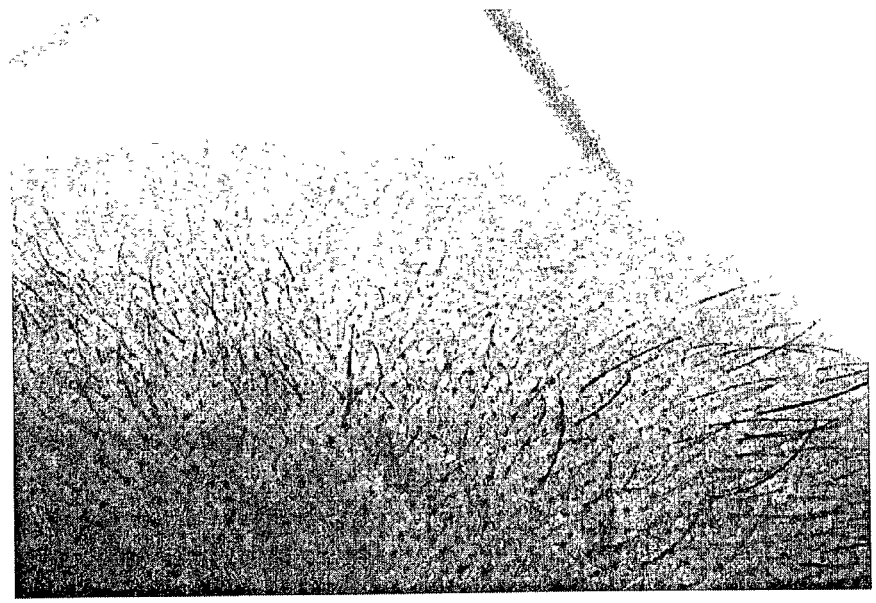
Figure 4-B
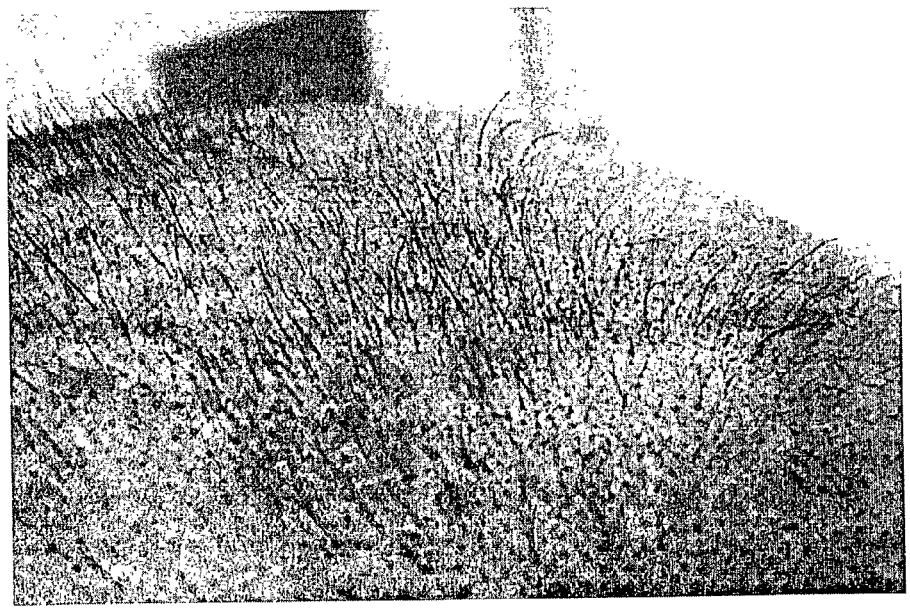

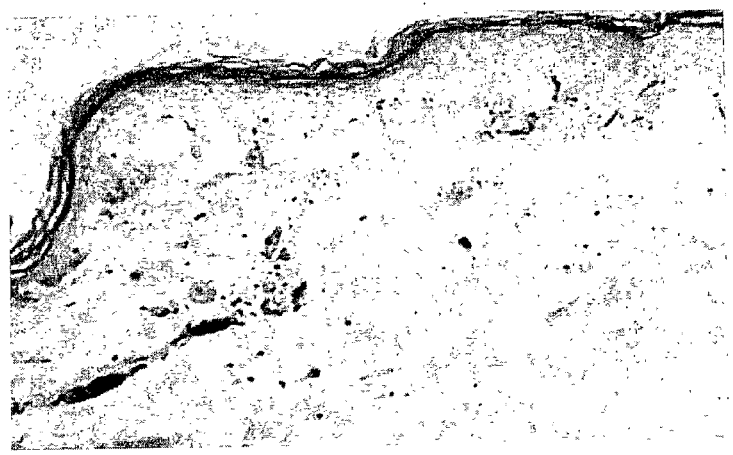
Figure 5-A
Figure 5-B
Figure 5-C

Figure 10-A
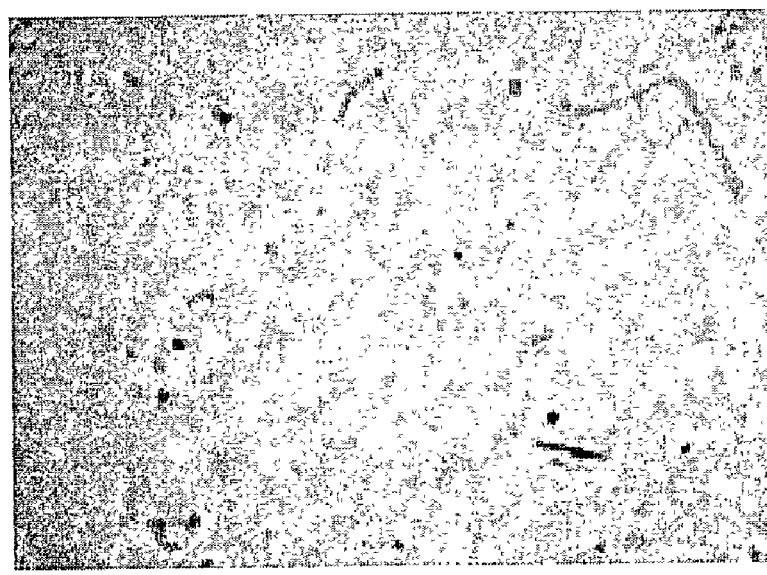
Figure 10-B

TREATMENT        CONTROL
Figure 15-A 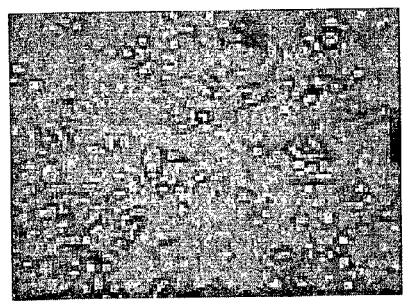 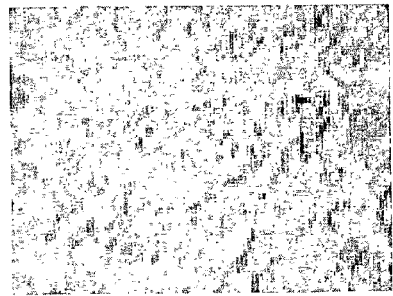
Figure 15-B 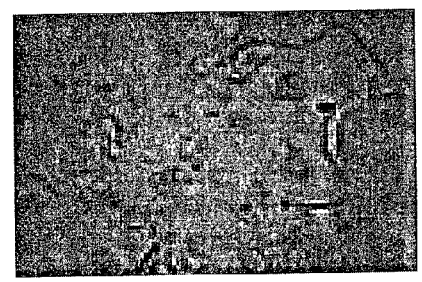 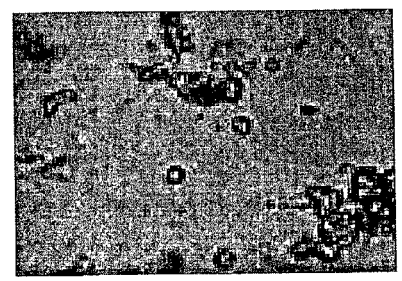
Figure 15-C 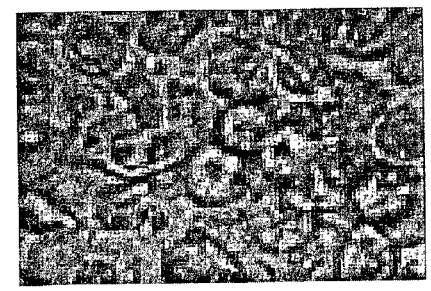 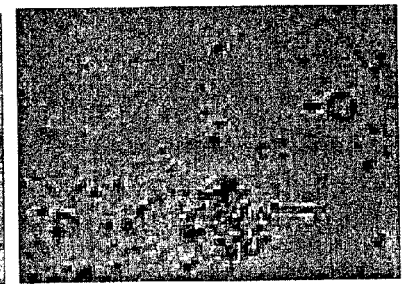
Figure 15-D 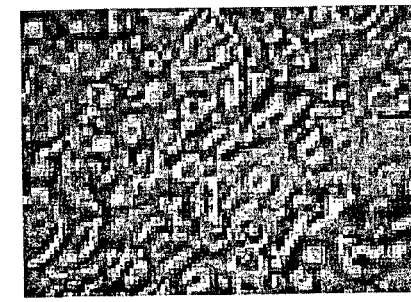 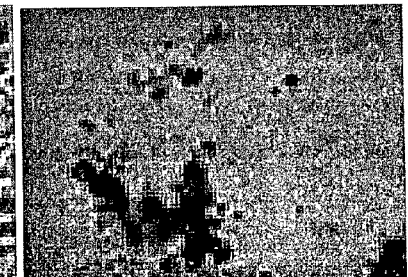

TREATMENT CONTROL
Figure 16-A
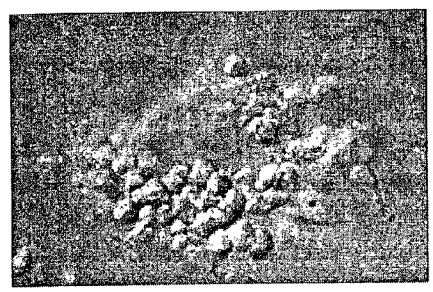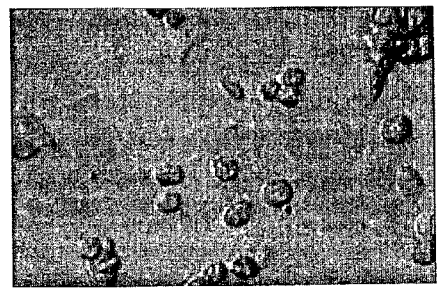
Figure 16-B
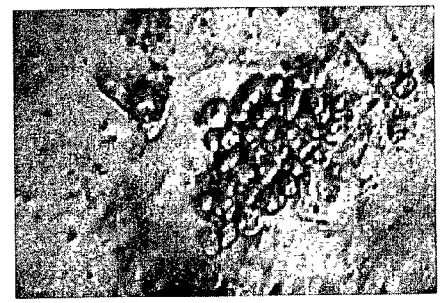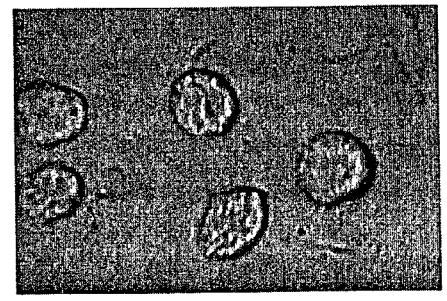
Figure 16-C
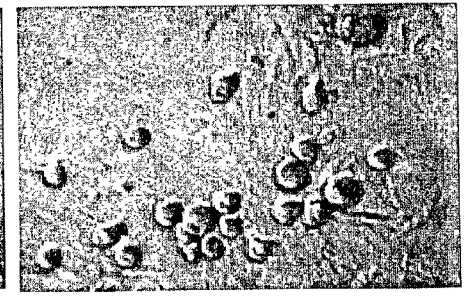

TREATMENT    CONTROL
Figure 17-A
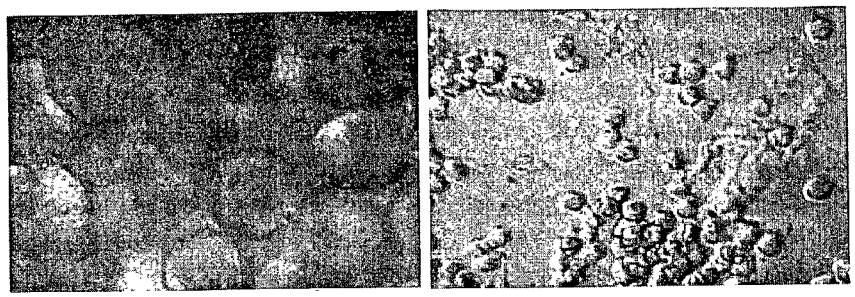
Figure 17-B
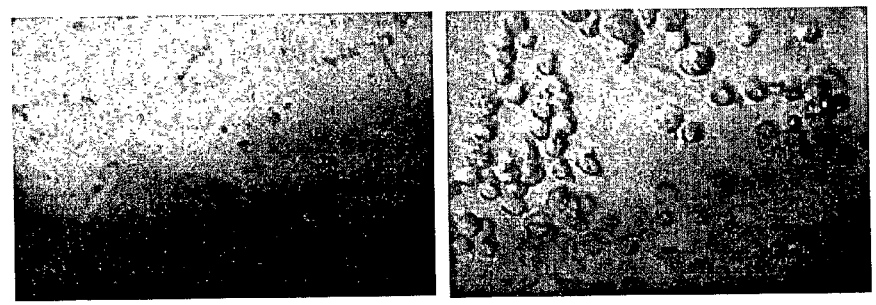
Figure 17-C

Figure 20-A
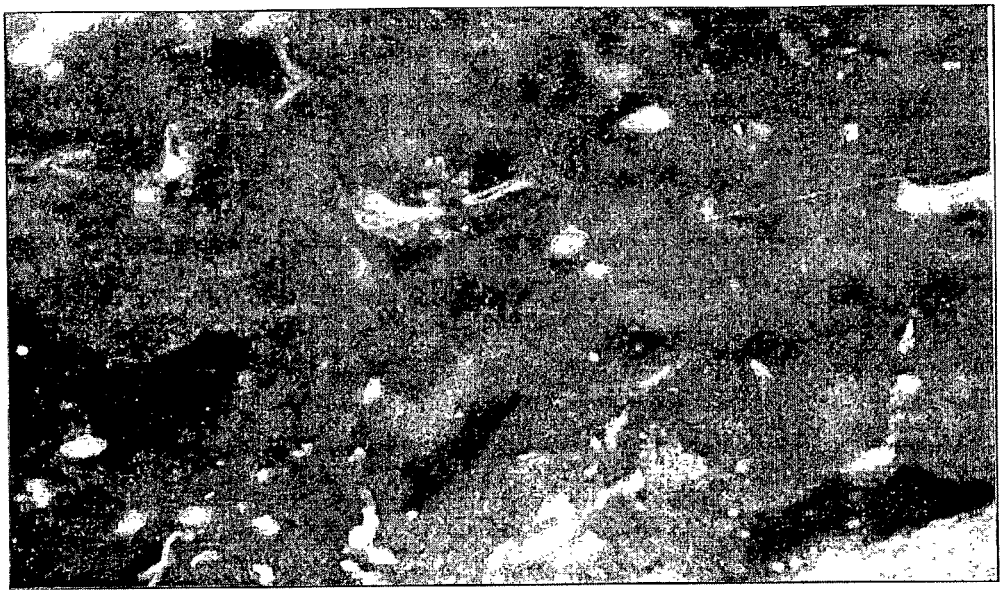
Figure 20-B
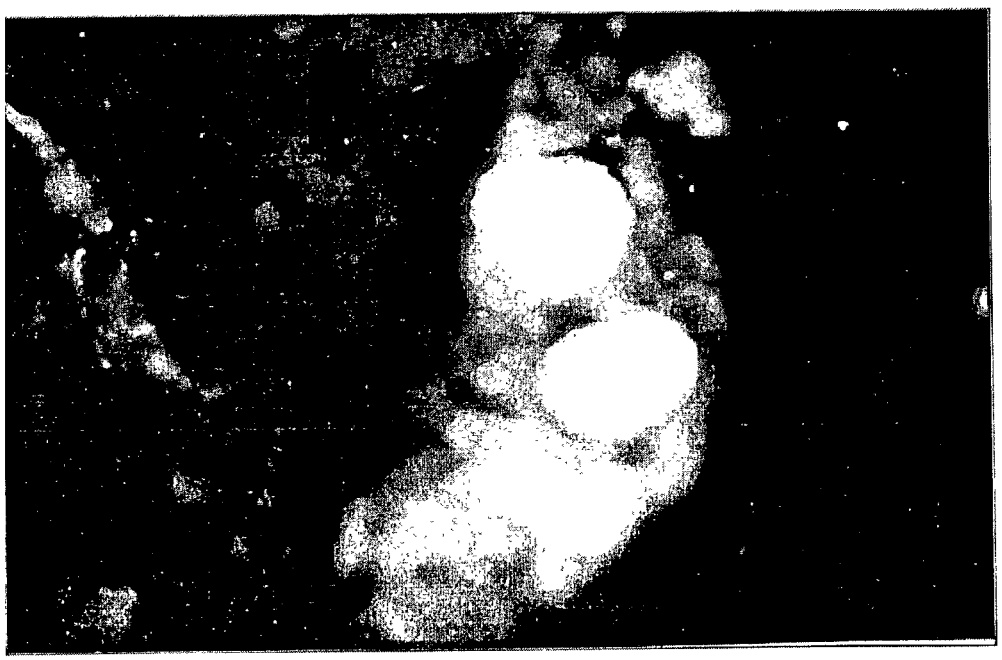

Figure 20-C
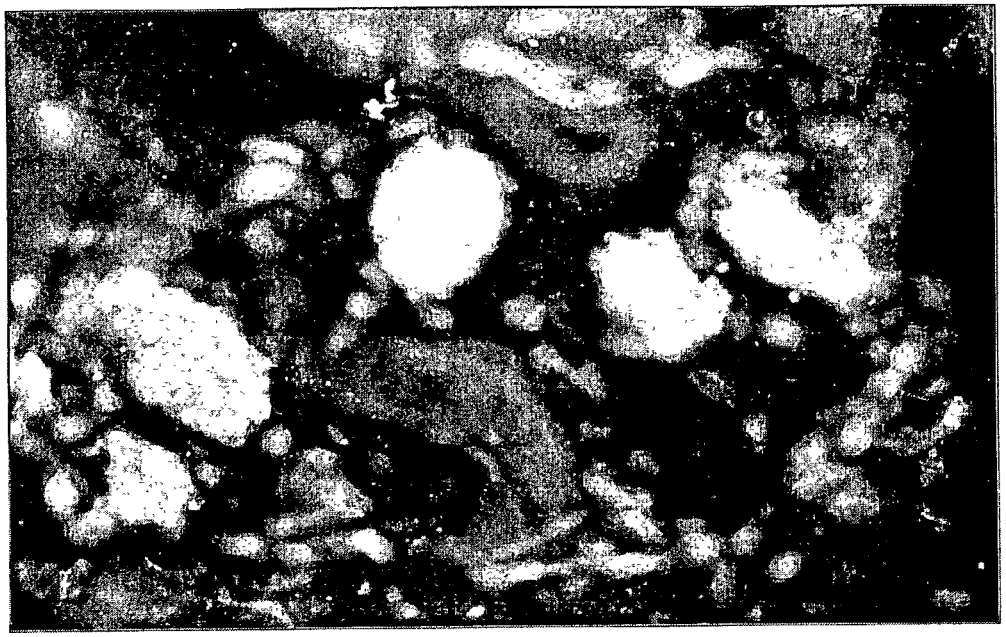
Figure 20-D
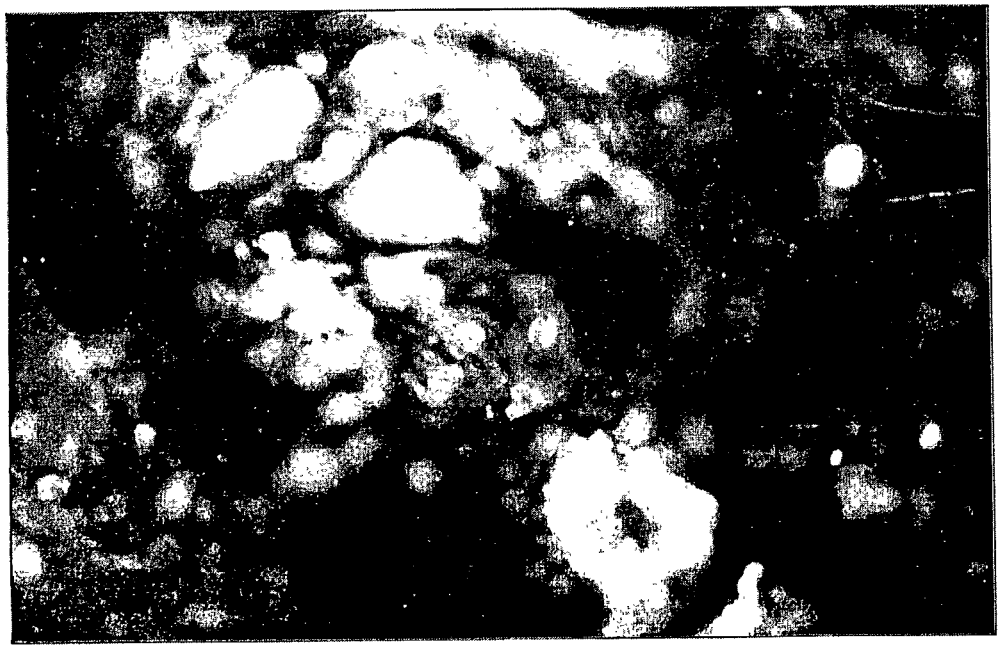

Figure 20-E
Figure 20-F
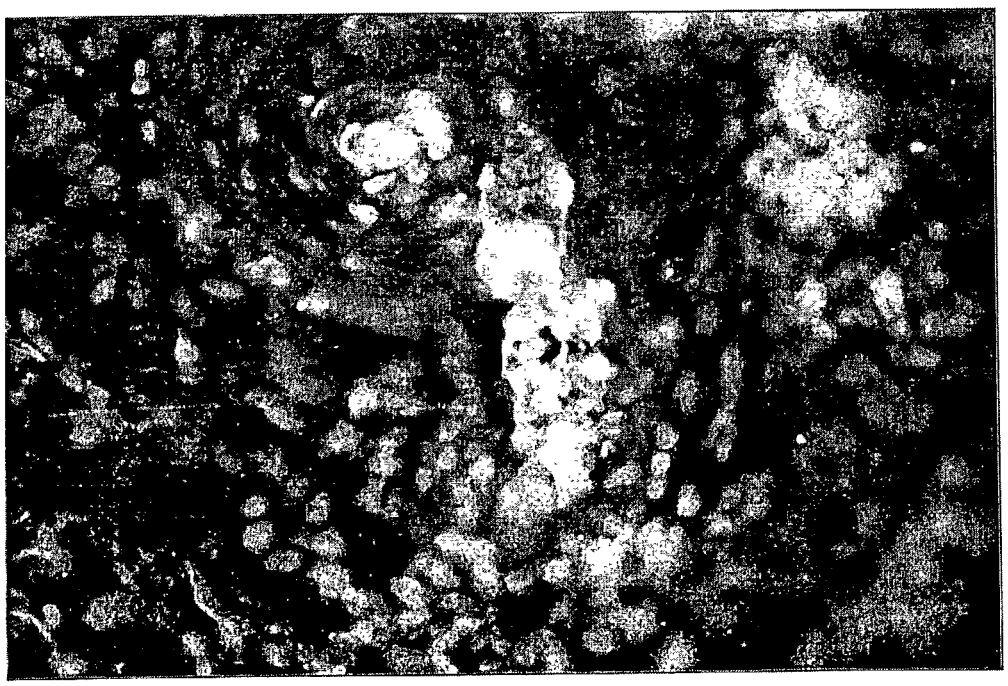

Figure 27-A
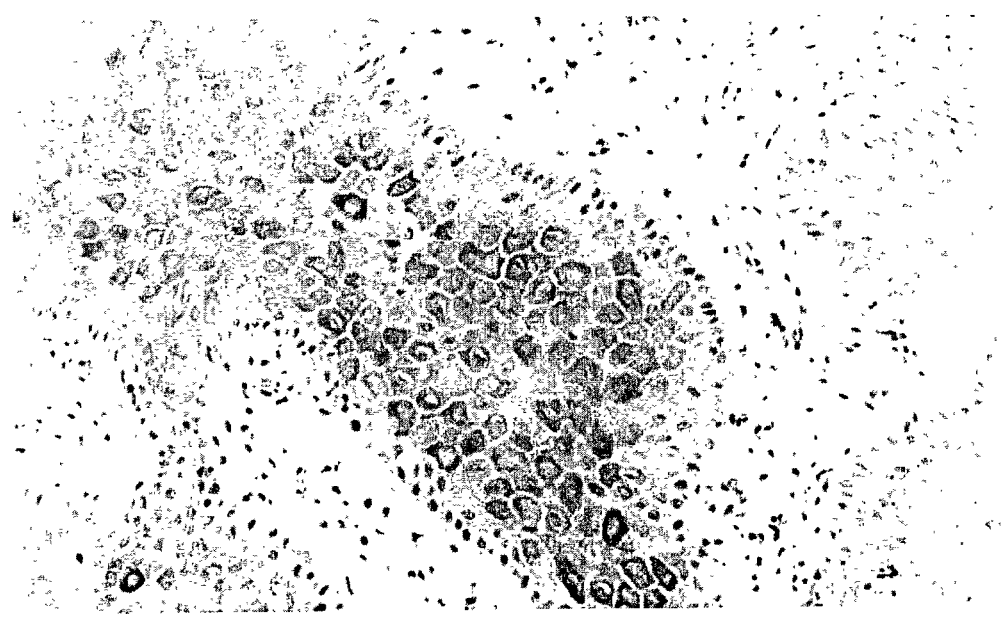
Figure 27-B
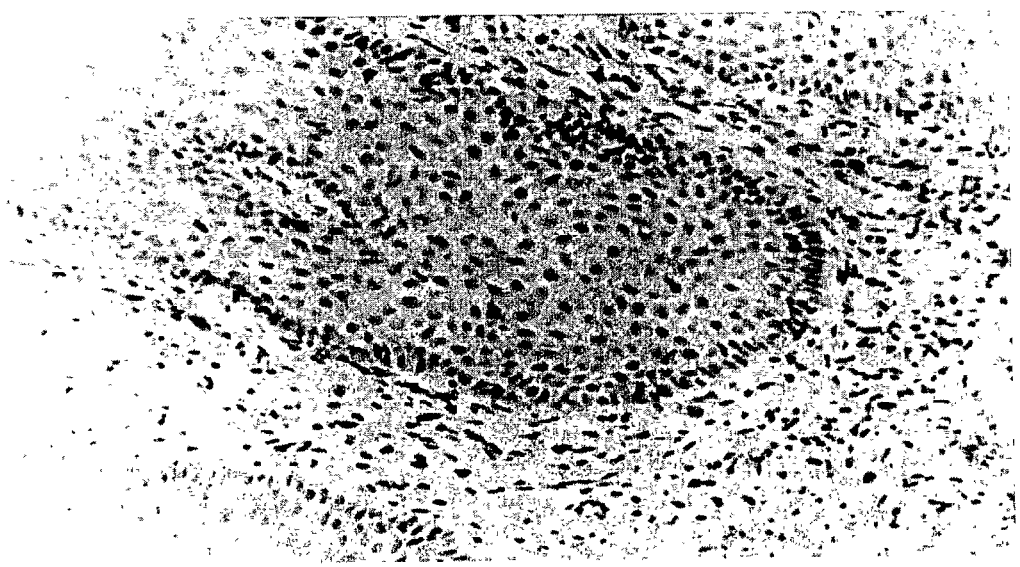

Figure 33-A
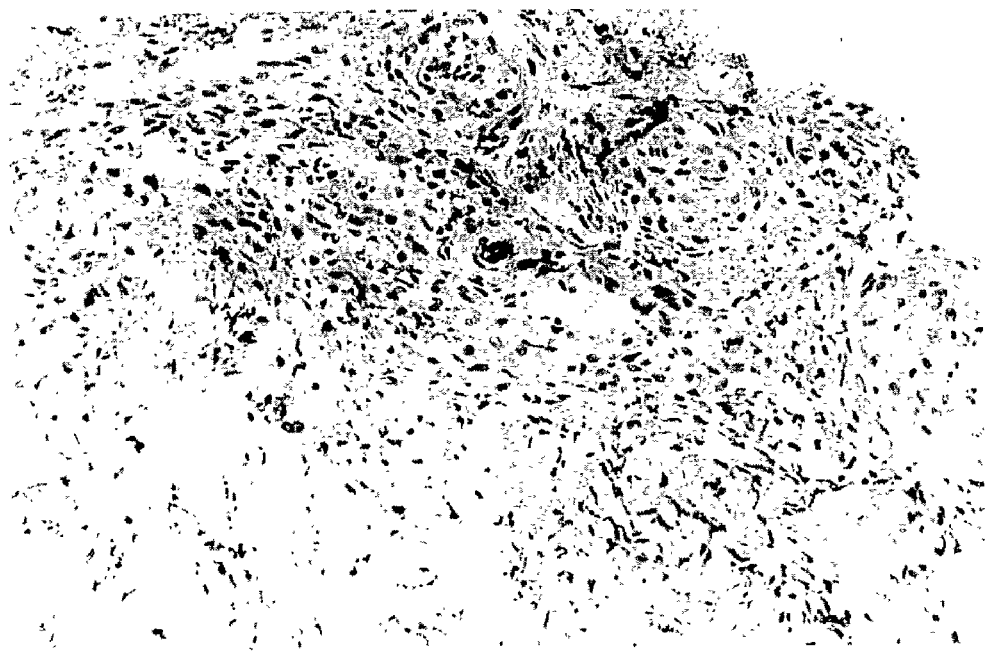
Figure 33-B
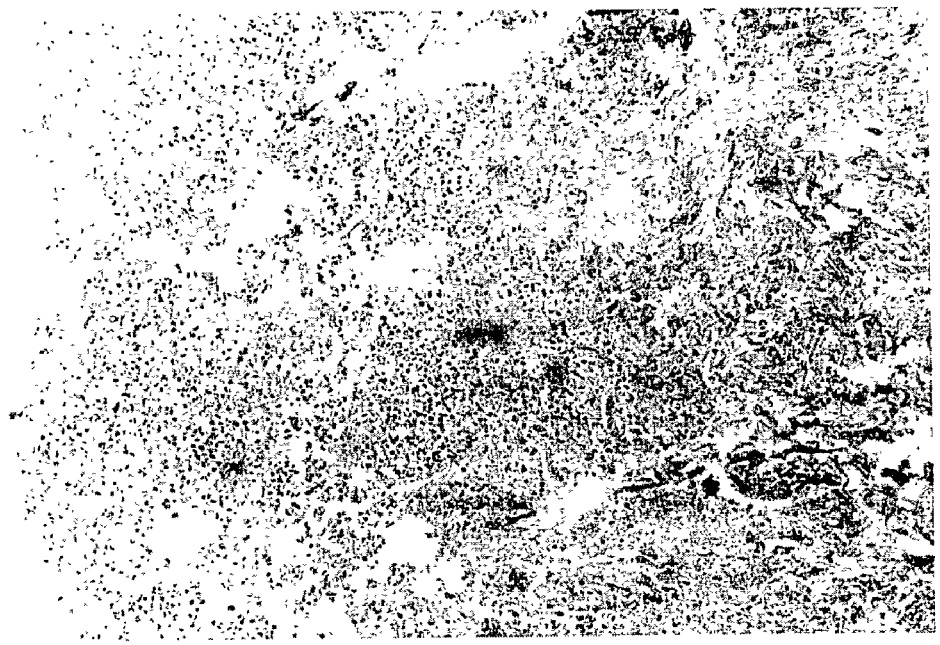

Model illustration of dosage form in a pigeonhole structure

Figure 46 - Residual Tissues in Physiologically Moist Environment

Figure 47. Comparison of burn wound evaporation between IC treatment group and auto-control group

Figure 50-A
Figure 50-B

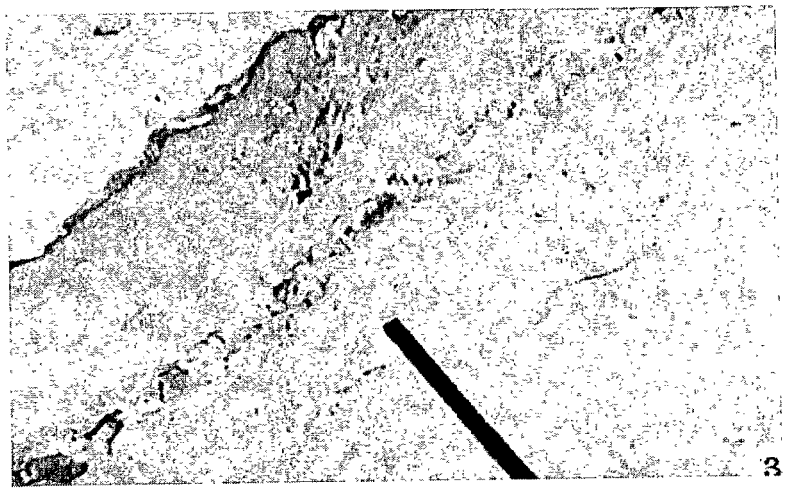
Figure 51-A
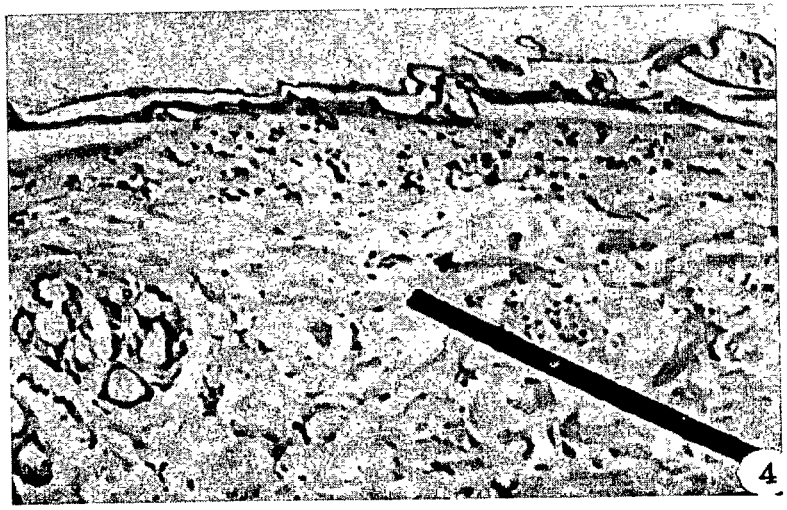
Figure 51-B
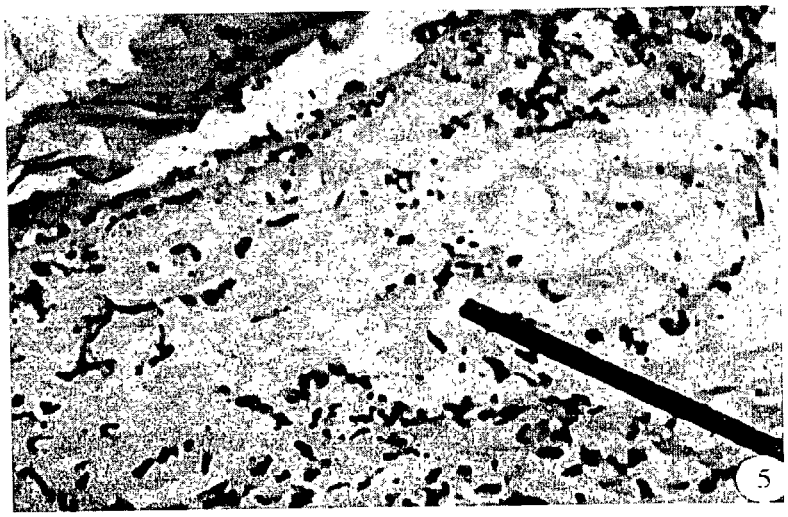
Figure 51-C

Figure 52

Comparison of healing time between wounds treated with IC and auto-control ($\bar{x} \pm s$)

| Wound | No. of wounds | Healing time (day) | P value |
|---|---|---|---|
| Auto-control | 10 | 19.80 ± 2.61 | < 0.01 |
| IC treated | 10 | 15.00 ± 1.16 | |

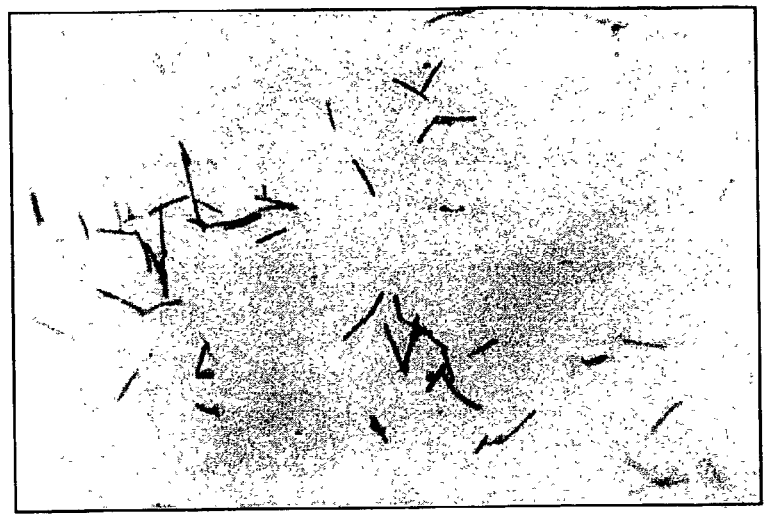
Figure 53-A
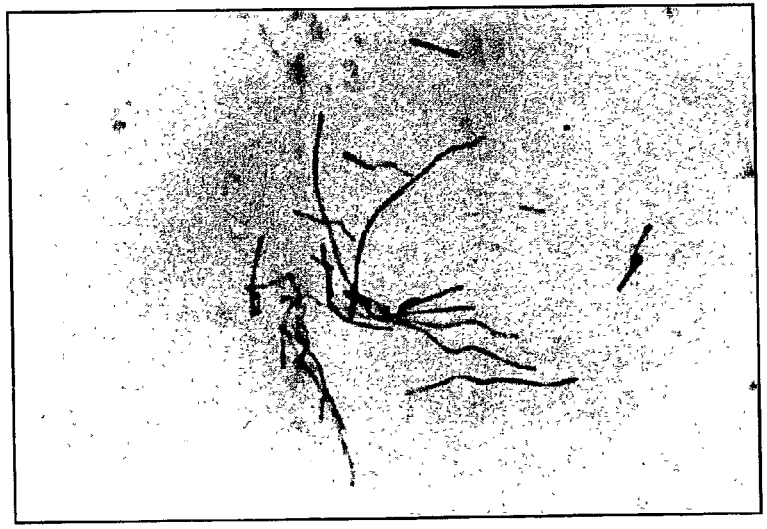
Figure 53-B
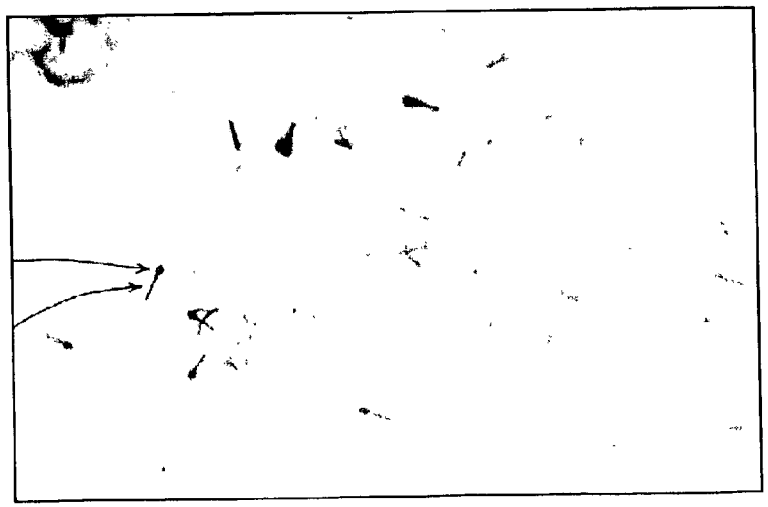
Figure 53-C

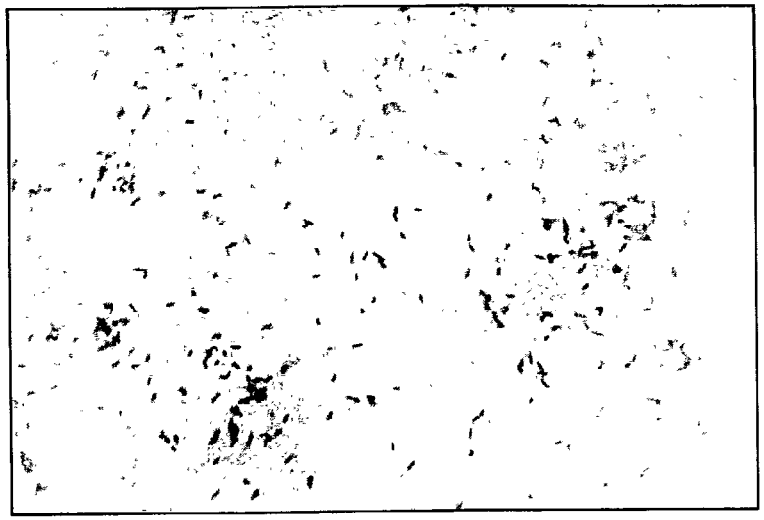
Figure 54-A
Figure 54-B
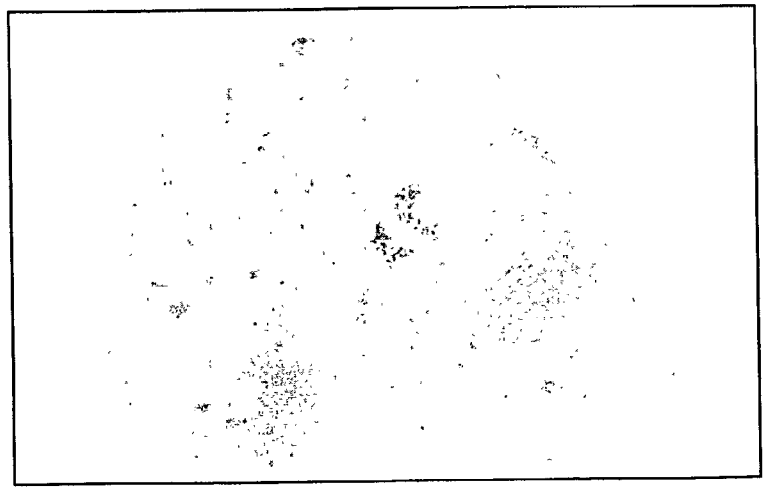
Figure 54-C

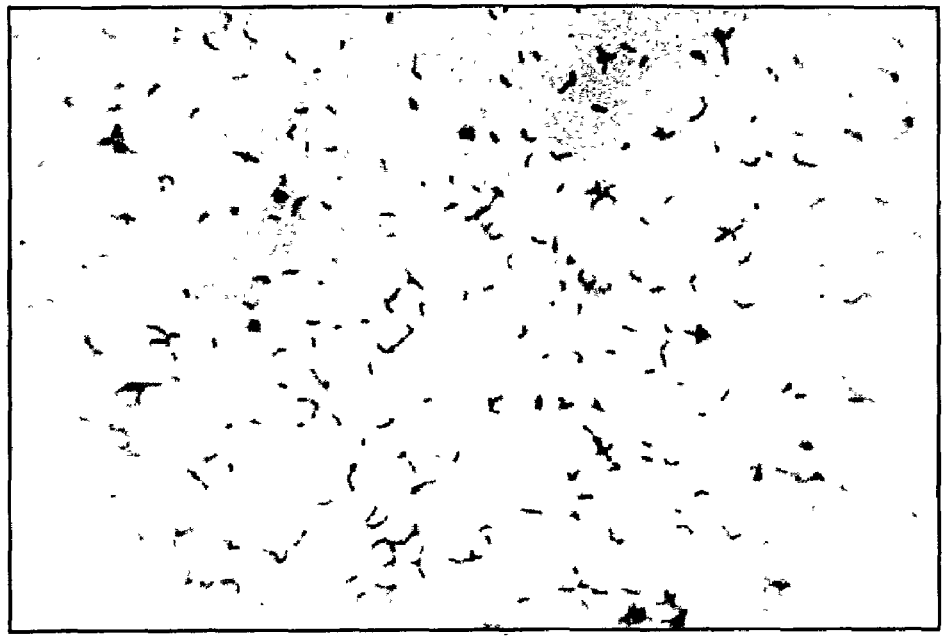
Figure 55-A
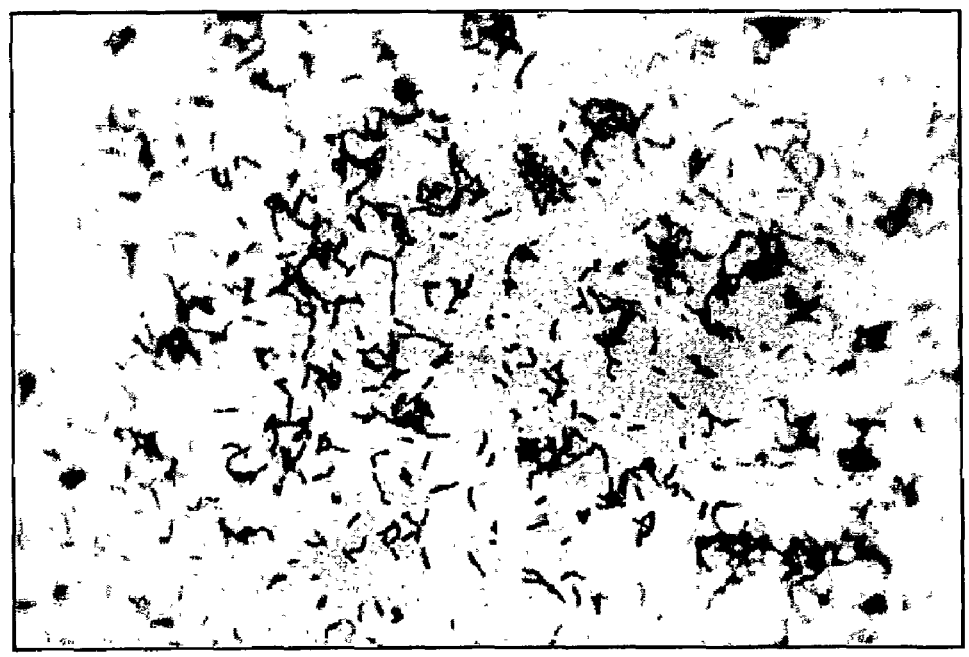
Figure 55-B

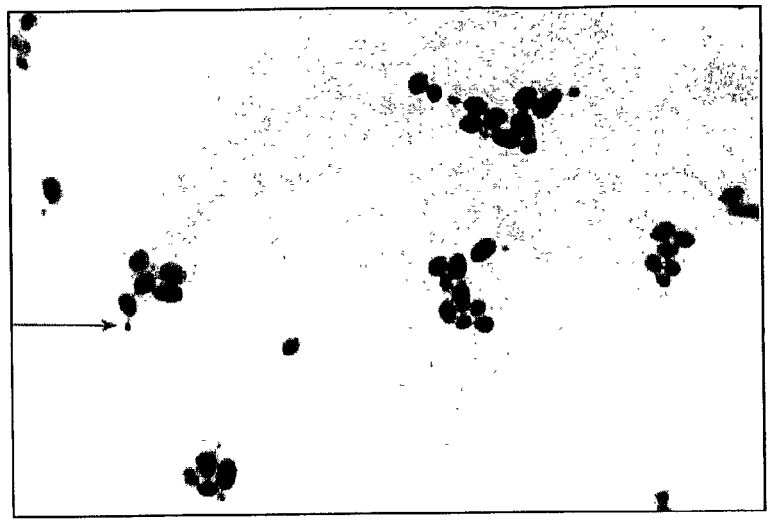
Figure 56-A
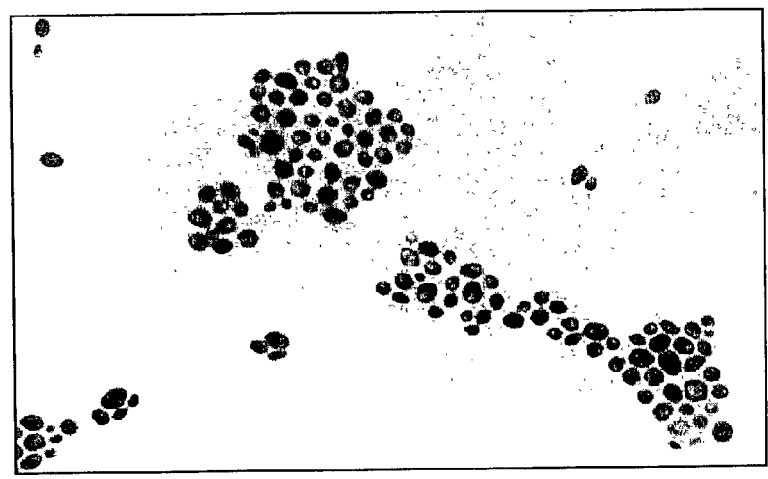
Figure 56-B
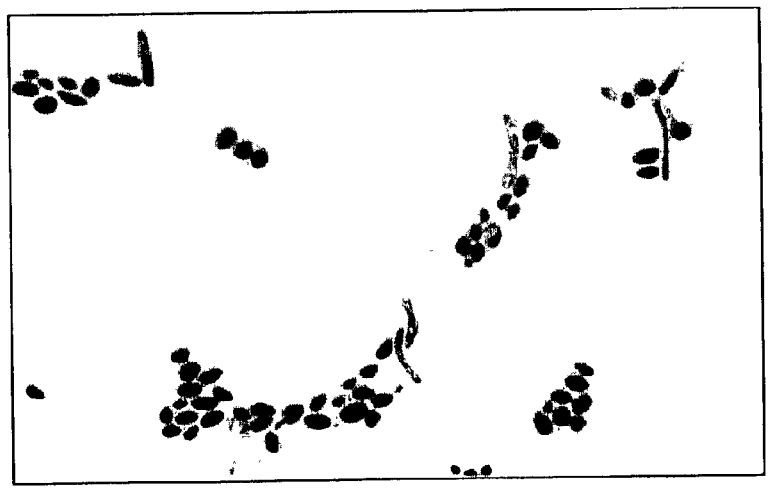
Figure 56-C

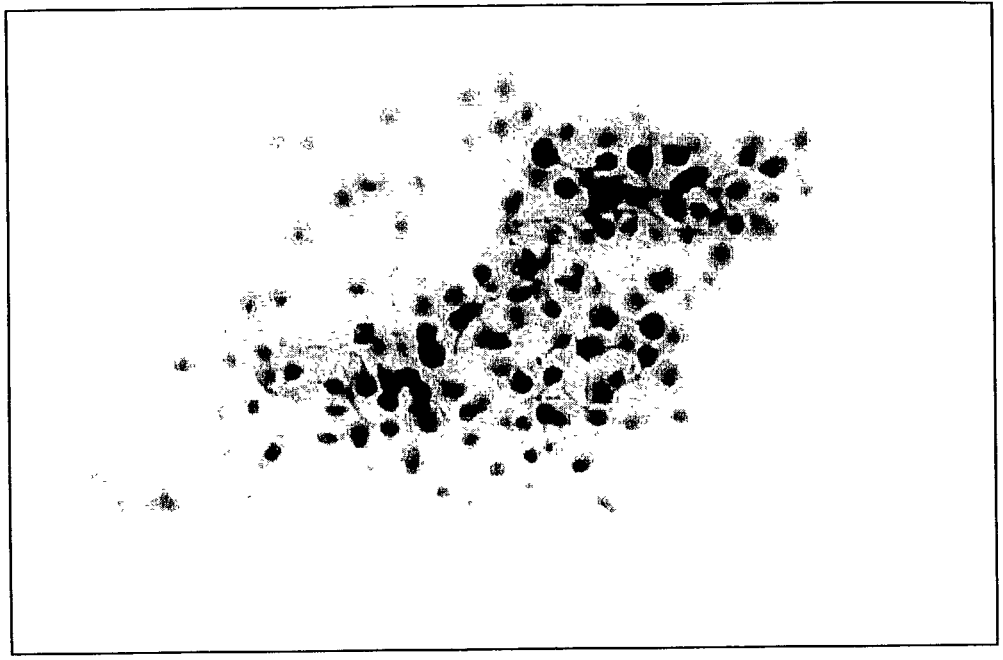
Figure 56-D
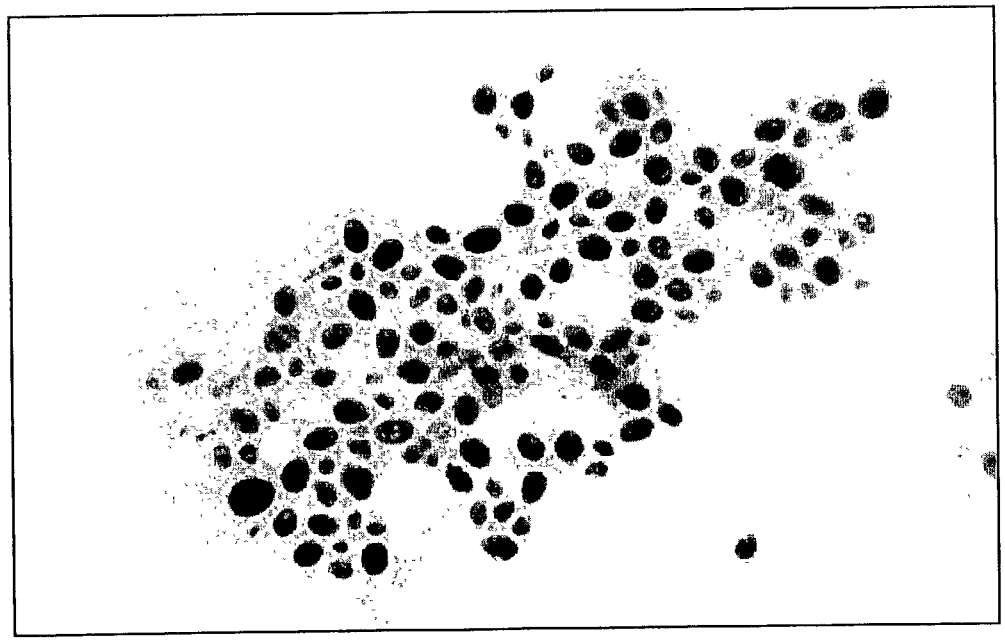
Figure 56-E

Figure 57-A
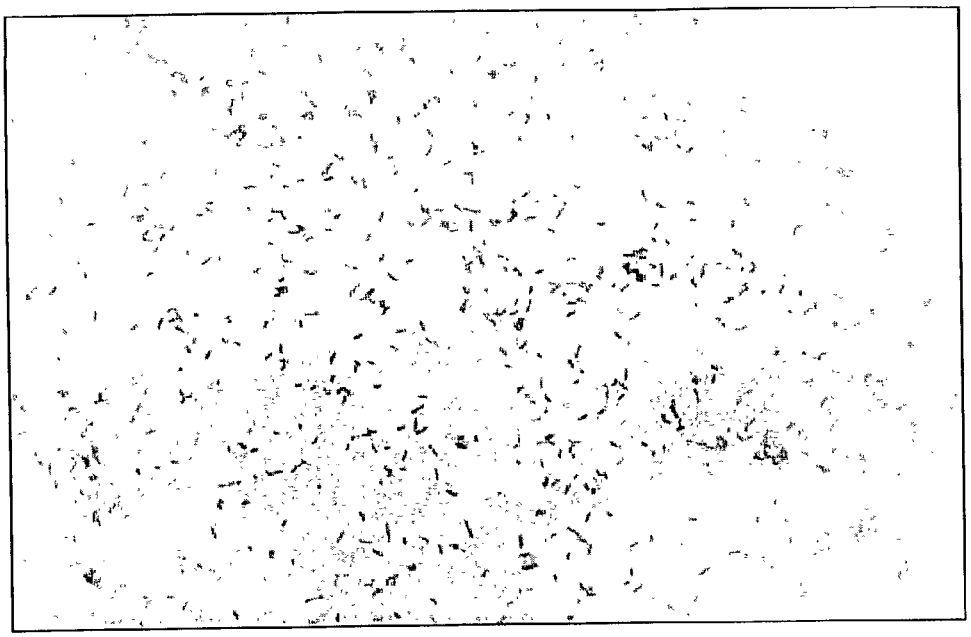
Figure 57-B
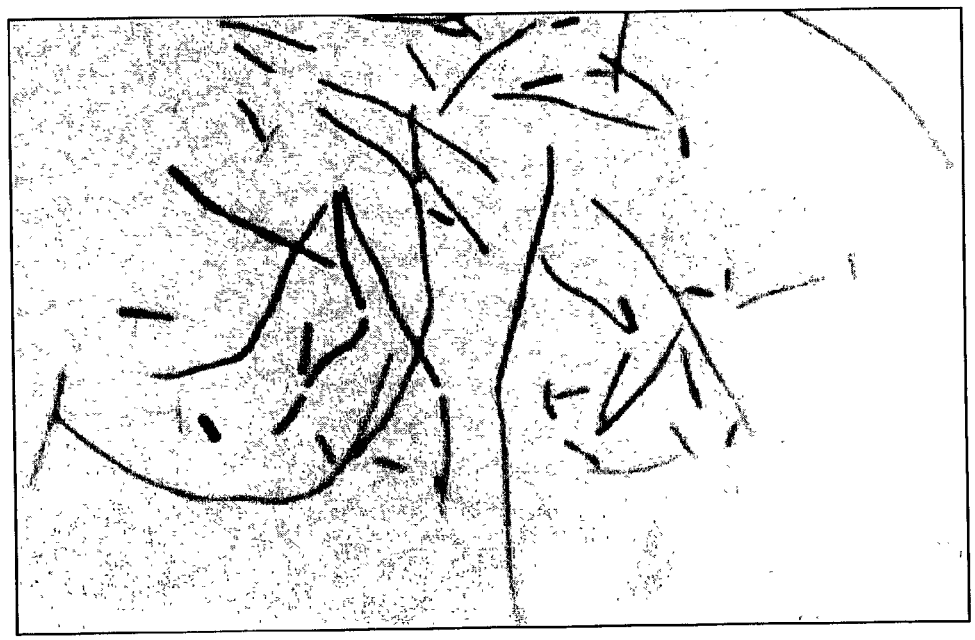

Figure 58-A
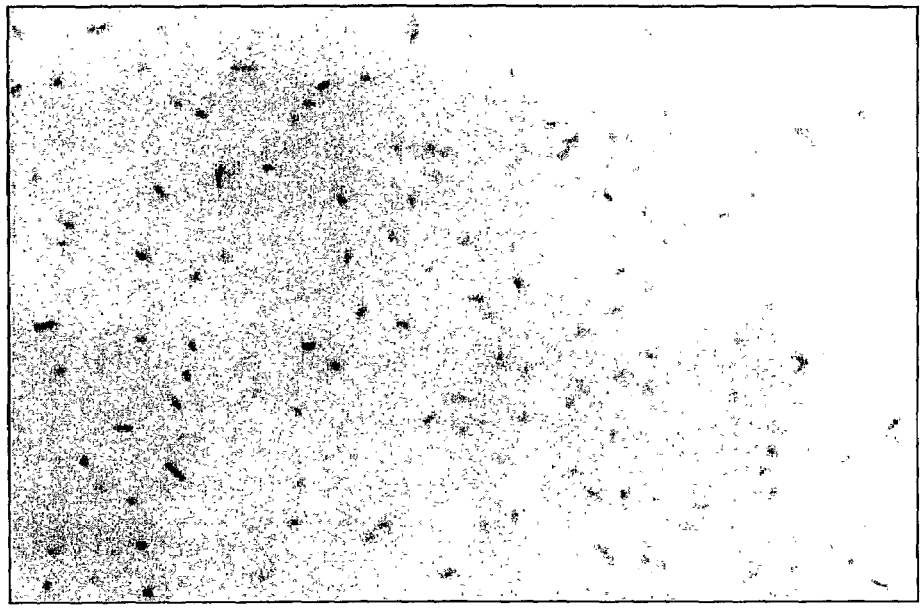
Figure 58-B

Figure 59-A
Figure 59-B
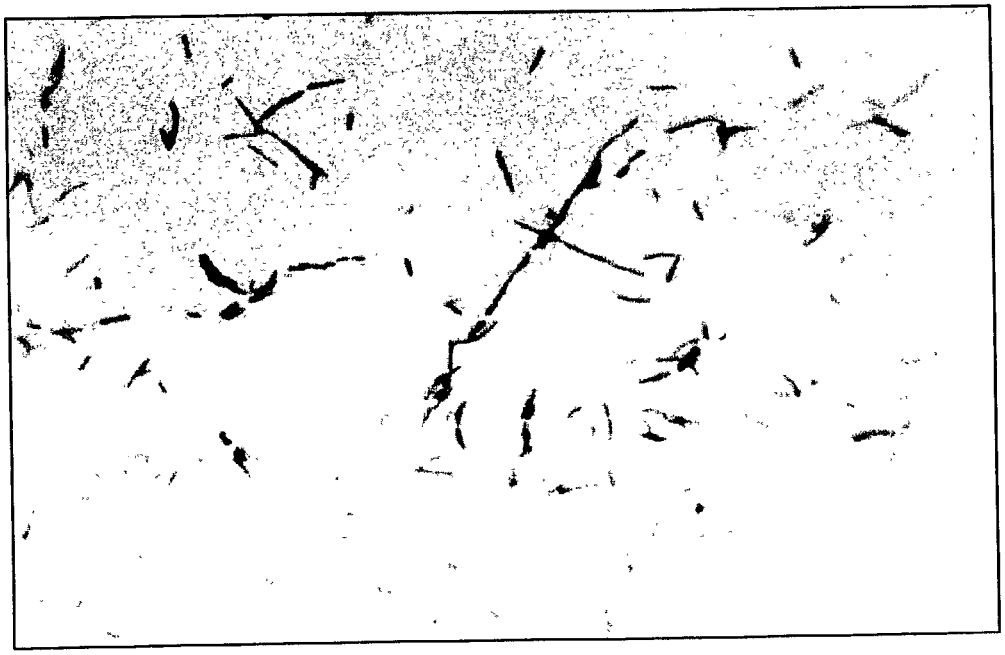

Figure 60

The effect of IC on plasma-coagulase of *Staphylococcus aureus*

| | | |
|---|---|---|
| Control (Primary Culture) | +++ | The liquid was clear with many large bacteria clots |
| IC Treated Bacteria | 1~3 generations +++ | |
| | 4~6 generations ++ | Liquid a little turbid, bacteria clots slightly fewer and smaller |
| | 7~8 generations + | Liquid turbid, very few and small bacteria clots |

Figure 61

Comparison of the effect on plasma-coagulase of *Staphylococcus aureus*

| | | | |
|---|---|---|---|
| 25 % | IC | 1~7 generations | +++ |
| 50 % | IC | 8~12 generations | ++ |
| | | 13~14 generations | + |
| | IC | 1~3 generations | +++ |
| | | 4~6 generations | ++ |
| | | 7~8 generations | + |

Figure 62

The effect of IC on the proliferation of Staphylococcus aureus and Pseudomonas aeruginosa

| Bacteria | Primary culture (No./ml) | 10th generation after cultured in IC containing media (No./ml) |
|---|---|---|
| Staphylococcus aureus | $1.4 \times 10^8$ | $7.5 \times 10^6$ |
| Pseudomonas Aeruginosa | $2 \times 10^8$ | $6.5 \times 10^6$ |

The effect of IC on the invasive power of Pseudomonas aeruginosa -- Pathological examination:

Control group -- In subcutaneous tissue there were congestion and edema, infiltration of inflammatory cells and suppurative zone.

IC group -- In subcutaneous tissue and striated muscles, there was infiltration of a few inflammatory cells without suppurative phenomenon.

PHYSIOLOGICAL TISSUE REPAIR AND FUNCTIONAL ORGAN REGENERATION BY CULTIVATION OF REGENERATIVE STEM CELLS IN VIVO AND IN SITU

RELATED APPLICATIONS

This application claims the benefit of priority from U.S. Provisional Application Ser. No. 60/301,961, filed Jun. 28, 2001, which is incorporated herein by reference in its entirety.

BACKGROUND OF THE INVENTION

1. Field of the Invention

The present invention relates to methods and compositions for tissue engineering and organ regeneration, and more particularly to methods and compositions for physiological repair of human tissues and regeneration of fully functional human organs through induction and propagation of multipotent, regenerative stem cells in vivo and in situ.

2. Description of the Related Art

The tissue engineering industry is growing at an accelerated pace owing to technological advancements in producing large scale cell culture products and biomaterials. These products are produced or synthesized ex vivo, i.e., outside an animal or human body, and then transplanted to the host for tissue repair or other therapeutic purposes.

One approach to modern tissue engineering is to implant a synthetic material into the human body as a structural scaffold for supporting the ingrowth of the tissue. For example, synthetic bone substitutes, such as α-BSM® from Etex Corp (Cambridge, Mass.), can be used for orthopedic, dental and craniofacial applications. α-BSM® is a nanocrystalline calcium phosphate that mimics the composition and structure of the mineral content of bone. When mixed with saline, it becomes a paste that can be either injected into a void or implanted as moldable putty. Once the material is in place, the hardening process is initiated by the heat of body temperature. As a result, the implant becomes a scaffold that is eventually absorbed and replaced with new bone tissue.

Another approach to tissue engineering is to utilize biological, as opposed to synthetic, matrices to provide a foundation for repair and regeneration of damaged or diseased tissues. Acellular dermal matrix is produced from fresh human cadaver skin by control process that removes the epidermis and the cells from the dermis without altering the structure of the extracellular matrix and the basement membrane complex. Wainwiright (1995) Burns 21:243–248. Acellular dermal matrix from fresh porcine skin has also been developed using a similar process in order to compensate for the lack of cadaver skin availability. Liversey et al. (1995) Transplantation 60:1–9. Recently methods have been developed by LifeCell Corp (Branchburg, N.J.) for chemically processing human skin to produce a human skin matrix. All of the skin cells are chemically removed while the bioactive, structural dermal matrix is preserved. Such a structural, biochemically intact, acellular matrix is believed to provide to a three-dimensional structural array of information that directs revascularization and repopulation in a normal regenerative response. The acellular human skin matrix serves as an allograft, i.e., a graft from a donor other than the host him/herself. The matrix is frozen in liquid nitrogen and then fractured into 100 micron particles. These small-diameter, acellular vascular grafts are being developed as an alternative to autografted blood vessels in coronary bypass procedures.

Wound healing of the skin represents a major target for tissue engineering. Repair of wound of the skin involves the timed and balanced activity of inflammatory, vascular, connective, tissue, and epithelial cells. Traditional management of large-surface or deep wounds employs the so-called dry therapy which allows the wounds to be left in a warm, dry environment to crust over. Current methods involve covering the wounds with temporary dressings and topical treatment, including antibiotics. Secondary invention, such as surgical debridement, is usually employed to remove scab or the dead tissue. For burn wounds, surgical intervention, tangential excision of a partial or full-thickness wound, is a method still widely used despite of drawbacks such as blood loss in large-surface wounds. After wound bed is prepared the wound is covered with autografts or temporary dressing to promote healing.

An autograft is harvested from the host him/herself and used as a permanent cover for the patient's own wound(s). Since the skin graft is donated by and transplanted to the patient him/herself the problems associated with immunogenicity can be avoided. The graft can be harvested from an adjacent undamaged area of the patient that matches closely in terms of texture, color, and thickness. For a small-area wound, autograft was shown to achieve good quality of healed skin by expanding the surface of the skin graft with a mesh apparatus. Tanner et al (1964) Plastic Reconstr. Surg. 34:287–292; and Richard et al. (1993) J. Burn Care Rehabil. 14:690–695. However, excessive meshing usually results in healed skin that is more susceptible to infections and which has a basket-like pattern, an undesirable result aesthetically. Alternative methods, such as the Meek island graft or sandwich graft, were also developed, which allows easier handling widely expanded autografts than meshed skin. Meek (1954) Am. J. Surg. 96:557–558; and Kreis et al. (1994) Burns 20(suppl 1) S39–S42.

However, the autograft method faces a few challenges and limitation in the treatment of patients with large surface area wounds. It has been realized that a deep burn or large-surface wounds could not be completely closed promptly after injury by using the patient's available autograft donor sites. Adequate, healthy skin donor sites are difficult to find in such patients. There is also a time limitation for harvesting the graft from the same site. Often, a delay of several weeks is necessary to wait for healing of the donor sites before harvesting them again, thus delaying healing of the "main" wound—the original wound to be treated and increasing the risk of complication. Even worse is that harvesting an autograft in fact creates a second wound in the normal healthy skin, which increases the risk of infection and fluid/electrolyte imbalance. In addition, repeated harvests of autografts from a donor wound site can result in contour defects or scarring, thereby causing disfigurement of the patient.

To find a substitute for the autologous split-thickness grafts described above a two-step procedure has been developed using composite autologous-allogenic skin replacement. Such a graft consists of a skin allograft which has its epidermis removed to serve as a dermis substitution for the patient, and autologous epidermis reconstructed in vitro with the patient's own keratinocytes. Cuono et al. (1986) Lancet 17: 1123–1124; and Compton et al. (1989) Lab. Invest. 60:600–612. The autologous epidermis is usually constructed in vitro by using the technique developed by Rheinwald and Green (1975) Cell 6:331–344. This technique consists of digesting a small biopsy of healthy skin in trypsin or in thermolysin in order to isolate keratinocytes from the basal layer of the epidermis. By culturing the autologous keratinocytes in vitro a large number of cells are available for generate enough epidermis for grafting.

This two-step approach suffers a few limitations. First, growth of cultured epidermal sheets in a laboratory needs at least 3 weeks to be achieved, thus delaying the coverage of wounds. The successful treatment demands highly sophisticated laboratories and well trained physicians/surgeons in the whole process of epidermal sheet production and grafting on the wound bed. This limitation is even more prominent in areas where such laboratory and human resources are not available, such as the battle fields and the rural areas of developing countries. Second, the reconstructed epidermal sheets need to be grafted on a clean wound bed since they are highly sensitive to bacterial infection and toxicity of residual antiseptics. Thus, proper preparation of the wound bed is critical for the survival of the fragile epidermal sheets. More significantly, although the epidermal sheet can attach to the dermis, the conjunction between these two layers is artificial relative to the natural skin. Since the regeneration of the dermal compartment underneath the epidermis is a lengthy process the skin remains fragile for at least three years and usually blisters. In addition, the aesthetic effect is usually not as good as with one obtained with a split-thickness graft.

To provide the dermal structure for the cultured epidermal sheet and promote graft takes, allogeneic skin has been used to cover the wound. After debridement, cadaver allograft is used to over the wound and the allogeneic epidermis is excised in order to maintain the allogeneic dermis on the wound. The cultured epidermal sheet is then grafted on the de-epidermized cadaver allograft. The cadaver allograft is non-vital and thus has a much-reduced antigenicity.

To overcome problems associated with delayed transplantation due to time required for culturing autologous epidermal sheet allogeneic cultured epidermal sheets were tested clinically and experimentally. Unfortunately, even though the allograft is depleted of Langerhans' cells, the rejection of the transplant by the host occurs in mice after about 2 weeks. Rouabhia (1993) Transplantation 56:259–264.

Xenogeneic grafts, i.e., tissues of other animal origin, have also been used to cover extensive wounds. Porcine skin is the most common source of xenograft because of its high similarity to human skin. Sterilization (e.g., ionizing radiation) coupled with freeze-drying seems to decrease the antigenic properties of the pigskin graft and increase its potential to inhibit bacterial growth. The xenografts are used mostly as a temporary dressing for the coverage of second-degree burns, especially after early excision. Pellet et al. (1984) in Burn Wound Coverings, Wise D L, ed., Boca Raton, CRC Press, Florida, 1:85–114.

Artificial dermal matrices have been developed to cover wounds in order to facilitate graft take of cultured epidermal sheets and to prevent rejection of xenogeneic tissues. They are used to prompt coverage of large excised full-thickness wounds, control fluid loss, and prevent infection. Examples of such artificial dermal matrices include 1) synthetic mesh composed of nylon or a polyglactic acid mesh on which fibroblasts are cultured (Rennekampff et al. (1996) J. Surg. Res. 62:288–295); 2) collagen gel made of a mixture of fibroblasts and bovine collagen (Yanna et al. (1981) Trans. Am. Soc. Artif. Intern. Organs 27:19–23); collagen sponge based on the production of a lyophilized collagen matrix in which fibroblasts are cultured and migrate (Bell et al. (1979) Proc. Natl. Acad. Sci. USA 76:1274–1278 and Bell et al. (1981) J. Invest. Dermatol. 81:S2–S10); collagen membrane (Ruszczak et al. (1998) Ellipse 14:33–44); and in vitro reconstructed skin-like products based on collagen matrix (Sabolinski (1996) Biomaterials 17:311–320).

The xenogeneic graft approach has a few limitations in clinical treatment of wounds, most prominent being immunogenicity and biocompatibility. The level of natural antibodies of the transplant host which react with organ xenotransplants increases proportionally with phylogenic distance between the xenogeneic species involved. In organ transplantation, the presence of such antibodies leads to hyperacute rejection, which occurs within minutes to hours after revascularization, and to the loss of the transplanted tissue.

To provide a large amount of keratinocytes for reconstructing autologous or allogenic epidermal sheets in vitro, great efforts have been made to cultivate human keratinocyte stem cells in culture. Keratinocytes forming the epidermal basal layer are endowed with proliferative capacity, hence they regularly undergo mitosis, differentiation and upward migration to replace terminally differentiated cornified cells that are continuously shed into the environment. The epidermis relies on the presence of keratinocyte stem cells to accomplish wound healing. The basic, essential and indispensable characteristics of a stem cell is its capacity for extensive self-maintenance with the potential for proliferative self-renewal extending for at least one lifespan of the organism. Lajtha (1979) Differentiation 14:23–34. Thus, a stem cell can divide to generate transient amplifying cells which can differentiate into one or more specialized cell types.

Keratinocyte stem and transient amplifying cells are located both in the epidermal basal layer and in the hair matrix. Lavker et al. (1983) J. Invest. Dermatol. 81:121s–127s; and Rochat et al. (1994) Cell 76:1063–1073. In preparing epidermal sheets for transplant basal keratinocytes are cultivated in culture to produce large numbers of progeny. Maintaining these stem cells in culture conditions can be challenging. The quality of the keratinocyte culture system must be carefully monitored by directly demonstrating the presence of holoclones in culture, periodical clonal analysis of a reference strain of keratinocyte both in terms of clonogenic and growth potential, and monitoring the percentage of aborted colonies. Inappropriate culture conditions can irreversibly accelerate the clonal conversion and can rapidly cause the disappearance of stem cells, rendering the cultured autograft or allograft transplantation useless.

Besides keratinocyte stem cells, other types of stem cells are cultivated in cell culture in an attempt to provide sufficient amount of cells for tissue repair or other therapeutic use. Embryonic stem (ES) cells can be cultured under proper conditions. Thomson et al. demonstrated that cells from the inner cell mass (ICM) of mammalian blastocysts can be maintained in tissue culture under conditions where they can be propagated indefinitely as pluripotent embryonic stem cells. Thomson et al. (1998) Science 282:1145–1147. Primate blastocysts were isolated from the ICM from the blastocysts and plated on a fibroblast layer wherein ICM-derived cell masses are formed. The ICM-derived cell mass were removed and dissociated into dissociated cells which were replated on embryonic feeder cells. The colonies with compact morphology containing cells with a high nucleus/cytoplasm ratio, and prominent nucleoli were selected and the cells of the selected colonies were then cultured. In this way, a primate embryonic stem cell line was established. It was observed that after undifferentiated proliferation in vitro for 4 to 5 months, these cells still maintained the developmental potential to form trophoblast and derivatives of all three embryonic germ layers, including gut epithelium (endoderm); cartilage, bone, smooth muscle, and striated muscle (mesoderm); and neural epithelium, embryonic ganglia, and stratified squamous epithelium (ectoderm). Thus, it is envisioned that these ES cells can be cultured and regulated under suitable conditions to coax the pluripotent cell to differentiate into cells of a particular tissue type and/or to form various organs in vitro. These cells and organs, wishfully, could be used as transplants to cure various diseases and replace dysfunctional body parts.

Although desirable, an in vitro embryonic development process is highly unpredictable. The conditions under which ES cells differentiate into a specific type of cell or organ are elusive. It has been found that to maintain cultured ES cells in their relatively undifferentiated, pluripotent state, they must both express the intrinsic transcription factor Oct4, and constitutively receive the extrinsic signal from the cytokine leukemia inhibitor (LIF). Nichols et al. (1998) Cell 95:379–391. Upon withdrawal of LIF, cultured ES cells spontaneously aggregate into a mass of cells of various tissue types. Although the programs of gene expression in these cells somewhat resemble the differentiation pathways typical of developing animals, the triggering of these programs is chaotic.

For successful organ regeneration in the clinic using stem cells cultured in vitro, a major obstacle lies in its way. Stem cells cultured in vitro must be directed to differentiate into site-specific phenotypes once they are transplanted into the lesion site. Complete deciphering of the signal needed for this process is required to guide the design of the in vitro tissue culturing conditions. Experimental data obtained by others in the art show that although multipotent human mesenchymal, mouse neural stem cells, and mouse embryonic stem cells can be grown in vitro through the addition of leukemia inhibitory factor (LIF) to the culture medium, mouse ESCs differentiate randomly in vitro and in vivo. Progress in the art has made it possible to induce differentiation of mouse ESCs into multipotent glial cell precursors in vitro and to transplant them into the brain of myelin-deficient fetal rats. However, question remains unanswered as to whether these multipotent stem cells harvested from specific tissues or differentiated from ESCs in vitro will make site-specific tissue when transplanted to injured adult tissues.

Up to date enormous amounts of money and efforts have been made in attempts to repair damaged tissue and dysfunctional organs through cultivation of stem cells in vitro. However, no successful regeneration of a fully functional human organ has been reported by using this approach. For example, treatment of wounds with in vitro cultivated keratinocyte stem cells merely closes the wound, not resulting in a full restoration of the physiological structure and function of the skin. Therefore, there exists an urgent need for innovative approaches that depart from the above strategies and provide greater benefits to human health.

SUMMARY OF THE INVENTION

The present invention provides novel compositions and methods for pharmaceutical or nutraceutical use in an animal, preferably in a human. In addition, methods for manufacturing the compositions are also provided.

In one aspect of the invention, compositions are provided for promoting cell growth, tissue repair and organ regeneration, preferably in vivo and in situ. In one embodiment, the composition comprises a sterol compound dissolved in oil at a concentration at least 0.5% by weight based on the total weight of the composition, preferably a sterol compound dissolved in a fatty acid-containing oil at a concentration at least 1% by weight based on the total weight of the composition. In the composition, the sterol compound preferably forms ester with the fatty acid in the oil under suitable conditions such as high temperature (e.g., >100° C.).

The concentration of the sterol compound preferably ranges from about 1.2% to 40% by weight, more preferably about 1.2% to 20% by weight, and most preferably about 2% to 6% by weight.

The fatty acid-containing oil is preferably vegetable oil, more preferably vegetable oil selected from the group consisting of corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof, and most preferably sesame oil.

The fatty-acid is preferably selected from the group consisting of palmitic acid, linoleic acid, oleic acid, trans-oleic acid, stearic acid, arachidic acid, and tetracosanoic acid.

According to this embodiment, the composition may further comprise wax at a concentration ranging from about 1% to 20% by weight, more preferably from about 2% to 10% by weight, and most preferably from about 3% to 6% by weight based on the total weight of the composition.

The wax is preferably edible wax, more preferably edible wax selected from the group consisting of beeswax, castor-wax, glycowax, and carnaubawax, and most preferably beeswax.

In a preferably embodiment, beeswax in the composition forms a pigeon-hole like structure at ambient temperature or below. The dimension of at least 50% of the holes in the pigeon-hole like structure is preferably below 50 micron, more preferably below 30 micron, and most preferably below 20 micron. In a particular embodiment, the dimension of at least 50% of the holes in the pigeon-hole like structure is between 10–50 micron.

In another embodiment, a composition suitable for oral administration comprises: a sterol compound dissolved in edible oil, the concentration of the sterol ranging from about 0.5% to 20% by weight.

According to this embodiment, the composition may further comprise bees wax at a concentration ranging from about 1% to 20% by weight, more preferably from about 2% to 10% by weight, and most preferably from about 3% to 6% by weight based on the total weight of the composition.

Alternatively, the composition may further comprises propolis at a concentration ranging from about 0.1% to 30% by weight, more preferably from about 1% to 20% by weight, and most preferably from about 5% to 10% by weight based on the total weight of the composition.

The composition preferably contains minimum amount of water, preferably contains less than 10% of water by weight, more preferably contains less than 1% of water by weight, and most preferably contains less than 0.1% water by weight based on the total weight of the composition.

For oral administration, the inventive composition can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated.

In a preferred embodiment, the inventive composition is contained in capsules. Capsules suitable for oral administration include push-fit capsules made of gelatin, as well as soft, sealed capsules made of gelatin and a plasticizer, such as glycerol or sorbitol. More preferably, the inventive composition is contained in soft capsules. The inventive composition may be dissolved or suspended in suitable liquids, such as fatty oils or liquid polyethylene glycols. In addition, stabilizers may be added.

Optionally, the inventive composition for oral use can be obtained by mixing the inventive composition with a solid excipient, optionally grinding a resulting mixture, and processing the mixture of granules, after adding suitable auxiliaries, if desired, to obtain tablets or dragee cores.

In yet another embodiment, the composition suitable for parenteral administration in the clinic is provided. The composition comprises: a sterol compound dissolved in an injectable oil at a concentration at least 0.5% by weight. The concentration of the sterol compound preferably ranges from about 0.5% to 40% by weight, more preferably about 1% to 10% by weight, and most preferably about 2% to 6% by weight.

The injectable oil is preferably vegetable oil that has been processed to render it suitable for clinical injection into a human, preferably selected from the group consisting of corn oil, peanut oil, cottonseed oil, safflower oil, tea tree oil, sesame oil, pine nut oil, macadamia nut oil, camellia seed oil, grape seed oil, rose hip oil, olive oil or soybean oil, and most preferable soybean oil.

In yet another embodiment, the composition suitable for parental administration comprises: a clinically accepted fatty emulsion having an oil phase and a sterol compound dissolved in the oil phase at a concentration at least 0.5% by weight. The concentration of the sterol compound preferably ranges from about 0.5% to 20% by weight, more preferably about 1% to 10% by weight, and most preferably about 2% to 6% by weight.

The clinically accepted fatty emulsion comprises at least one vegetable oil, preferably corn oil, peanut oil, safflower oil, sesame oil, olive oil or soybean oil. Clinically accepted fatty emulsions usable in the practice of the present invention include emulsions such as LIPOSYN, SOYACAL, INTRALIPID or TRAVEMULSION, for example. The formulation of the present invention is preferably essentially free of exogenous detergent.

According to any of the above embodiments, the sterol compound may be an animal sterol or a plant sterol (also called phytosterol). Examples of animal sterol include cholesterol and all natural or synthesized, isomeric forms and derivatives thereof. Preferably, the sterol compound is selected from the group consisting of stigmasterol, campesterol, β-sitosterol, chalinosterol, clionasterol, brassicasterol, α-spinasterol, daucosterol, avenasterol, cycloartenol, desmosterol, poriferasterol, and all natural or synthesized, isomeric forms and derivatives thereof. More preferably, the sterol compound is a combination of stigmasterol, β-sitosterol, and campesterol, collectively referred to herein as "sitosterol".

Optionally, the sterol compound is a combination of stigmasterol and β-sitosterol.

Also optionally, the sterol compound is a combination of brassicasterol and β-sitosterol.

Also optionally, the sterol compound is a combination of brassicasterol, stigmasterol and β-sitosterol.

Also optionally, the sterol compound is a combination of campesterol, stigmasterol and β-sitosterol.

It is to be understood that modifications to the sterol compound i.e. to include side chains also fall within the purview of this invention. It is also to be understood that this invention is not limited to any particular combination of sterols forming a composition.

Alternatively, the sterol compound may be dissolved in a pharmaceutically-acceptable, water-miscible, non-fatty acid solvent and used for parental administration. Examples of such a solvent include, but are not limited to, N-methyl pyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (s)-(-)-ethyl lactate; acetone; glycerol; alkyl ketones such as methylethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

Solubilizers may also be used in conjunction with this type of solvent to render the sterol compound more soluble in solution. Solubilizers useful in the practice of this invention include, but are not limited to, triacetin, polyethylene glycols (such as PEG 300, PEG 400, or their blend with 3350), polysorbates (such as Polysorbate 20, Polysorbate 40, Polysorbate 60, Polysorbate 65, or Polysorbate 80), poloxamers (such as Poloxamer 124, Poloxamer 188, Poloxamer 237, Poloxamer 338, or Poloxamer 407), polyoxyethylene ethers (such as Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether), polyoxylstearates (such as Polyoxyl 30 stearate, Polyoxyl 40 stearate, Polyoxyl 50 stearate, Polyoxyl 100 stearate), polyethoxylated stearates (such as a polyethoxylated 12-hydroxy stearate), and Tributyrin. In a preferable embodiment, pharmaceutically-acceptable solubilizers are excluded from the inventive composition. In another preferable embodiment, polyoxyethylated castor oil is excluded from the inventive composition.

According to any of the above embodiments, the inventive composition may further comprise baicalin, preferably at a concentration ranging from about 0.001 to 2% by weight, more preferably about 0.02 to 1% by weight, and most preferably about 0.02% to 0.5% by weight based on the total weight of the composition.

According to any of the above embodiments, the inventive composition may further comprise an extract of huangqin in an amount of 10–90% by weight based on the total weight of the composition, wherein the amount of huangqin is 2–60% by weight based on the total weight of the oil.

Also according to any of the above embodiments, the inventive composition may further comprise obaculactone, preferably at a concentration ranging from about 0.001 to 2% by weight, more preferably about 0.02 to 1% by weight, and most preferably about 0.02% to 0.5% by weight based on the total weight of the composition.

According to any of the above embodiments, the inventive composition may further comprise an extract of huangbai in an amount of 10–90% by weight based on the total weight of the composition, wherein the amount of huangqin is 2–60% by weight based on the total weight of the oil.

Optionally, the inventive composition may further comprise obabenine, preferably at a concentration ranging from about 0.001% to 2% by weight, more preferably about 0.002% to 0.5% by weight, and most preferably about 0.003% to 0.1% by weight.

According to any of the above embodiments, the inventive composition may further comprise an extract of huanglian in an amount of 10–90% by weight based on the total weight of the composition, wherein the amount of huangqin is 2–60% by weight based on the total weight of the oil.

Also optionally, the inventive composition may further comprise berberine, preferably at a concentration ranging from about 0.001% to 2% by weight, more preferably about 0.002% to 0.5% by weight, and most preferably about 0.003% to 0.1% by weight.

Also optionally, the inventive composition may further comprise narcotoline, preferably at a concentration ranging from about 0.001% to 2% by weight, more preferably about 0.002% to 0.5% by weight, and most preferably about 0.003% to 0.1% by weight.

In a particular embodiment, the inventive composition further comprises an extract of huangqin in the oil containing baicalin at a concentration ranging from about 0.001 to 2% by weight based on the total weight of the oil, wherein the sterol compound is a phytosterol and the oil is sesame oil.

Also optionally, the inventive composition may further comprise an extract of heshouwu in the oil, preferably in an amount of 10–90% by weight based on the total weight of the composition, wherein the amount of heshouwu is 2–60% by weight based on the total weight of the oil.

Also optionally, the inventive composition may further comprise various amino acids, preferably all 20 natural amino acids (e.g., alanine, asparagines, aspartic acid, cysteine, glutamic acid, glutamine, glycine, phenylalanine, histidine, isoleucine, lysine, leucine, methionine, proline, arginine, serine, threonine, valine, tryptophan, and tyrosine), for providing nutrition support to cell growth. The amino acids may be chemically synthesized or obtained from natural sources. For example, a full spectrum of natural amino acids may be obtained by extracting earthworms, a rich source of protein/amino acids, in oil or alcohol.

In a particular embodiment, the inventive composition further comprises an extract of earthworm in an amount of 10–90% by weight based on the total weight of the composition, wherein the amount of earthworm is 2–60% by weight based on the total weight of the oil.

In another aspect of the invention, a method of repairing a damaged tissue or an organ is provided. The method comprises: administering to a mammal having a damaged or diseased tissue or organ a pharmaceutically acceptable composition comprising a sterol compound dissolved in oil at a concentration at least 0.5% by weight, such that the physiological structure and function of the tissue or organ are substantially restored.

In one embodiment, a method is provided for treating a wound of the skin, bone, mucus, tendons, muscles or connective tissue in a mammal, preferably a human. The method comprises: administering in vivo to said mammal at the site of the wound a composition comprising a fatty acid-containing oil at a concentration at least 10% by weight based on the total weight of the composition; and a sterol compound added to and dissolved in said oil at a concentration at least 1% by weight based on the total weight of the composition. The concentration of the sterol compound preferably ranges from about 1.2% to 40% by weight, more preferably about 1.2% to 20% by weight, and most preferably about 2% to 6% by weight based on the total weight of the composition. The pharmaceutically acceptable composition may be any of the inventive compositions described above.

The method may further comprise: liquefying a necrotic tissue of the wound; and removing the liquefied necrotic tissues from the wound site without surgical debridement.

The method may be used to treat acute wounds such as a wound resulted from physical trauma, thermal, wind, frost, optical or electric injury.

The method may also be used to treat chronic wounds such as chronic surface ulcer, diabetic ulcer, decubital ulcer, chronic wound as a result of a lower limb vascular disease, chronic wound as a result of poor blood flow, wound due to cancer or cancer metastasis, erosion caused by bacterial or viral infection, herpes simplex corneal ulcer, subcutaneous tissue ulcer, radiation-caused skin ulcer, vaginitis, cervical erosion, gingivitis, wounds due to dilation and enlargement of veins, and hemorrhoid.

For a chronic wound, the method may further comprise: debriding the chronic wound before administering the composition to the wound. The debridement may include surgically removing necrotic tissues from the wound or chemically removing necrotic tissues from the wound, while avoiding injury to the viable tissue surrounding the wound site.

According to the method, the composition may be administered topically to the wound, for example, at least three times a day in a sufficient amount to such that the wound site is maintained moist. The moist level is preferably maintained between 1–5 folds of the physiological moist level of a normal human body. Optionally, the composition is in a form of ointment and is administered in a sufficient amount to cover the wound at a thickness of 0.5–5 mm of the ointment, preferably a thickness of 1–3 mm of the ointment.

Also according to the method, the composition may further comprise beeswax, preferably at a concentration ranging from about 1% to 20% by weight based on the total weight of the composition. The beeswax in the composition forms a pigeon-hole like structure at ambient temperature or below to allow effective debridement of necrotic tissues without causing substantial damages to the viable tissues immediately adjacent to the wound site and/or a timed delivery of active ingredients in the composition to the wound.

The dimension of at least 50% of the holes in the pigeon-hole like structure is preferably below 50 micron, more preferably below 20 micron, and most preferably between about 10–50 micron.

Also according to the method, the composition may further comprise baicalin or an extract of huangqin in an amount of 10–90% by weight based on the total weight of the composition, wherein the amount of huangqin is 2–60% by weight based on the total weight of the oil.

In another embodiment, a method is provided for cultivating stem cells in vivo and in situ, for example, at the site of a dysfunctional tissue or organ of an adult mammal, preferably an adult human (i.e., a non-fetus). The method comprises:

administering in vivo to said mammal at the site of the dysfunctional tissue or organ a composition comprising a fatty acid-containing oil at a concentration at least 10% by weight based on the total weight of the composition; and a sterol compound added to and dissolved in said oil at a concentration at least 1% by weight based on the total weight of the composition; and cultivating endogenous stem cells from the mammal at the site of the dysfunctional tissue such that the stem cells are viable for at least 1 day at the site.

According to the method, the stem cells may be adult stem cells existing before the dysfunction of the tissue or organ, or adult stem cells generated after the administration of the composition.

Optionally, the stem cells may be fetal stem cells generated by an adult mammal after the administration of the composition. For example, if the dysfunctional organ is a skin injured to its full thickness for example as a result of physical trauma or thermal injury, the stem cells may include epidermal stem cells expressing keratin-19.

Also optionally, if the dysfunctional organ is an injured muscle, tendon or connective tissue, the stem cells may include epidermal stem cells expressing keratin-19.

The method may further comprise: drilling one or more holes in a bone adjacent to the injured connective tissue to release bone marrow, wherein cells from the bone marrow are cultivated in the presence of the composition to become epidermal stem cells expressing keratin-19.

According to the method, the dysfunctional tissue or organ may be a wound tissue or organ resulted from physical trauma, thermal, wind, frost, optical or electric injury. Alternatively, the dysfunctional tissue or organ is due to a chronic wound selected from the group consisting of chronic surface ulcer, diabetic ulcer, decubital ulcer, chronic wound as a result of a lower limb vascular disease, chronic wound as a result of poor blood flow, wound due to cancer or cancer metastasis, erosion caused by bacterial or viral infection, herpes simplex corneal ulcer, subcutaneous tissue ulcer, radiation-caused skin ulcer, vaginitis, cervical erosion, gingivitis, wounds due to dilation and enlargement of veins, and hemorrhoid.

By using the method, physiologically functional tissues and organs such as blood vessels, nerves, and skin at the site of the injured tissue can be regenerated via cultivation of the adult mammal's own stem cells in vivo and in situ.

In yet another embodiment, a non-invasive method for debriding a necrotic tissue in a mammal, preferably a human, is provided. The method comprises:

administering in vivo to said mammal at the site of the necrotic tissue a composition comprising a fatty acid-containing oil at a concentration at least 10% by weight based on the total weight of the composition;

a sterol compound added to and dissolved in said oil at a concentration at least 1% by weight based on the total weight of the composition; and a wax at a concentration at least 1–20% by weight based on the total weight of the composition, wherein the wax in the composition forms a pigeon-hole like structure at ambient temperature or below;

liquefying at least 20% of the necrotic tissue; and removing the liquefied necrotic tissues from the mammal without surgical debridement.

According to the method, the necrotic tissue may be liquefied without substantially damaging the viable tissues in the mammal. Preferably, at least 80% of the viable tissues immediately adjacent to the necrotic tissue is still viable after liquefaction of the necrotic tissue. More preferably, at least 90% of the viable tissues immediately adjacent to the necrotic tissue is still viable after liquefaction of the necrotic tissue.

Also according to the method, the step of liquefying the necrotic tissue may include:

enclosing granules of the necrotic tissue with the oil, wherein the enclosed necrotic tissue undergoes hydrolysis of the cells therein to release enzymes to digest the necrotic tissue, and randicity and saponification between the digested tissue and the oil, resulting in liquefaction of the necrotic tissue; and discharging the liquefied necrotic tissue without substantially reducing viability of the viable tissues immediate adjacent to the necrotic tissue.

The method may further comprise: removing the liquefied necrotic tissue such as absorbing the liquefied tissue by using an absorbent material such as tissue paper or cloth.

Also according to the method, the wax is preferably an edible wax such as beeswax, castorwax, glycowax, and carnaubawax. The dimension of at least 50% of the holes in the pigeon-hole like structure is preferably below 50 micron, more preferably below 20 micron, and most preferably between about 10–50 micron.

Also according to the method, the composition is administered in a sufficient amount such that the site of the necrotic tissue is maintained moist. The moist level is preferably maintained between 1–5 folds of the physiological moist level of a normal human body. Optionally, the composition is in a form of ointment and is administered in a sufficient amount to cover the wound at a thickness of 0.5–5 mm of the ointment, preferably a thickness of 1–3 mm of the ointment.

The necrotic tissue may be one existing in an acute wound such as a wound resulted from physical trauma, thermal, wind, frost, optical or electric injury, or a chronic wound such as chronic surface ulcer, diabetic ulcer, decubital ulcer, chronic wound as a result of a lower limb vascular disease, chronic wound as a result of poor blood flow, wound due to cancer or cancer metastasis, erosion caused by bacterial or viral infection, herpes simplex corneal ulcer, subcutaneous tissue ulcer, radiation-caused skin ulcer, vaginitis, cervical erosion, gingivitis, wounds due to dilation and enlargement of veins, and hemorrhoid.

In yet another embodiment, a method is provided for controlling microbial infection in the skin or mocusal tissue of a mammal, preferably a human. The method comprises:

administering in vivo to said mammal at the site suspected of infection a composition comprising a fatty acid-containing oil at a concentration at least 10% by weight based on the total weight of the composition; and a sterol compound added to and dissolved in said oil at a concentration at least 1% by weight based on the total weight of the composition.

According to the method, the sterol compound may be esterified by the fatty acid in the oil in the composition. The concentration of the sterol compound is preferably 1.2–40% by weight, more preferably about 1.2–20% by weight, and most preferably 2–6% by weight.

The sterol compound is preferably a phytosterol. Examples of the phytosterol compound include, but are not limited to, stigmasterol, campesterol, β-sitosterol, chalinosterol, clionasterol, brassicasterol, α-spinasterol, daucosterol, desmosterol, avenasterol, cycloartenol, poriferasterol, and natural or synthesized, isomeric forms and derivatives thereof. In particular, the sterol compound is more preferably a combination of stigmasterol and β-sitosterol, a combination of brassicasterol and β-sitosterol, a combination of brassicasterol, stigmasterol and β-sitosterol, or a combination of campesterol, stigmasterol and β-sitosterol.

Also according to the method, the microrobial infection may be infection of bacteria, fungus, virus, or a combination thereof. Specific examples of bacteria include, but are not limited to, *Bacilius tetani, Bacteroides fragilis, Propionibacterium acne, Candida albicans, Bacillus proteus, E. coli,* or *Pseudomonas aeruginosa*. Preferably, the composition is administered in a sufficient amount such that the cell wall of the bacteria is substantially intact.

In yet another aspect of the invention, a method is provided for culturing stem cells in vitro. The method comprises:

contacting a culture of stem cells with a composition comprising a fatty acid-containing oil at a concentration at least 10% by weight based on the total weight of the composition; and a sterol compound added to and dissolved in said oil at a concentration at least 1% by weight based on the total weight of the composition.

The method may further comprise: removing waste in the cell culture after at least 1 day of culturing in the presence of the composition; and adding the composition to the culture again to maintain the growth of the stem cells.

According to the method, the stem cells may be included in one or more tissue pieces (e.g., skin pieces) immersed in the culture. The tissue may be isolated from an adult or fetal mammal, or from human foreskin.

Optionally, the stem cells may be embryonic stem cells of a vertebrate, preferably a mammal, and more preferably a human.

Also according to the method, the composition may further comprise baicalin, preferably at a concentration ranging from about 0.001 to 2% by weight based on the total weight of the composition, or an extract of huangqin huangqin in an amount of 10–90% by weight based on the total weight of the composition, wherein the amount of huangqin is 2–60% by weight based on the total weight of the oil.

In yet another aspect of the invention, a method is provided for manufacturing a composition for promoting cell growth, tissue repair and/or organ regeneration in vivo. The method comprises:

a) heating a mixture of an fatty acid-containing oil and huangqin at a weight ratio between 70:30 and 98:2 at a temperature between 150–190° C. for 30–120 min;

b) filtering the mixture to obtain an oil filtrate;

c) cooling the oil filtrate to below 150° C.;

d) mixing a sterol compound with the oil filtrate of step b) at a weight ratio between 1:99–20:80;

e) heating the mixture of step d) with stirring at a temperature between 100–150° C. for 20–60 min; and f) cooling the mixture of step e) to obtain the composition.

According to the method, the fatty acid-containing oil is preferably a vegetable oil such as corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof.

Also according to the method, the sterol compound is preferably a phytosterol such as stigmasterol, campesterol, β-sitosterol, chalinosterol, clionasterol, brassicasterol, α-spinasterol, daucosterol, desmosterol, avenasterol, cycloartenol, poriferasterol, and natural or synthesized, isomeric forms and derivatives thereof. In particular, the sterol compound is more preferably a combination of stigmasterol and β-sitosterol, a combination of brassicasterol and β-sitosterol, a combination of brassicasterol, stigmasterol and β-sitosterol, or a combination of campesterol, stigmasterol and β-sitosterol.

The method may further comprise:

g) mixing beeswax with the mixture of step d) at a weight ratio between 1:99–20:80 at a temperature of 100–150° C.; and h) heating the mixture of step g) with stirring at a temperature between 100–150° C. for 10–60 min.

According to the method, the mixture of step a) may further comprise huangbai, earthworm, rice capsule, huanglian, or a combination thereof, each at a weight between 1:99–30:70.

In yet another aspect of the invention, a method is provided for preparing a stable and non-toxic formulation suitable for parenteral administration to an animal. This method involves thoroughly mixing a clinically accepted fatty emulsion having an oil phase with an amount of the sterol compound sufficient to result in a formulation at the concentration ranging from about 0.1% to 20% by weight, preferably from about 0.2% to 15%, more preferably from about 1% to 10%, and most preferably about 3% to 6%. The thorough mixing may be accomplished by many means well-known in the field and may, for example, involve sonication or repeated passage through a small orifice such as that of a syringe needle.

The inventive compositions described above may be administered or coadministered orally, topically, parenterally, intraperitoneally, intravenously, intraarterially, transdermally, sublingually, intramuscularly, rectally, transbuccally, intranasally, via inhalation, vaginally, intraoccularly, via local delivery (for example by catheter or stent), subcutaneously, intraadiposally, intraarticularly, or intrathecally.

In a preferred embodiment, the inventive composition is administered locally to a site where the damaged or diseased tissue/organ is located via various routes of administration, such as transdermally, intramuscularly, by catheter or stent, intraperitoneally, intraarterially and vaginally. The inventive composition may also be administered or coadministered in slow release dosage forms.

In a more preferred embodiment, the inventive composition is administered directly and locally to the tissues of the diseased or damaged organ. For example, the inventive composition comprising sterol dissolved in injectable oil may be directly injected into heart muscles and be directly taken up by the cells of these tissues without going through blood vessels.

Alternatively, other delivery systems for hydrophobic pharmaceutical compounds may be employed to deliver the inventive composition. Liposomes and emulsions are well known examples of delivery vehicles or carriers for hydrophobic drugs. In a preferred embodiment, long-circulating, i.e., stealth liposomes are employed. Optionally, the inventive composition may be administered in a targeted drug delivery system, for example, in a liposome coated with an antibody targeting the tissue/organ to be repaired or regenerated, such as a tumor-specific antibody. Such liposomes will be targeted to and taken up selectively by the site of interest (e.g., tumor cell).

Also optionally, the inventive composition may be delivered using a sustained-release system, such as semipermeable matrices of solid hydrophobic polymers containing the therapeutic agent.

Via various routes of administration in vivo and in vitro, the inventive compositions and methods described above have a wide variety of applications in biology and medicine.

It should be noted the inventive compositions may be adapted for use in vitro as cell growth culture media or in ex vivo reconstruction of tissues and/or organs.

Morphologically, the inventive compositions and methods may be used to activate dormant adult stem cells (ASCs) or to induce transformation of adult tissue cells into ASCs in vivo, as well as in vitro. Further, these inventive compositions may be used to induce tissue-specific morphogenesis of cells to render morphological changes of the cells, which may lead to dedifferentiation of cells, i.e., reversion of a differentiated cell to a non-differentiated cell (stem cell). In addition, they can also be used to inhibit toxicity of bacteria, presumably through modulation the structure and function of the bacterial membrane and alteration of the bacterial cell cycle.

Intracellularly, the inventive compositions may be used to activate various enzymes such as kinases and phosphatases and signaling molecules such as cAMP which play important roles in cell growth and differentiation, and thus support the growth of cells and maintain the balance of various types of cells to ensure repair and regeneration of physiologically functional tissues and organs.

Intercellularly, the inventive compositions may be used to promote tissue-specific association of cells of the same or different type, presumably through stimulation of expression and activation of various cell adhesion molecules (CAM) such as connexin and cadherin to form various physiological junctions.

At the tissue level, the inventive compositions may be used to promote organ-specific assembly of tissues by promoting formation of physiological junctions between these tissues.

In human and veterinary medicine, the inventive compositions may be used in the treatment of various conditions caused by injury, diseases and aging. As shown clinically, the methodology disclosed in the present invention was used to regenerate or clone a new organ through cultivation of regenerative stem cells in vivo and in situ.

BRIEF DESCRIPTION OF THE FIGURES

FIG. 3A shows gastric ulcer of an animal model.

FIG. 3B shows gastric ulcer of an animal model that has been cured by using an embodiment of the inventive composition.

FIG. 4A shows the scalp of a human suffering from baldness.

FIG. 4B shows regrowth of hair on the scalp of the human shown in FIG. 4A after topical application of an embodiment of the inventive composition to the scalp.

FIGS. 5A–C show changes in the cells and tissues in a wound caused by second degree burn on day 1, 6, and 10 post injury, respectively, in the presence of an embodiment of the inventive composition.

FIG. 10A shows morphology of fibroblasts growing in a regular cell culture in vitro.

FIG. 10B shows morphology of fibroblasts growing in a cell culture in vitro in the presence of an embodiment of the inventive composition.

FIGS. 15A–D show the results of the in vitro experiments on mouse skin cell culture in the presence (left column) and absence (right column) of the inventive composition on day 10, 30, 49, and 70 of culturing, respectively.

FIGS. 16A–C show the results of the in vitro experiments on rat hair follicle stem cell culture in the presence (left column) and absence (right column) of the inventive composition.

FIGS. 17A-C show the results of the in vitro experiments on mouse skin tissue culture in the presence (left column) and absence (right column) of the inventive composition.

FIG. 20A shows that in the normal epidermis of this patient, few cells are K-19 positive.

FIG. 20B shows that for skin in the wounds, there was a moderate amount of regenerative epidermal stem cells which were stained positive for K-19 24 hr post burn.

FIGS. 20C–F show dynamic changes in the level of K-19 positive stem cells on day 4, 7, 14, and 21 post burn, respectively.

FIG. 27A shows an immunohistochemical analysis of the section stained with $AE_3$ revealing positive protein of squamous epithelium, indicating spontaneous self-regeneration of the skin.

FIG. 27B shows that the section stained with $AE_1$ showed negative protein of glandular epithelium.

FIGS. 33A–B show that tissue stem cells from their cognate organ associate with each other in an organ-specific manner.

FIG. 50A shows that the burn wound of a rabbit treated with the inventive composition was moist.

FIG. 50B shows that the burn wound of a rabbit treated with Vaseline is drenched, showing signs of dislodging of tissues; and the normal skin surround the wound also suffered excessive drenching.

FIG. 51A shows that for the wound treated by the dry therapy there was infiltration of inflammatory cells between the necrotic tissues and the viable tissues.

FIG. 51B shows that for the wound treated by the inventive composition there was only mild infiltration of inflammatory cells in the junction between the necrotic tissues and the viable, and slight dilation and congestion of micro blood vessels.

FIG. 51C shows that In the wound treated by Vaseline tissue vacuolation and infiltration of inflammatory cells at 48 hours post burn.

FIG. 52 shows that the wound healing time of the rabbits treated by the inventive composition was much faster (15 days) than the control without any treatment (20 days).

FIG. 53A shows the normal morphology of *Bacilius tetani* cells adopting a slender rod-like shape.

FIG. 53B shows that the 1–2 generation of *Bacilius tetani* cells cultured in the medium containing the inventive composition adopted a long rod or filament shape.

FIG. 53C shows that the 3–4 generation of *Bacilius tetani* cells showed greater variation in length, many having spores of drumstick shape (indicated by arrows), and a few long rod or filament shape.

Figure 1:
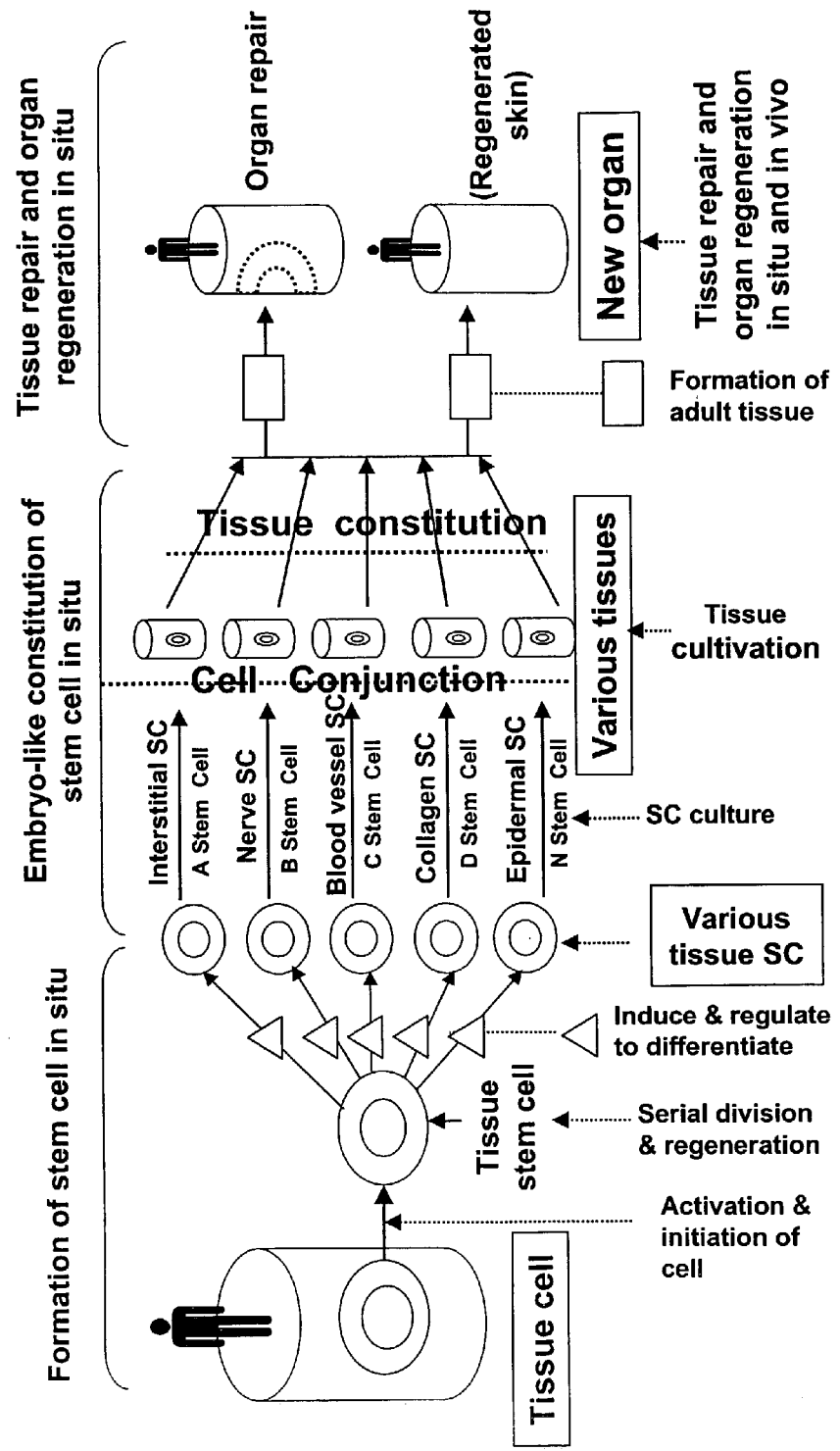
FIG. 1 is a diagram depicting a plausible mechanism by which tissues and/or organs are repaired or regenerated via cultivation of stem cells in vivo and in situ by using the inventive methodology.

FIG. 54A shows the normal morphology of *Bacteroides fragilis* cells with a moderate size.

FIG. 54B shows that the 3–4 generation of *Bacteroides fragilis* cells cultured in the medium containing the inventive composition had various lengths and the colonies fused together.

FIG. 54C shows that the 5–6 generation of *Bacteroides fragilis* cells adopted a sphere or egg shape and many colonies fused to from irregular spheres.

FIG. 55A shows the normal morphology of *Propionibacterium acne* cells adopting a slend, short rod shape.

FIG. 55B shows that the 3–4 generation of *Propionibacterium acne* cells cultured in the medium containing the inventive composition adopted various longer, bulkier rod or filament shapes.

FIG. 56A shows the normal morphology of *Candida albicans* cells in egg shape and with many blastospores.

FIG. 56B shows that the 3–4 generation of *Candida albicans* cells cultured in the medium containing the inventive composition adopted a rounder shape in various sizes and there were some stick-shaped fungi with few blastospores observed.

FIG. 56C shows that the 5–6 generation of *Candida albicans* cells adopted a stick or long rod shape and bacterial filaments had various lengths and few blastospores were observed.

FIG. 56D shows that normal *Candida albicans* cells produced germ tubes at a rate of 90%.

FIG. 56E shows that the germ tube production rate of the 5–6 generation of *Candida albicans* cells grown in a culture medium containing the inventive composition was only 0.5–2%.

FIG. 57A shows the normal morphology of *Propionibacterium acne* cells adopting a slend, short rod shape.

FIG. 57B shows that the 1–2 generation of *Bacillus proteus* cells cultured in the medium containing the inventive composition adopted a much longer, bulkier rod or filament shape.

FIG. 58A shows the normal morphology of *E. coli* cells adopting a short rod shape.

FIG. 58B shows that the 5–6 generation of *E. coli* cells cultured in the medium containing the inventive composition adopted a much longer, bulkier rod or filament shape.

FIG. 59A shows the normal morphology of *Pseudomonas aeruginosa* cells adopting a short rod shape.

FIG. 59B shows that the 5–6 generation of *Pseudomonas aeruginosa* cells cultured in the medium containing the inventive composition adopted various longer rod or filament shapes.

FIG. 60 shows that the control cell culture had high activity of the enzyme and the liquid was clear with many large bacteria clots.

FIG. 61 shows that enzymatic activity of the cells growing in the medium containing the inventive composition was gradually reduced in a dosage dependent manner.

FIG. 62 shows that after the 10$^{th}$ generation of *Staphylococcus aureus* and *Pseudomonas* there was about 20–30 reduction in the total number of bacteria.

DETAILED DESCRIPTION OF THE INVENTION

The present invention provides novel methods and compositions for physiological tissue repair and functional organ regeneration of animals, in particular, humans. The groundbreaking innovation is multi-facet in both the conceptual and practical aspects, with a primary focus on the techniques for tissue repair and organ regeneration through induction and propagation of regenerative stem cells in situ and in vivo.

Using skin—the largest organ of the body as a model, the inventor has demonstrated clinically that damaged or lost human tissue and organ can be regenerated in situ, i.e., where it originally resides in the body. For example, patients with extensive, deep burns where large areas of skin were severely injured and dysfunctional were able to recover with scarless wound healing and restoration of normal functions of the skin, including those of the appendages.

In contrast, the current approach taken by people in the field of tissue repair and organ regeneration focuses primarily on transplantation of tissue engineered ex vivo, i.e., outside the human body. As reviewed in the Background section of this invention, extensive efforts have been made to engineer autologous and allogenic tissue from human or other animals in order to transplant them into the human body to repair or replace dysfunctional organs. Moderate successes have been achieved using this approach, with serious limitations on clinical efficacy and cost in materials and labor. More significantly, so far there has been no clinical evidence demonstrating regeneration of organ with a complete restoration of physiological functions by using this approach. For example, patients with extensive, deep burns still recover with disfigurement riddled with scars and disablement due to complete or partial loss of the skin functions.

The inventor believes that using the methodology and compositions provided by the present invention, a fully functional organ can be regenerated for the first time with human intervention. Various tissues constituting the organ can be regenerated or repaired physiologically, i.e., with a complete restoration of their physiological structures and functions. By contrast, wounds that are treated by using other approaches, often if not most of the time, heal pathologically, i.e., with abnormal or impaired functions of the skin. Observed macroscopically, such a dysfunction manifests as scars; and microscopically alternations of skin texture, color, vascularity, nerve supply, reflectance and biochemical properties.

1. The Fundamental Principle of Adult Tissue Repair and Organ Regeneration

The present invention reveals the fundamental principle of adult tissue repair and regeneration in vivo and in situ, which is illustrated in FIG. 1.

1) The Principle in General

In general, an adult, fully developed body has the ability to repair its damaged tissue and regenerate its organ in situ if the regenerative environment is provided. As illustrated in FIG. 1, in response to wound or other kinds of injury residual viable cells in the damaged organ can be activated and convert themselves into adult stem cells (ASCs), the counterpart of which are embryonic stem cells. Such induction of adult stem cells makes it possible that a large amount and a wide variety of cells needed for organ regeneration may be provided by these stem cells.

However, these nascent stem cells are quite fragile and are prone to death caused by cytotoxic effects exerted by various environmental elements, and by uncontrolled cellular responses to injury. As illustrated in FIG. 1, under suitable culturing conditions provided by the inventive compositions these adult stem cells proliferate and develop into various multipotent tissue stem cells by following the directions which are already genetically programmed at the embryonic development stages. Generation of such a multiple functional tissue stem cell assures ample supply of various types of cells that are needed for forming a physiologically functional tissue.

Still referring to FIG. 1, under optimum culturing conditions provided by the inventive compositions these tissue stem cells proliferate and differentiate into specific types of cells for particular kinds of tissues. Specific types of differentiated cells associate with each other through tissue-specific cell adhesion and form a nascent tissue. Such modes of tissue-specific cell association are collectively referred to herein as "cell conjunction". The newly regenerated tissues then assemble into a nascent organ by forming organ-specific tissue-tissue junctions, mimicking the tissue assembly process in a developing fetus. Such a mode of organ specific tissue association in an adult is collectively referred to herein as "tissue constitution".

Finally, the nascent tissues within the reconstituted organ develop and mature into individual, functional tissues with physiologically balanced cell types and numbers under the regulation of inventive composition. Meanwhile, these tissues undergo further remodeling through communications of tissues within the network of the live organ and eventually form a fully functional, mature organ (FIG. 1).

By following the above-described regenerative pathways, damaged or lost tissues can be repaired to regain their physiological structure and function. As demonstrated in the Example section using human skin as a model, patients with severed damaged skin were treated with the inventive methodology without suffering through skin grafting and could recover with a completely new skin without loss of physiological structure and function of the skin, including various appendages of the skin.

The inventor believes that by in situ cultivation of regenerative stem cells within a live body under an optimum developmental condition, the damaged organ can be regenerated with a complete restoration of its physiological structures and functions. This regeneration process takes place spontaneously within the body under the regulation of both endogenous and exogenous materials provided in the present invention. Ultimately, successful organ regeneration depends on physiologically proper tissue-specific multi-cell adhesion, organ-specific multi-tissue assembly, and homeostatically balanced and immunologically compatible coexistence of multi-organs within a live body.

2) Redefinition of "Stem Cells"

Based on this fundamental principle and its successful application in organ regeneration in the clinic, the meaning of a stem cell is redefined in the present invention.

A classic definition of a stem cell is that a stem cell should have the following properties: 1) It is not itself terminally differentiated, i.e., not at the end of a pathway of diffentiation; 2) It can divide without limit or at least for the life time of the animal; and 3) When it divides, each daughter cell can either remain a stem cell, or embark on a course leading irreversibly to terminal differentiation. In Molecular Biology of the Cell, Alberts et al., eds, $3^{rd}$ ed. (1994), pp. 1155–1156, Garland Publishing Inc., New York and London.

According to this definition, stem cells isolated from human tissue, such as the embryonic stem cells isolated from the inner cell mass of human blastocysts, are still stem cells even if they are completely isolated from a live human body and reside in culture medium in vitro. These so-called stem cells, although capable of divide without limit and differentiate into cells of various tissue types, have not been shown to be able to regenerate a fully functional human organ, let alone a live human in vitro.

To avoid confusion with the stem cells termed under the classic definition, the stem cell according to the present invention is termed as a "regenerative stem cell". This regenerative stem cell has the following characteristics: 1) it resides in a live body; 2) it is under the physiological control and regulation of the body; 3) it co-exists with the tissues and organs of the body, 4) it is capable of continuous cell division within the live body; 5) it is capable of repairing tissues, regenerating organs, and restoring physiological structures and functions to the regenerated organs.

3) Spontaneous Regeneration in the Body

The human body has considerable capacity for regeneration. Tissues with high rates of cell turnover, such as blood and epithelia, are regenerated continually through out life. Other Tissues, such as liver, bone, muscle, blood vessels, and adrenal cortex regenerate in response to injure. The liver regenerates by compensatory hyperplasia, whereas other tissues regenerate by the activation of reserve stem or progenitor cells perhaps by augmenting the regeneration of mesenchymally-derived tissues, or within the regenerating tissue. For example, hematopoietic cells such as T cells, B cells, neurotrophil, and erythrocytes are regenerated from hematopoietic stem cells in the bone marrow. Finger tips will regenerate if amputated distal to the terminal phalangeal joint. However, neither bone nor muscle will regenerate across a gap, and other organs as skin, pancreas, heart, and spinal cord respond to injury by the formation of scar tissue.

The distinct, novel approach disclosed in the present invention focuses on harnessing the body's inherent ability to repair and regenerate itself. Under optimum physiological conditions, such as bathing in the warm, sterile amniotic fluid, a fetus could heal its wound spontaneously without scar and loss of function. Unfortunately, a fully developed human is exposed to a completely different, more hostile environment. Under the influence of both endogenous and exogenous conditions, spontaneous adult wound healing and organ generation go through somewhat different pathways and end up with scars and dysfunction of organs. This spontaneous healing process is totally passive, uncontrolled by therapeutic interventions by embarking on a course of chaotic cell proliferation and differentiation and reconstitution of regenerated tissues.

4) Methodology Developed in Application of the Principle

The present invention provides methods and compositions to actively control the whole process of tissue repair and organ regeneration. During this process, cells, the smallest unit of life, are stimulated, propagate, differentiate, integrate with each other to physiologically repair the damaged tissues or to regenerate the tissue destroyed in various courses, such as trauma and diseases. These nascent tissues then conjoin together to form a fully functional organ.

To achieve this result in an adult, specific, active human intervention is needed. The general guidance for this intervention revealed in the present invention is that 1) for injured or damaged tissues, the viable cells in the remaining tissues should be preserved to a maximum extent; 2) necrotic cells or tissues should be removed as early as possible; 3) the regenerative cells should be activated and propagated in an environment mimicking the their own native physiological conditions; and 4) regulators for cell growth and differentiation are administered to the regenerating organ to direct proper, physiological repair of tissues.

Figure 2:
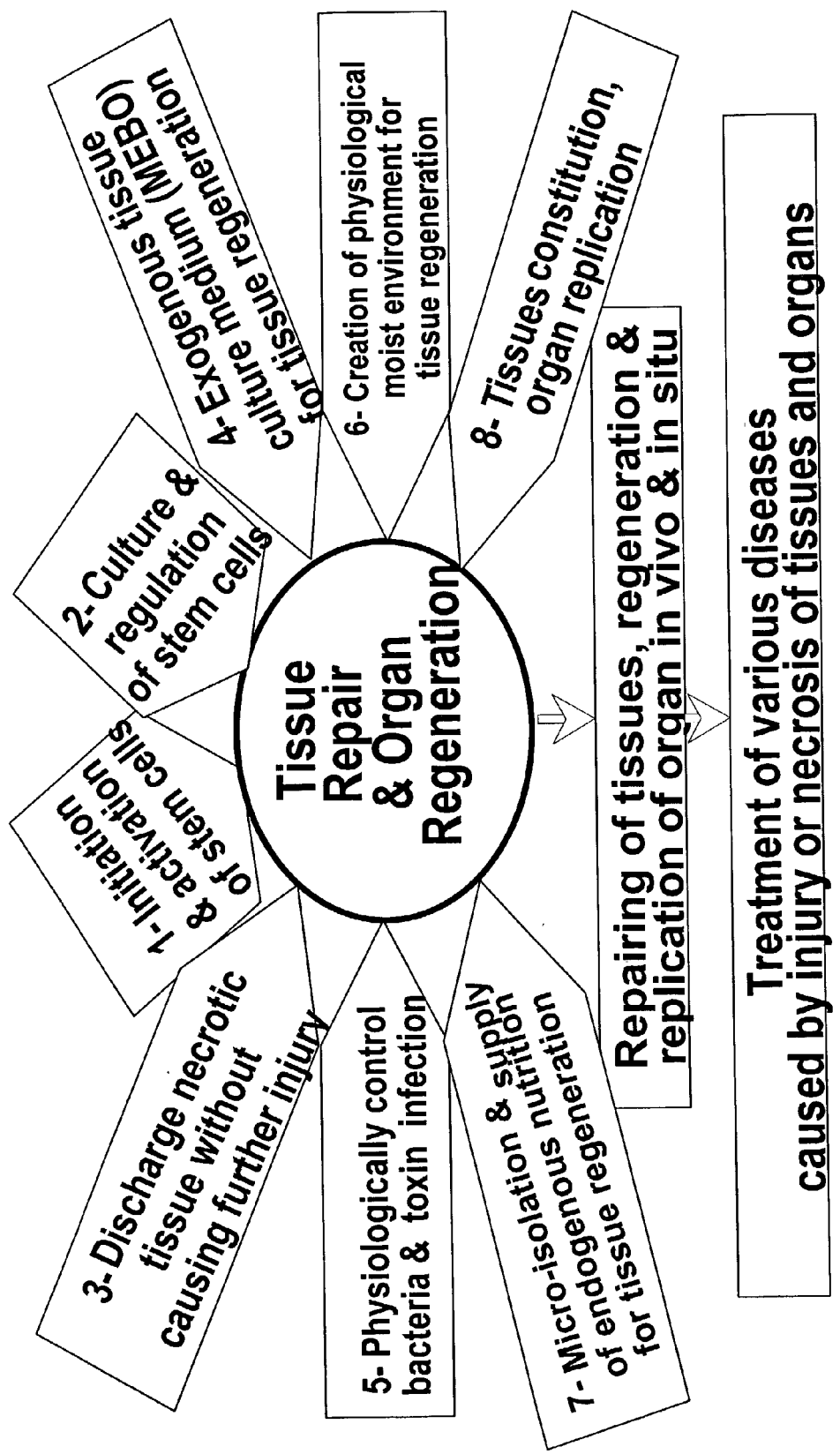
FIG. 2 is a diagram depicting various techniques that may be used to promote physiological tissue repair and organ regeneration according to the present invention.

Specifically, the methodology of the present invention covers the following eight techniques as illustrated by a block diagram in FIG. 2:

a) Activation and Regulation of Adult Stem Cells (ASCs)

Multipotent adult stem cells are produced in vivo and in situ by i) activating dormant tissue stem cells such as epithelial stem cells putatively residing in the bulge of a hair follicle, and/or ii) inducing dedifferentiation of fully dedifferentiated cells and converting them into ASCs.

b) Culture of ASCs In Vivo and In Situ

The fragile, nascent ASCs are cultured in a physiologically moist environment to allow rapid growth and directionally differentiation;

c) Discharge or Exudation of Liquefied Necrotic Tissues

Necrotic tissues of the wounded skin are removed without using a traditional method of debridement involving invasive surgical excision; the necrotic tissues are liquefied by an inventive composition from outside-in and exudate from the wound automatically, thus greatly reducing the risk of physical or chemical injury to residual viable tissue;

d) Tissue Culturing In Vivo and In Situ in an Exogenous Culture Medium

ASCs and their differentiated cells are cultured in an exogenous culture medium provided by the present invention to allow rapid cell growth, integration and migration to physiologically repair the damaged tissue or regenerate lost tissue;

e) Inhibition of Toxicity of Bacteria by a Non-Bactericidal Mode of Action

Toxicity of bacteria infecting the wound are inhibited not by topically applying antibiotics to kill the bacterial cells, rather by allowing a bacterial cell to replicate genetically and change its morphology under a condition provided by an inventive composition, leading to reduced production of toxin; and thus greatly reduce inflammation caused by the body's immune response to bacterial toxin.

f) Creation of Physiologically Moist Environment for Skin Regeneration

Excessive drying of the wound leads to eschar formation and damages viable tissues. Moisture evaporation of the wound is prevented by using an inventive composition but not causing excessive drench of the wound as compared with the effects of Vaseline as wound dressing.

g) Micro-Isolation of Wound from Exterior Environment

Application of an inventive composition to the wound results in formation of an opaque membrane which isolates the wound from the exterior environment and yet allows permeation of nutrients and oxygen to the tissues beneath. This semi-permeable membrane may mimic the amniotic membrane enclosed within which is a relatively sterile environment for regeneration of tissues enclosed. As a result, tissues are regenerated and reconstitute to form a fully functional organ following an embryonic development-like scheme.

h) Supply of Oxygen and Nutrition Required for Regeneration

Various nutrients such as a full spectrum of natural amino acids, polysaccharides, fatty acids and phosphates are supplied exogenously. Oxygen required for cell growth can permeate through this membrane to reach the tissues beneath. Meanwhile, bacteria and other environmental contaminates are separated from the tissues undergoing wound healing.

5) Comparison of the Present Methodology with Other Approaches in the Art

Clinical approaches currently available to replace failing organs and tissues are organ transplantation and implantation of bionic device. The major drawbacks to organ transplantation are donor shortages and immunosuppressive side effects. The drawback to the approach of implantation of bionic device is the inability to manufacture artificial materials that duplicate the durability, strength, form, function, and biocompatibility of natural tissues.

At the experimental stage, regenerative medicine emerged in the last decade of the $20^{th}$ century has been focussed on implemenation of two major strategies: transplantation of cells to form a new tissue in the transplant site and implantation of bioartificial tissues constructed in vitro.

Transplantation of cells involves ex vivo culturing and propagation of stem cells and then transplanting them or their differentiated products to the site where the damaged organ resides. Although progress in biology has made it possible for apply the cell transplantation in the clinic, multiple practical limitations still exist and the clinical results are not physiological or cosmetically satisfactory. One of the limitations associated with this approach is the difficulties with identification and isolation of multipotent stem cells from various tissues. Although pluriopotent human embryonic stem cell (ESC) lines have been cultured recently, directional differentiation of the ESCs remains a mystery.

Results obtained from experimental animals, although encouraging, still cannot translate functionally into human therapy confidently. For example, mouse neuronal and glial cells derived from neural stem cells in vitro, and cardiomyocytes derived from ESCs in vitro, integrate into the surrounding tissue when injected into an adult brain and heart, respectively. Multipotent human neural stem cells injected into the developing brain of mouse embryos migrate throughout the brain and differentiate site-specifically.

For successful organ regeneration using stem cells cultured in vitro, major obstacles lies in its way. Stem cells cultured in vitro must be directed to differentiate into site-specific phenotypes once they are transplanted into the lesion site. Complete deciphering of the signal needed for this process is required to guide the design of the in vitro tissue culturing conditions. Experimental data obtained by others in the art show that although multipotent human mesenchymal, mouse neural stem cells, and mouse embryonic stem cells can be grown in vitro through the addition of leukemia inhibitory factor (LIF) to the culture medium, mouse ESCs differentiate randomly in vitro and in vivo. Progress in the art has made it possible to induce differentiation of mouse ESCs into multipotent glial cell precursors in vitro and to transplant them into the brain of myelin-deficient fetal rats. However, question remains unanswered as to whether these multipotent stem cells harvested from specific tissues or differentiated from ESCs in vitro will make site-specific tissue when transplanted to injured adult tissues.

Immuno-rejection of the transplant is another major problem associated with cell transplantation. While autogeneic cells can be used in some instances (e.g., mesenchymal stem cells from bone marrow), most transplanted cells will be allogeneic. Attempts have been made to use genetic modification and cell biological strategies to promote host tolerance of allogeneic or xenogeneic transplants, such as fusing diploid somatic cells to an enucleated human or other mammalian egg and using the resultant blastocyst to make the stem cells. Such approaches trigger bioethical concerns, a problem even harder to solve.

Implantation of bioartificial tissues constructed in vitro also faces a few obstacles. For example, it remains a major challenge to synthesize scaffolding material for bionic implants that have the requisite topography, surface properties, and growth and differentiative signals to facilitate cell migration, adhesion, proliferation and differentiation, as well as being moldable into the shape of various tissues and organs. Examples of artificial biomaterials currently being used or tested include various ceramics, polyurethane elastomers, polyesters, polyanhydrides, and polyphosphazenes. These materials provide mechanical support, migration channels, and adhesive surfaces for cells.

Against this technological background briefly summarized above, the present invention provides an innovative methodology for adult tissue repair and organ regeneration. In sharp contrast to the popular approach of in vitro stem cell cultivation taken by most artisans in the field, the methodology is focused on the activation and cultivation of adult stem cells in vivo and in situ. By harnessing the body's inherent ability to repair and regenerate itself, the methodology has been developed to provide optimum conditions for the body's spontaneous regeneration, a regenerative environment mimicking that needed for healthy fetal development. Inventive compositions are provided to activate dormant stem cells to proliferate or to induce conversion of adult tissue cells into regenerative stem cells, and to maintain active proliferation and directional differentiation of these stem cells into all cells needed for regeneration in vivo and in situ. Novel formulation of the active ingredients also facilitates a physiologically moist, nutritious, homeostatically balanced environment to ensure repair and regeneration of tissues and organs with complete restoration of their physiological structures and functions.

As shown later in the Specification, this methodology has been successfully used in the clinic to treat patients with lost or dysfunctional organs, such as patients with deeply burned skin, chronic ulcer, trauma wounds, GI tract ulcer and baldness. Patients can recover with repaired tissue and regenerated organs without substantial loss in their physiological structures and functions.

6) Applications of the Principle in Regenerative Medicine

Under the guidance of the fundamental principle and the methodology elucidated in the present invention, a wide variety of applications in the field of cell biology and in the practice of medicine can be envisioned and have already been demonstrated to be successful in animal models and in human.

Supported by strong evidence collected in experimental models in vitro and clinical trials, the inventor believes that tissue cells in any organ of a human body can be activated to produce regenerative stem cells in response to signals of tissue repair, e.g., wounds, as long as proper regenerative conditions are provided. Unlike scarless wound healing in a fetus at its early gestation stage, physiological tissue repair and functional organ regeneration in a fully developed adult is achievable only by providing an exogeneous culture media in vivo and in situ to stimulate and maintain rapid proliferation and directional differentiation of the adult stem cells and to ensure proper assembly of various tissues organ-specifically without substantial loss in their structures and functions.

The inventor believes that although difficult to be labeled and isolated, multipotent, adult stems cells (ASCs) can be produced in vivo and in situ by activating dormant tissue stem cells and/or by inducing conversion of adult tissue cells into ASCs (FIG. 1). This belief is supported by recent advances in stem cell research and by the experimental and clinical data generated in the application of the fundamental principle elucidated in the present invention.

ASCs have been discovered recently in the liver, pancreas, and central nervous system. Mesenchymal stem cells have been isolated from the bone marrow, and there is some evidence that similar cells may even reside in the connective tissue compartments of tissues throughout the body. The locations of ASCs have been searched extensively and speculated by others to be residing in specific niches. As shown in detail in the Example section, mesenchymal cells in the fat layer of the hypodermis can be induced to produce regenerative ACSs for skin regeneration in response to full-thickness burns under the conditions provided by using the methodology of the present invention.

Regardless of the precise locations of various ACS, the methods and compositions provided by the present invention can be used to activate ACSs in the body to repair damaged tissues and to regenerate dysfunctional organ in situ and in vivo. It is envisioned that this innovative methodology can be used for restoring the physiological structure and function of any tissue and any organ of the body of a mammal, preferably a human. The following section lays out several exemplary applications.

a) Skin Regeneration or Renewal through Cultivation of Epidermal Stem Cells In Vivo and In Situ Skin is the largest organ of an animal, consisting of outer epidermis, dermis, and hypodermis. Normal, physiologically functional skin has these three layer of tissues interact with each other in structurally distinctive patterns.

The epidermis is a continually renewing, stratified, squamous epithelium. Most of the cells in the epidermis are keratinocytes arranged in layers that represent different stages of their differentiation. The outer layer, the horny layer, functions as a barrier. It protects the body from the environment and helps maintain the internal milieu.

The dermis, the connective tissue matrix of the skin, gives the skin its structural strength, protects the body from injury, stores water, and interacts with the epidermis. The papillae of the dermis mirror the contours of the epidermis, i.e., the alternating ridges and valleys of the underside of the epidermis.

Skin as a fully functionally organ includes components, comprising nerves, blood vessels, hair follicles, and glands as appendages of the skin. The numerous components of skin are responsible for its varied functions. These functions include protection from the external environment, inhibition of water loss, absorption and blockage of radiation, temperature regulation, sensory perception, and immunological surveillance.

Blood and lymph vessels in skin play important roles in nutrition supply and in the regulation of temperature and blood pressure. The kinds of cutaneous vascular beds present are determined by the kinds of skin they perfuse, the types and numbers of appendages present, and the thickness of the dermal and hypodermal layers.

Cutaneous nerves contain sensory and sympathetic (autonomic) never fibers. The sympathetic motor fibers, mixed with sensory fibers in the dermis, eventually send branches to the sweat glands, blood vessels, and arrectores pilorum muscles. The sensory fibers and their specialized corpuscular end organs are receptors for touch, pain, temperature, itch and physical and chemical stimuli. A large portion of the human sensory cortex receives sensory messages from the skin of the face and the hands.

The glands, appendages of the skin, include apocrine glands, eccrine sweat glands, mixed glands, buccal glands, and sebaceous glands. Each type of gland has unique morphological characteristics and functions. All of these cutaneous appendages arise from the embryonic epidermis.

Hairs are complex keratinous cylinders packed inside a tight girdle of imbricated cortical scale. Hairs can be divided into (1) vellus hairs, which are fine, unmedullated, soft, unpigmented, and relatively short, and (2) terminal hairs, which are coarse, longer, and mostly pigmented and medullated. There are also intermediate hairs. All fetal hairs are called lanugo hairs.

Hair follicle is the principal epidermal appendage and, together with the epidermis, derived from a common embryonic origin and located at the on the skin surface. The hair follicle is composed of an outer root sheath (ORS) that is contiguous with the epidermis, an inner root sheath (IRS), and the hair shaft itself. The actively dividing cells that give rise to the IRS and hairshaft are called matrix cells. In the follicle bulb there is a pocket of specialized mesenchymal cells, called the dermal papilla, which are a population of transiently dividing epithelial cells.

In the adult hair follicle, the lower segment undergoes periods of active growth (anagen), and destruction (catagen/telogen). As matrix cells exhaust their proliferative capacity, the follicle regresses, dragging the pocket of dermal papilla cells up to the permanent epithelial portion of the follicle, called the bulge. The bulge has been considered to be putative home of follicle stem cells. In response to stimulus from the dermal papilla, one or more stem cells in the bulge commit to regenerating the follicle.

The hypodermis, also called the fatty layer, has a layer of fat. The primary functions of the hypodermis are thermoregulation, cushioning against mechanical trauma, contouring the body, filling space, and most importantly, serving as a readily available source of energy. The hypodermis consists of three fatty layers separated by connective tissue sheaths (retinocula cutis).

The dermis is divided into a papillary layer that follows the contours of the epidermis and a reticular layer that extends from the bottom of the papillary dermis to the hypodermis. The papillary dermis has a high content of type III collagen, which consists of small-diameter fibrils organized into small fiber bundles (1–10 $\mu$m in width). The reticular dermis is composed primarily of type I collagen, which consists of large-diameter fibrils woven into large fiber bundles (more than 40 $\mu$m in width).

Under the light microscope, collagen fiber bundles are arranged in a somewhat orthogonal pattern, i.e., each layer is at right angles to the one above and the one below.

The histologic hallmark of scarless fetal wound healing is the regeneration of dermal appendages and surrounding muscles. However, the prevailing thought is that the skin of an adult with deep partial-thickness burn or full-thickness burn can only be regenerated with scars and substantial loss in the structure and function of the appendages.

Cutaneous scarring may be defined as macroscopic disturbance of normal architecture, resulting from the end product of a healed wound, and may manifest itself as an elevated or depressed site with an alteration of skin texture, color, vascularity, nerve supply, reflectance, and biochemical properties. Ferguson et al. (1996) Plast. Reconstr. Surg. 97:854. Histologically, scarring may be defined as the microscopic alteration of tissue architecture, with collagen deposition and organization that differ from the surrounding unwounded tissues.

Exogenous growth factors administered to the wound locally were shown to able to somewhat increase the rate of wound repair in the laboratory. However, delivery of growth factors made exogenously to the wound site has been proven an unsatisfactory therapy clinically. TGF-β has failed to improve healing. PDGF-BB, which has been approved by the FDA for marketing, only shows marginal gains in chronic wound healing. More disappointingly, this marginal gain occurs only when radical debridement and weight off-loading have been achieved by experienced clinicians.

The environment of human chronic wounds cannot be replicated in experimental animals. For clinicians who wish to use exogenous growth factors to treat wounds face various challenges associated with delivery of protein into a human body. For example, added exogenous growth factors are quickly destroyed by proteolysins and oxidants. Another challenge is that fibroblasts from chronic wounds are often deficient in response to growth factors.

As shown in a later section of the Specification, the present invention provides innovative methodology for tissue repair and organ regeneration of an animal, especially of a human, through cultivation of regenerative stem cells in vivo and in situ. For example, a new skin was regenerated from the site suffering from deep, extensive burns through induction of adult stem cells which developed into embryonic epidermal stem cells and various other tissue stem cells needed for skin regeneration. The regenerated skin retains its normal structure and function and contains a full set of appendages. These "miraculous" clinical achievements demonstrate that the methodology of the present invention can be used for regeneration of various tissues and organs.

In one aspect, the methodology of the present invention may be used to physiologically repair damaged tissue(s) of the skin without scars, such as the skin of a deep second degree burn (or partial thickness burn) that has destroyed the epidermis, the basal layer, and severely damaged the dermis. However, part of the dermis remains viable in the skin. The methodology may also be used to regenerate skin with restoration of structures and functions of the epidermis, dermis and various appendages of the skin. For example, a patient with both epidermis and dermis destroyed by fire or chemical, i.e., superficial third degree burn or full thickness burn, can be treated with the methodology without substantial loss of physiological functions of the skin, including those of the appendages.

In addition, the methodology of the present invention may also be used for regenerating skin that has been damaged by other types of wounds including but not limited to trauma, surgical and infected wounds; surface ulcers including but not limited to chronic ulcers, diabetic ulcers, decubital ulcer, and lower limb vascular disease, and other non-healing wounds as result of poor blood flow; wounds and/or erosions caused by bacterial and viral infection, such as vaginitis, cervical erosion, gingivitis; wounds due to dilation and enlargement of veins such as hemorrhoids; herpes simplex corneal ulcer, subcutaneous tissue ulcer, radiation-caused skin ulcer, wounds caused by wind and cold such as chilblain and chapped skin. By using the compositions provided by the present invention, these types of wounds can be treated and heal physiologically without disfigurement and disablement.

To achieve these functional results in skin, the inventive composition is applied to the damaged skin in situ and asserts its therapeutic activity through activation of regenerative stem cells, tissue-specific cell adhesion, and organ-specific assembly of regenerated tissues.

The regenerative stem cells for skin may reside in the viable tissues of the skin. For example, damaged epidermis may be repaired by activating the epidermal stem cells residing in the epidermal basal layer. The inventive composition may be used as a therapeutic to promote physiological healing of the damaged epidermis without scarring.

In addition, the inventive composition may be used as a cosmetic to enhance aesthetic appearance of the skin. For example, the composition may be delivered to the basal layer via chemical delivery vehicles such as liposomes or oil, or physical means such as ultrasonic delivery. For skin with irregular surface and/or color abnormity caused by internal or external elements such as acne scars, dark spots and wrinkles, partial or the entire epidermis may be removed chemically (e.g., by glycolic acid or enzyme) or physically (by thermal or optical energy). The inventive composition is then applied to the skin with viable dermis where residual basal layer epidermal stem cells and the regenerative stem cells in other tissues of the skin may be activated to promote regeneration of younger looking skin without scarring.

For example, regenerative stem cells may be stimulated in various skin tissues such as the hair follicles. The bulge of a hair follicle has been proposed to be the niche harboring both epidermal and follicle stem cells based on lines of evidence obtained in experimental animals and humans. Bulge cells have a long cell circle (Morris and Potten (1994) Cell Prolif. 27:279–289), and also yields the best outgrowth of hair follicle keratinocytes in culture (Yang et al. (1993) J. Invest. Dermatol. 101:652–659). Other tissues of the skin such as the blood vessels and eccrine sweat glands may also harbor regenerative stem cells that are activated and different into various cells types needed for the repair of dermis and regeneration of the epidermis.

For skin in which both of dermis and epidermis have been completely damaged and/or lost their functions, the inventive composition may be used to activate or induce regenerative stem cells residing in the hypodermis, such as the mesenchymal cells in the soft tissue.

For skin in which all of the components, epidermis, dermis, and hypodermis, have been completely damaged and/or lost their functions, the inventive composition may be used to activate regenerative stem cells from the connective tissues in the muscle layer, as well as mesenchymal stem cells from bone marrow.

It should be noted that the inventive method and composition may also be used to promote dedifferentiation of cells, i.e., to convert a differentiated cell into an adult stem cells that then serve as the regenerative stem cells in the process of the tissue repair and organ regeneration.

b) Prevention and Treatment of Cancer by Restoring Homestatic Balance of Tissues The methodology described in the present invention can also be used to prevent and treat various forms of cancer. Cancer is generally viewed as the result of disrupted intra- and intercellular homeostatic regulation. Once the homeostatic balance is lost and malignant transformation has occurred, microenvironment factors such as degradation of matrix components and host-tumor interactions are essential for survival and growth of the malignant cells.

By using the inventive compositions and methods, the present invention shows that the homestatic balance of tissues can be restored without loss of physiological functions. The inventive composition can regulate intercellular communication and promote cell-cell interactions by stimulating cross-talk mediated by various cell membrane proteins such as connexins and cadherins. This results in a coordinated regulation of cell growth, differentiation, apoptosis and migration.

The inventive composition may assert its function of restoring tissue homestatic balance through promoting the formation of gap junctions between precancerous or cancer cells and the host cells. Gap junctions are a unique type of intercellular junction found in most animal cell types. Two adjacent cells interact with each other through the cell membrane proteins, connexins, which form the gap junction. Six identical connexins from a connexon; two connexons join across the intercellular gap to form a continuous aqueous channel connecting the two cells. Each gap junction is a cluster of homogeneous intramembrane particles associated with the cytoplasmic fracture face of the plasma membrane. Each intramembrane particle corresponds to a connexon. Gap junctions permit the intercellular passage of small molecules and have been implicated in diverse biological processes, such as development, cellular metabolism, and cellular growth control.

The majority of connexins are modified posttranslationally by phosphorylation, primarily on serine amino acids. Connexins are targeted by numerous protein kinases, of which some have been identified: protein kinase C, mitogen-activated protein kinase, and the v-Src tyrosine protein kinase. Phosphorylation has been implicated in the regulation of a broad variety of connexin processes, such as the trafficking, assembly/disassembly, degradation, as well as the gating of gap junction channels.

In addition, another cell membrane protein cadherin also plays important role in cell-cell adhesion and migration. It has been found that cadherin-mediated cell-cell adhesion is perturbed in protein tyrosine kinase (PTK)-transformed cells. While cadherins themselves appear to be poor PTK substrates, their cytoplasmic binding partners, the Arm catenins, are excellent PTK substrates and therefore good candidates for mediating PTK-induced changes in cadherin behavior. For example, beta-catenin binds to the cytoplasmic region of classical cadherins and function to modulate adhesion and/or bridge cadherins to the actin cytoskeleton.

It is likely that the inventive composition activates these kinases which then phosphorylate connexins and the cellular binding partners of cadherins such as catenins. Through proper phosphorylation of these proteins associated with cell-cell adhesion, the communication channels between the tumor cells and the host cells are restored. With the restoration of tumor-host connection, the tumor cells are subjected to the regulation of the host. Under the regulation of the host, the tumor cells may be induced to undergo apoptosis (programmed cell death) or differentiate to become non-tumorigenic. Thus, the homeostatic balance of the tissue is restored to prevent or inhibit malignancy of tumors.

In one embodiment, the methodology of the present invention may be used for treating or preventing hyperproliferative diseases or pre-cancerous conditions affecting epithelial cells of the skin, such as psoriasis or other skin diseases, including hyperproliferative, pre-cancerous or UV-induced dermatoses.

Further, the methodology of the present invention may also be used as prophylaxis against skin cancer or reduction in the likelihood of development of skin cancer, as well as reduction of severity of photoaging resulting from sun exposure.

In another embodiment, the methodology of the present invention may be used for treating or preventing hyperproliferative diseases or pre-cancerous conditions affecting epithelial cells of the internal organs, such as organs in the gastrointestinal (GI) tract. Administration of the inventive composition orally or via local injection may restore the homeostatic balance of these organs by reestablishing the cell-cell cross-talk between the precancerous cells with the healthy cells of the host.

Further, the methodology of the present invention may also be used for treating cancer in the upper and lower GI tract. Examples of upper GI cancer include, but are not limited to, 1) esophagus cancer caused by excessive alcohol use, lye ingestion, achalasia, cigarette smoking, exposure to nitroamine, Barrett's mucosa, tylosis, mycotoxin, infection with transforming viruses such as human pappiloma virus (HPV), herpes simplex virus (HSV), cytomegalovirus (CMV) and Epson-Barr virus (EBV), Plummer Vinson Syndrome; 2) stomach cancer caused by achlorhydria, *Helicobacter pylori* infection, previous gastrectomy, and Billroth II procedure; 3) pancreas cancer caused by cigarette smoking, exposure to beta-naphthylamine, benzidine, and chronic pancreatis; 4) liver cancer caused by hepatitis B virus, chronic liver diseases such as chronic active hepatitis and cirrhosis, exposure to mycotoxin, ionizing radiation, steroid hormones and arsenic; and 5) cancer of bile ducts caused by sclerosing cholangitis, parasitic infections and steroid hormones. Examples of lower GI cancer includes cancers of the large bowel such as colorectal carcinoma, primary lymphomas, melanoma, and sarcoma of the large bowel. Adenocarcinomas account for more than 90% of large bowel cancers. Cancinoid tumors account for most of the rest of malignant neoplasma arising in the colorectum.

c) Prevention and Treatment of Diseases in the Gastro-Intestinal Tract

In another aspect, the methodology of the present invention may be used to activate or induce regenerative stem cells in tissues in the GI tract so as to repair diseased or damaged mucosa of the organs in the tract.

In the lining of the small intestine, cells are arranged as a single-layered epithelium. This epithelium covers the surfaces of the villi that project into the lumen of the gut. Mucus-secreting goblet cells are interspersed among the adsorptive brush-border cells in the epithelium. The epithelium also lines the crypts that descend into the underlying connective tissue. It has been found that each crypt is composed of about 250 epithelial cells among which epithelial stem cells are included. These multipotent stem cells are located near or at the base of each crypt. Loeffler et al. (1993) J. Theor. Biol. 160:471–491. The intestinal epithelial stem cells response to mesenchymal cues for survive and differentiation. Normally, these cells are slowly recycling, much like the hair follicle stem cells. Some of them are converted to rapidly but transiently proliferating cells that move to the midsegment and subsequently differentiate into either the absorptive brush-border entercytes, mucus-secreting goblet cells, or enteroendocrine cells of the villi. To maintain homeostasis, the differentiated cells then die and are shed from the villi into the lumen of the gut.

In a related aspect, the present invention provides methods and compositions for treating digestive disorders in a human patient, which method involves administering to the digestive tract the patient a composition comprising a sterol compound dissolved in oil, the concentration of the sterol ranging from about 0.5% to 20% by weight. In a preferred embodiment, the oil is edible oil, and the composition further comprises beeswax at a concentration ranging from about 1% to 20% by weight.

Digestive disorders may be a condition of a human as a result of disorders of and damage to the organs of the digestive tract or the alimentary canal, including the mouth, esophagus, stomach, and large and small intestine. Disorders of the digestive tract include peptic ulcer diseases, inflammatory bowel diseases and other insults.

One of the common causes of the disorder in the GI tract is bacterial infections caused by *Helicobacter pylori* (*H. pylori*). Infection of *H. pylori* leads to active, chronic gastritis and frequently to associated syndromes such as duodenal ulcer, gastric ulcer, gastric cancer, MALT lymphoma, or Menetrier's syndrome. Eradication or inhibition of *H. pylori* should reduce the recurrence of duodenal and gastric ulcers.

Long-standing gastritis associated with *H. pylori* infection is often associated with the expression of intestinal-like features in the gastric mucosa. This condition, referred to as intestinal metaplasia (IM), may signal an increased risk of gastric cancer, is the second leading cause of cancer related death world-wide.

The etiology of IM is unclear; it could represent a mutational adaptation or defense against *H. pylori* infection. It has been speculated that the metaplastic mucosa may produce mucus or other substances that create an environment that is hostile to *H. pylori*. Thus, widespread treatment of *H. pylori* should reduce the incidence of gastric carcinoma.

The inventor believes that the inventive composition can effectively repair the damaged mucosa by providing regenerative condition in the GI tract, especially in the stomach. Upon administration to the GI tract, the inventive composition is mixed with mucus of the stomach and form a protective membrane containing mucin, separating the mucosa from further irritation of food and other materials contained in the stomach. Under these conditions the sterol compound and other optional active ingredients in the composition are released to the site and activate the regenerative stem cells there to promote fast repair of the mucosa. As shown in FIG. 3B the inventive composition successfully cured gastric ulcer in animal models (compared with FIG. 3A, without the treatment). Further, the inventive composition may also effectively inhibit the toxicity of the bacteria *H. pylori* by changing its morphology. With the regeneration of a healthy GI tract, the ulcerous conditions that are favorable for *H. pylori* are improved and therefore indirectly inhibit the growth of the bacteria.

The methods and composition of the present invention can be used in the treatment of *H. pylori* infection and conditions associated with *H. pylori* infection (e.g., ulcers, gastric carcinoma, non-ulcer dyspepsia, gastritis, and esophageal lesions associated with gastro-esophageal reflux disease). The inventive composition is useful for treatment of these conditions because of its generally protective effect on the gastrointestinal (GI) tract. In addition, it promotes the maintenance of mucosal integrity.

The inventive composition of the present invention can be used to inhibit adhesion to or colonization of the mucosa by *H. pylori*. It may also be used promote healing of tissues damaged by conditions associated with *H. pylori* infection. In this regard, it is important that addition of the inventive composition to wounded monolayers of confluent intestinal epithelial cells activates epithelial stem cells in the crypts and increases the rate of epithelial cell migration into the wound.

Just as the inventive composition can be used to protect other parts of the gastro-intestinal tract or alimentary canal, such as the intestine, it can be used to protect the mouth and esophagus from damage caused by radiation therapy or chemotherapy.

The inventive composition can also be used to protect against and/or to treat damage caused by alcohol or drugs generally.

d) Promotion of Hair Growth and Treatment of Baldness

The methodology of the present invention may also be used to promote hair growth and restore physiological functions to hair follicles and their surrounding tissues such as blood vessels and the sebaceous gland.

Hairs are filamentous, keratinized structures derived from the epidermis. Two broad categories of hairs are recognized: vellus hairs are short and narrow, and are present over most of the body surface; terminal hairs are longer, thicker, and often heavily pigmented. Terminal hairs include those of the scalp, eyebrows and eyelashes, post-pubertal hair of the axillae and pubis, and the facial and body hair of many men.

Each hair consists of a shaft and a root. The shaft is composed of specialized keratinocytes. The root lies within the hair follicle, which can extend deeply into the hypodermis or lie more superficially in the dermis. The hair follicle is composed of an outer root sheath (ORS) that is contiguous with the epidermis, and an inner root sheath (IRS). The actively dividing cells that give rise to the IRS and hair shaft are called matrix cells. The proximal end of the root is expanded to form the hair bulb, which is indented on its deep surface by a conical vascular dermal papilla. The bulb comprises the germinative matrix and the keratogenous zone. In the follicle bulb there is a pocket of specialized mesenchymal cells, called the dermal papilla, which are a population of transiently dividing epithelial cells. This mass of pluripotent cells capping the dermal papilla are characterized by mitotic activity giving rise to the hair and its surrounding inner root sheath. Cells arising mitotically from this group move apically and differentiate along several different routes.

In the adult hair follicle, the lower segment undergoes periods of active growth (anagen), and destruction (catagen/telogen). As matrix cells exhaust their proliferative capacity, the follicle regresses, dragging the pocket of dermal papilla cells up to the permanent epithelial portion of the follicle, called the bulge. The bulge has been considered to be putative home of follicle stem cells. In response to stimulus from the dermal papilla, one or more stem cells in the bulge commit to regenerating the follicle.

Follicular development relies on a series of messages between dermis and epidermis. During embryogenesis, the formation of hair follicles results from interactions between the epidermis and mesenchyme. The dermal components of the hair follicle (i.e., the dermal papilla and dermal sheath) are derived from an aggregate of mesenchymal cells. Follicle initiation and development begin with the aggregation of dermal fibroblasts and epidermal keratinocytes. The epidermal cells proliferate and penetrate the dermis as plugs. Subsequently, the epidermally derived cells encircle a dermal aggregation and incorporate it into a pocket of tissue, the dermal papilla. It is generally understood that the population of hair follicles and dermal papillae is established during embryogenesis with no significant postpartum development.

Hair growth is affected by proliferation of hair follicle matrix cells. Three distinct stages in the hair growth cycle are recognized: anagen, an active phase when hair growth occurs; catagen, the transition stage during which follicle activity declines; and telogen, the resting phase when no cell proliferation occurs. In the typical human scalp, anagen lasts several years, catagen lasts a few weeks, and the quiescent telogen phase lasts a few months (Bertolino et al. (1993) "Biology of Hair Follicles" in Dermatology in General Medicine, pp. 289–93, Fitzpatrick et al., eds. McGraw-Hill). The timing of this renewal cycle differs between species and location within an animal. Following telogen, the hair falls out and another cycle begins. The various phases of the hair growth cycle are accompanied by characteristic changes in the thickness of the epidermis, dermis, and adipose layer. Additionally, in terminal hairs, anagen is accompanied by increasing melanogenesis as melanocytes in the hair follicle produce melanin that is incorporated into the hair shaft. Danilenko et al. (1996) Mol. Med. Today 2:460–67.

Numerous factors affect this cycle. For example, various growth factors, steroid hormones, dermo-epithelial interaction, dermal vascularity, neuroectodermal factors, and the immune system have been implicated. Stenn et al. (1996) Dermatol. Clin., 14:167–96; and Lindler et al. (1997) Am. J Pathol., 151:1601–17.

There are many types of baldness, each with a different cause. Baldness may be localized to the front and top of the head, as in the very common type of male-pattern baldness; baldness may be patchy, a condition called alopecia areata; or it may involve the entire head, as in alopecia capitis totalis. The various forms of baldness can be categorized as follows: 1) Alopecia capitis totalis which is loss of all of the scalp hair, i.e., a total baldness of the scalp with normal hair elsewhere on the body; 2) Alopecia universalis which is loss of all of the hair, not only on the scalp, but also on the entire body; 3) Alopecia areata which is a condition with patchy areas of baldness, and for women, the hair loss usually happens following childbirth or stopping the contraceptive pill; 4) Hair loss as a result of chemotherapy, the resultant hair loss usually being temporary; 5) Hair loss as a result of radiation therapy administered to the head, the hair loss usually being permanent, due to irreversible damage to the hair follicles; and 6) Male pattern baldness (also referred to as bald pate) with the common male-pattern baldness localized to the front and top of the head, due to genetic (hereditary) factors.

Hair loss (alopecia) is a naturally occurring process in mammals; indeed, it is extremely common among healthy adult humans, especially men. Alopecia also can be induced by chemical agents or physical agents (e.g., during anti-cancer chemotherapy), and the condition also results from specific disease states and with increasing age. Alopecia typically is attributable to a disturbance in the hair renewal cycle, leading, at first, to acceleration of the frequency of the cycles, resulting in a shift in the population of follicles from the anagen phase to telogen. Normally, of the approximately 150,000 hairs on the typical human head, about 10% of them are in telogen at any given time; in skin undergoing alopecia, significantly more follicles are in telogen. Ultimately, the hair follicles degenerate. This process manifests itself as a progressive thinning of the hair, first as a change of hair quality (i.e., more vellus and less terminal hair) and ultimately in a decrease in the number hairs in the affected area of skin.

In addition to hair loss, abnormally accentuated growth of hair can result from some rare conditions. For example, hirsutism is manifested as excessive androgen-dependent hair growth in women; hypertrichosis is an increase in androgen-independent hair growth. Bertolino et al. (1993) "Disorders of Epidermal 35 Appendages and related disorders" in Dermatology in General Medicine, pp. 671–95, Fitzpatrick et al., eds., McGraw-Hill). Such conditions can lead to profound social consequences for affected individuals.

As a result of the prevalence of alopecia, hirsutism, hypertrichosis, and other disorders, there is immense interest in the development of effective cosmetic and clinical treatments. However, despite such a need, effective prophylaxis and therapy remains elusive. For example, one method used to combat alopecia, hair transplant surgery, is not available to many people suffering from alopecia (e.g., patients having undergone chemotherapy, elderly individuals, etc.). Moreover, surgery offers, at best, only a partial remedy. Electrical stimulus has been suggested as an alternative way to promote hair growth (see, e.g., U.S. Pat. No. 5,800,477 and references cited therein); however, such methods are of questionable efficacy.

As shown in FIG. 4B, topical administration of the inventive composition to the scalp results in regrowth of hair in a bald male (compared with FIG. 4A, before the treatment). The Inventor believes that the inventive composition effectively activates hair follicle stem cells, likely the stem cells residing the bulge of a hair follicle. Proliferation and differentiation of the regenerative stem cells provides enough hair cells for forming strong, healthy hair shafts.

e) Repair of Tissues of and Regeneration of other Organs

Figure 4C:
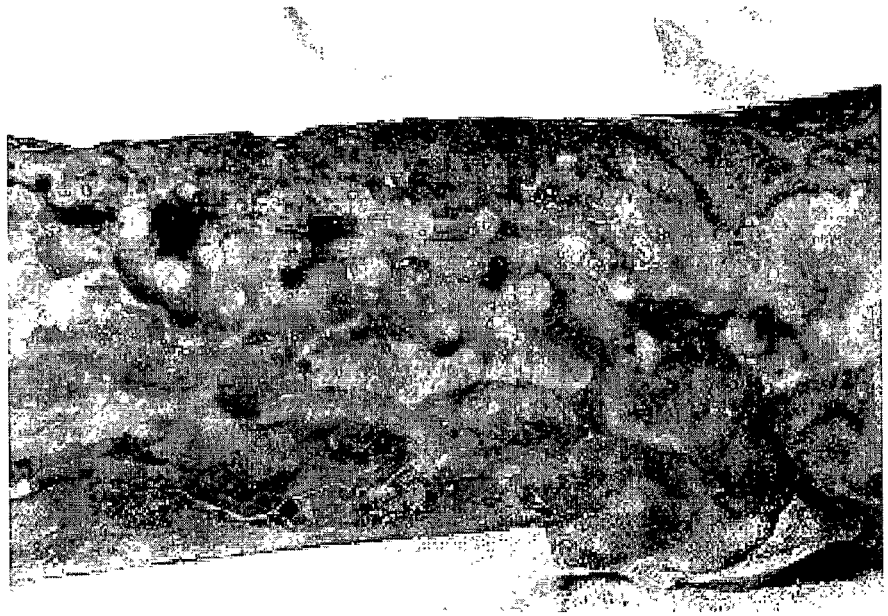
FIG. 4C shows that in the presence of the inventive composition nascent flesh grew from the holes drilled in the bone in a burn patient's leg that was burned to the bone.
Figure 4D:
FIG. 4D shows expansive growth of flesh on the wound in the patient described in FIG. 4C with continuous application of the inventive composition.

The inventive methodology can also be used to repair tissues of or regenerate other organs of the body through cultivation of regenerative stem cells in vivo and in situ, including but not limited to muscles, mucus, tendons, connective tissue, heart, kidney, lung, liver, pancreas, eyes, brain, arteries, nerves, and bones. As shown in FIGS. 4C and 4D, the inventive composition has been successfully used to regenerate muscles, connective tissues, tendons, blood vessels, and nerves by cultivating multipotent or pluripotent stem cells from bone marrow. As shown in FIG. 4C, on a leg of a patient who suffered from severe burn in the leg and all of the skin as well as the flesh attached to the skin was burned away, revealing the bone of the burned leg. Holes were drilled in the bone at this wound site to release bone marrow to the wound bed and the inventive composition was applied topically to the wound. In the presence of regenerative environment provided by the inventive composition, adult stem cells from the bone marrow differentiated orderly into various types of cells needed for the growth of nascent flesh from the holes. FIG. 4D shows expansive growth of flesh on the wound in the patient described in FIG. 4C with continuous application of the inventive composition.

The inventive composition may also be administered by local injection to the heart muscle to directly activate/induce ASCs of the heart for treating various heart disorders and cardiovascular diseases, as well as regeneration of the heart post heart attack. Further, the inventive composition may be administered locally to the liver to activate/induce hepatocyte stem cells to repair the liver damaged in various courses such as over consumption of alcohol. Moreover, the inventive composition may be administered to the lung locally to repair or regenerate tissues therein such as lung alveolus.

Moreover, the inventive composition may be used to repair damaged renal glomerulus and other glomerulous disease, the major causes of chronic renal failure. In the kidney, the glomeruli are small structures (100–200 μm in diameter) scattered throughout the renal cortex ($3\times10^5$–$1\times10^6$ glomeruli/kidney) and, therefore, are difficult to be targeted by conventional approaches such as implantation. Direct injection of the inventive composition should provide sufficient stimuli to the glomerulus and activate/induce regenerative stem cells therein.

In addition, the inventive compositions and methods may be used to treat other disorders resulting from a loss or reduction of a renewable cell population through activation or induction of regenerative stem cells, including blood disorders and diseases involving impaired or lost immune function. Also, the inventive composition may be used to stimulate the growth and maintain the physiological balance of differentiated cells, inducing existing differentiated cells to continue expressing their phenotype and to reverse from an aged phenotype to a youthful one. This is particularly useful in the treatment of tissue disorders where loss of function is caused by reduced or lost metabolic function and cells become senescent or quiescent, such as may occur in aging cells and/or may be manifested in osteoporosis and a number of nerve degenerative diseases, including Alzheimer's disease.

2. Cellular and Molecular Mechanisms of the Inventive Compositions

The present invention provides a novel approach to tissue repair and organ regeneration. This approach is against the current main-stream school of thoughts that complete organ regeneration can only be achieved by transplantation of autografts or allografts that are reconstructed ex vivo. In stark contrast to this popular and dominating approach, the fundamental concept proposed in the present invention is that a fully developed, adult human with severely damaged tissues and/or organs possesses an intrinsic ability of self-repair and organ regeneration in a suitable environment and in response to endogenous and exogenous signals. Such a regenerative environment must be supported by substances provided exogenously in order to promote the organ regeneration without substantial loss of physiological structures and functions. Under the conditions created by applying the inventive composition in vivo and situ, the target organ could regenerate spontaneously with a restoration of its physiological structure and function by following an embryonic development-like process.

The inventor believes that activity of a cell, the smallest unit of which life is composed, plays critical roles in the process of physiological tissue repair and organ regeneration. Although numerous growth factors participate in the process, ultimately the cellular activity must be regulated as a whole to achieve a homeostatically balanced regeneration. Tissue repair and organ regeneration through modulation of a single or a limited number of growth factors could likely to result in incomplete restoration of physiological structures and functions because the exquisite balance of life is kept by complex cellular activity regulated by the body itself, not controlled by just a few growth factors.

As disclosed in Section 1 above, the inventor reveals the fundamental principle behind adult tissue repair and organ regeneration in response to endogenous and exogenous signal. Under the regenerative conditions provided by using the methodology of the present invention, novel cellular responses and intercellular interactions were observed on organs undergoing spontaneous regeneration. These phenomena could only be observed when the inventive composition is applied. For example, skin with deep second degree burn healed with scars in the control group or in a group treated with conventional drug SD-AG; and wounds caused by superficial third degree burns could only be closed by skin grafts. The cellular and tissue interactions in the wounds treated by using these traditional methods are chaotic, leading to pathological healing of the skin with disfiguring scars, disablement and dysfunction. To restore physiological structures and functions to damaged adult tissues and organs, exogenous substance must be applied to the site to provide a regenerative environment and to regulate cellular activity in vivo and in situ.

Although not wishing to be bound by the theory as to the role each ingredient in the inventive compositions played in the regenerative process, the inventor proposes in the present invention the plausible molecular and cellular mechanisms based on 1) the understanding of embryonic development and the difference between fetal and adult wound healing process; 2) the knowledge of the physical, chemical and pharmokinectical properties of the ingredients; and 3) the preclinical and clinical observations of the cell growth, tissue repair and organ regeneration under the regulation of the inventive composition.

1) Human Embryonic Development

A human, like other multicellular animal or plant, is an ordered clone of cells which contain the same genome but specializes in different ways. Although the final structure may be vastly complex, a human life is generated by a limited repertoire of cell activities: cell growth, division and death. Human cells differentiate by switching on or off the production of specific sets of proteins, a process controlled by the intrinsic program of the human genome and influenced by various environmental elements. Cells produce molecular signals to influence neighboring cells and they respond to signals that neighboring cells deliver to them. It is generally believed that the genome, repeated identically in every cell, defines the rules of cellular response to various stimuli and guides the whole intricate multicellular process of development by which an adult organism is generated from an embryo.

After fertilization of the egg by the sperm, the single large egg cell subdivides by repeated mitosis into many small cells, termed blastomeres, without change in total mass. This process is called the cleavage of the egg cell. At this stage, DNA replication and mitosis occur at a very high rate and the cleaving embryo is almost entirely dependent on reserves of RNA, protein, membrane, and other materials that accumulated in the egg. After the cleavage process, the cell division rate slows down and transcription of the embryo's genome begins. This change is known as the mid-blastula transition.

From the outset, the cells of embryo are not only coupled bound together mechanically, they are also coupled by gap junctions through which ion and other small molecules can pass. This feature enables efficient conveyance of messages that may help to coordinate the behavior of the cells. Meanwhile, in the outermost regions of the embryo, tight junctions between the blastomeres create a seal, isolating the interior of the embryo from the external medium. At about the 16-cell stage, Na+ begins to be pumped across the cell membranes into the spaces between cells in the interior of the embryo, and water follows because of the resulting osmotic pressure gradient. As a result, the intercellular crevices deep inside the embryo enlarge to form a single cavity, termed the blastocoel. At this stage, the embryo is termed a blastula.

The cells that form the exterior of the blastula become organized as an epithelial sheet, setting the stage of the coordinated movements of gastrulation. This dramatic process transforms the simple hollow ball of cells into a multilayered structure. The multilayered structure of blastula consists of three layers: inner, outer, and middle layers. A central gut tube forms the inner layer by tucking cells from the exterior of the early embryo into the interior.

In the three-layered structure created by gastrulation, the innermost layer, the tube of the primitive gut, is the endoderm. The outermost layer, the epithelium that has remained external, is the ectoderm. In between these two layers, the looser layer of tissue composed of mesenchyme cells is the mesoderm. Such an organization of the embryo into the three layers corresponds roughly to the organization of the adult—gut on the inside, epidermis on the outside, and connective tissue and muscle in between.

Early development of a mammalian embryo is highly regulative. The fate of each cell is governed by interaction with its neighbors. However, when the circumstances of development are more grossly abnormal, the embryonic cells can go wildly out of control. For example, when a normal early mouse embryo is grafted into the kidney or testis of an adult, it rapidly becomes disorganized, and the normal controls on cell proliferation break down. The result is a bizarre growth known as a teratoma. The teratoma consists of a disorganized mass of cells which contain various differentiated tissues such as skin, bone, glandular epithelium. These differentiated cells are mixed with undifferentiated stem cells that continue to divide and generate yet more of these differentiated tissues.

Embryonic stem (ES) cells are extraordinarily adaptable to environmental cues that guides choices between different pathways of differentiation. Under appropriate conditions, ES cells can also stop or start the development clock—the processes that drive a cell to progress from an embryonic to an adult state. For example, stem cells with very similar properties can be derived by placing a normal inner cell mass in culture and disperse the cells as soon as they proliferate. Once dispersed, some of the cells, if kept in suitable culture conditions, will continue dividing indefinitely without altering their character. The resulting ES cell lines can divide infinitely without differentiating. The presence in the medium of a protein growth factor or cytokine known as leukemia inhibitory factor (LIF) seems to be critical for this suspension of developmental progress. Nichols et al. (1998) Cell 95:379–39; and Niwa et al. (1998) Genes Dev. 12: 12:2048–2060. Upon LIF withdrawn, cultured ES cells spontaneously aggregate into embryo-like bodies, where they differentiate and spawn many cell lineages, including beating heart muscle cells, blood islands, neurons, pigmented cells, macrophages, epithelia, and fat-producing adipocytes. Bradley (1990) Curr. Opin. Cell Biol. 2:1013–1017. However, the triggering of these developmental programs is chaotic, yielding a jumbled "grab bag" of tissue types. Fuchs et al. (2000) Cell 100:143–155.

Because of such uncontrollable, chaotic development of cultured ES cells in vitro, it remains a challenge for people who attempt to regenerate organs ex vivo and then transplant them to the patient with complete restoration of physiological structure and function. To reconstruct a fully functional organ from ES cells in vitro, an enormous challenge is to sift through a "galaxy" of environmental signals to determine which "constellations" of cues can selectively "coax" ES cells down a specific lineage pathway at the expense of all others. Various attempts have been made to produce "pure" cells of one specific type from ES cells. For example, pure populations of multipotent progenitor cells that express glial precursor markers were produced from mouse ES cells. Brustle et al. (1999) Science 285:754–756. The whole process was quite elaborate. Aggregates of cultured ES cells are propagated sequentially in medium containing 1) first fibroblast growth factor 2 (FGF2) alone, 2) then a mixture of FGF2 and epidermal growth factor (EGF), and 3) finally a mix of FGF2 and platelet-derived growth factor (PDGF). Eventually, these pluripotent cells bathed in such a "designer cocktail" of growth factors could be maintained for many generations in culture.

These achievements in producing a pure population of cells of one specific tissue type, although significant and heroic, are far from reaching the goal of organ regeneration ex vivo. It should be recognized that a population of cells of a single type are not tissue. To reconstitute a physiologically viable tissue cells of at least two types are required. These cells must be able to conduct cross-talk with each other via intricate intercellular signal transduction pathways in a physiological environment. Before these signals are deciphered and absent a suitable physiological environment as in the body itself, attempts to reconstruct a fully functional organ in vitro would most likely to fail despite of extensive intervention with cocktails of growth factors.

By contrast, the present invention demonstrates clinically that severely damaged organ of human body can be regenerated in vivo and in situ without transplantation. A significant contributory factor is that by using the inventive composition and methods, adult stem cells (ASCs) are induced and propagated to provide various types of regenerative cells which reconstitute to form various tissues. Since these regenerative cells grow from the body itself in situ, instead of being transplanted ex vivo, their growth and differentiation follow the genetic programs set up during the body's embryonic development. However, since these regenerative ACS are exposed to a completely different, more hostile environment than those in a fetus, the fate of the ASCs is not only controlled by endogenous regulatory mechanisms but also by exogenous interference such as bacterial infection and air pollutants. Thus, exogenous substances must be provided to promote proliferation of the ASCs so as to produce large numbers of tissue cells required for regeneration. Further, the differentiation of the ASCs should be regulated by providing a favorable environment mimicking that for embryonic development. Moreover, the interactions between cells of the same or different types should be regulated so as to promote tissue-specific homing and adhesion. So are the interactions between tissues so as to promote organ-specific assembly of regenerated tissues into a functional organ within the body.

Using wound healing in burned skin as a model for organ regeneration in adults, the inventor has tested the effects of the inventive composition on stem cell growth and differentiation as well as on specific cell-cell, cell-tissue, and tissue-tissue interactions. In addition, these effects were also observed in in vitro models treated with the inventive compositions.

2) Epidermal Stem Cells

Stem cells are required wherever there is a recurring need to replace differentiated cells that cannot themselves divide. As cells in the outermost layers of skin (epidermis) are terminally differentiated and can no longer divide to replenish the dead keratinocytes, the epidermal stem cells located at the basal layer in the junction between the epidermis and the dermis constantly divide and provide daughter cells that differentiate into various types of keratinocytes to renew the skin.

The epidermis is a multilayered epithelium composed largely of keratinocytes. Keratinocytes are cells that differentiate with characteristic activity of synthesis of intermediate filament proteins called keratin. Keratinocytes express keratin of different types depending on their stages of differentiation, such as keratin-1, -9, -10 and -16. In particular, keratin-19 (K-19) is found to be expressed in the basal cell layer of fetal epidermis and in the bulge of the developing hair of human fetuses. Dale et al. (1985) J. Cell Biol. 101:1257–1269; and Moll et al. (1982) Differentiation 23:170–178; and Akiyama et al. (2000) J. Invest. Dermatol. 114:321–327. K-19 expressing keratinocytes have been recognized as the putative epidermal stem cells.

Keratinocytes differentiated from the epidermal stem cells change their appearance from one layer to the next. Those in the innermost layer and attached to an underlying basal lamina are basal cells that undergo mitosis to produce more epithelial cells. Above the basal cells are several layers of larger prickle cells whose numerous desmosomes provide sites of anchorage for keratin filaments. Beyond the prickle cells lies the thin granular cell layer which marks the boundary between the inner, metabolically active strata and the outermost layer, consisting of dead cells whose intracellular organelles have disappeared. These outermost cells are reduced to flattened scales, or squames, filled with densely packed keratin.

When some basal cells are dividing and adding to the population in the basal layer, others types of keratinocytes are slipping out of the basal cell layer into the prickle cell layer. When they reach the granular layer, the cells start to lose their nuclei and cytoplasmic organelles and are transformed into the keratinized squames of the keratinized layer. These finally flake off from the surface of the skin. Generally, the period from the time a cell is born by the epidermal stem cell in the basal layer of the human skin to the time it is shed from the surface varies from 2 to 4 weeks, depending on the region of the body.

In principal, the division of an epidermal stem cell could generate two initially similar daughter cells whose different fates would be governed by subsequent circumstances. To assure constant supply of new skin cells each self-renewing patch of epidermis must contain in each cell generation at least on "immortal" stem cell, whose descendants will still be present in the patch in the distant future. However, production of stem cells may increase depending on the circumstance. For example, when a patch of epidermis is destroyed, the damage is repaired by surrounding healthy epidermal cells that migrate and proliferate to cover the denuded area. In this process, a new self-renewing patch of epidermis is established, implying that additional stem cells have been generated to make up for the loss.

To produce more stem cells, the daughter cells of a stem cell may themselves be stems cells and not embark on the path leading to terminal differentiation. The fate of these daughter cells are governed by the circumstances. One possible determining factor might be contact with the basal lamina or with the exposed connective tissue at a wound. Loss of contact triggering the start of terminal differentiation and maintenance of contact tending to preserve stem cell potential. It has been found that contact with extracellular matrix has a critical influence on the choice of cell fate. If the cells are held in suspension, instead of being allowed to settle and attach to the bottom of the culture dish, they all stop dividing and differentiate. It has also been found that in normal physiological conditions possession of fibronectin receptors by keratinocytes holds the cells bound to the basal lamina, keeping open their option to remain as stem cells. Loss or inactivation of the receptors leads to ejection from the basal layer, confirming the decision to differentiate; and ejection from the basal layer through other causes leads to loss of the receptors, forcing the cell to differentiate prematurely.

Thus, physiological interactions between cells and between cells and tissues are important for stem cells to maintain their undifferentiated state. As shown later in the Specification, in the models for stem cell growth and differentiation in vivo, adult stem cells were activated, interact with each other in a tissue-specific manner, and differentiate directionally into various types of cells required for regeneration of all tissues of the skin, including its appendages. These specific interactions were observed in the wound healing process of deeply and extensively burned skin under the treatment with the inventive composition. As also shown later in the in vitro models, without proper cell-cell interactions promoted by the inventive composition, hair follicle stem cells from rats could not undergo clonal proliferation to form skin tissues.

3) Adult Wound Healing

Wound healing in an adult is a complicated process that typically goes through four phases: coagulation, inflammation, proliferation and remodeling.

First, the initial coagulation process involves the exposure of platelets to fibrin and collagen and the deposit of a prominent layer of fibrin. The first stimulus to wound healing is most commonly the injury-induced, arachidonic acid-mediated activation of tissue complement. This stimulation attracts polymorphonuclear granulocytes to the injury site and serves as a defense against infection. If blood vessels have been ruptured during injury, subendothelial collagen is exposed to platelets, resulting in the initiation of the coagulation cascade. The activated platelets initially release biochemical mediators that cause vasoconstriction and consequently minimize blood loss. Platelets also interact with the injured tissues, causing the release of thrombin, which converts soluble, circulating fibrinogen to fibrin, which in turn traps and activates platelets and forms the physical entity of the hemostatic "plug". As these activated platelets degranulate, their $\alpha$-granules release a variety of cytokines and growth factors that are largely chemoattractants (chemotaxis) for the inflammatory cells such as neutrophils and monocytes and mitogens for the noninflammatory cells such as fibroblasts and endothelial cells that are involved in subsequent wound healing. The fibrin clot also serves as scaffolding upon which and through which these cells can proliferate and migrate. In addition, the activated platelets participate in the regulation of extracellular matrix (ECM) synthesis needed for wound healing. Examples of cytokines and growth factors secreted by platelets include platelet-derived growth factor (PDGF), transforming growth factor $\beta_1$ and $\beta_2$ (TGF-$\beta_1$ and TGF-$\beta_2$), platelet-derived epidermal growth factor (PDEGF), platelet-activating factor (PAF), insulin-like growth factor-1 (IGF-1), fibronectin, and serotonin.

Second, the inflammatory phase begins within a few hours of the initiation of coagulation. This process is a defense against infections and a bridge between tissue injury and new cells growth. During this phase, inflammatory cells are attracted to the injury site and undergo activation. Once the bleeding has ceased at the end of the coagulation (or hemostasis) phase, vasodilation and increased capillary permeability follow.

Neutrophiles, then macrophages, migrate into the wound, characterizing acute inflammation. These inflammatory cells provide phagocytosis of bacteria and debridement of injured tissue. This is proceeded by chronic inflammation where lymphocytes and monocytes infiltrate the wound site. The latter become macrophages, which are considered the main coordinators of adult wound healing.

Neutrophils phagocytize contaminating bacteria and digest the fibrin matrix in preparation for new tissue. They also secrete vasodilatory mediators and cytokines that activate fibroblasts and keratinocytes and attract macrophages to the injury site. Macrophages phagocytize potential pathogens, debride the wound, and secrete cytokines and growth factors such as fibroblast growth factors (FGF), epidermal growth factor (EGF), vascular endothelial growth factor (VEGF), tumor necrosis factor (TNF-a), interleukin-1 (IL-1) and interferon-gamma (IFN-γ). These chemical messengers also stimulate the infiltration, proliferation, and migration of fibroblasts and endothelial cells, resulting in angiogenesis.

Subsequently, fibroblasts enter the wound site to replace the existing fibrin matrix with glycosaminoglycans and proteoglycans. The healing ECM also contains many glycoproteins, including fibronectin, and tenascin. Fibronectin promotes substrate adhesion, whereas tenascin facilitates substrate migration by antagonizing fibronectin.

Further, fibroblasts and endothelial cells convert dissolved molecular oxygen to superoxide, which is important in resistance to wound infection as well as oxidative signaling in further stimulation of growth factor production.

Third, in the subsequent days, a wide variety of cells increase proliferation and migrate to the wound, including macrophages, lymphocytes, fibroblasts, epithelial cells (i.e., keratinocytes), and endothelial cells for constructing blood vessels. During the migratory and proliferation processes, these cells that are recruited into the healing wound undergo rapid mitosis and begin to define the ultimate structure of the scar.

During this phase, a process known as epithelization occurs in order to re-epithelialize the wound edges. During the epithelization process, an epidermal covering composed predominantly keratinocytes begins to migrate and undergo stratification and differentiation to reconstitute the barrier function of epidermis. This process also promotes extracellular matrix (ECM) production, growth factor and cytokine expression and angiogenesis through the release of growth factors such as keratinocyte growth factor (KGF). Keratinocytes stimulate angiogenesis by releasing basic fibroblast growth factor (FGF) and vascular endothelial growth factor (VEGF). They also secrete TGF-α which acts as a chemoattractant and mitogen, and PDGF which is involved in matrix production. Further migration and proliferation of fibroblasts lead to the replacement of proteoglycan in the ECM with collagen deposition. In addition, endothelial cell proliferation creates neovascularization, i.e., angiogenesis.

Once a monolayer of keratinocytes covers the wound surface, proliferation and synthetic activities decelerate, migration ceases, and differentiation and stratification help establish a new, stratified epidermis with a basal lamina.

However, scarring begins to occur at this stage. The formation of the new epidermis is facilitated by the contraction of the underlying connective tissue. The connective tissue helps wound closing by bringing the edges of the wound closer together. Scarring is greater when the connective tissue continues to accumulate without contracting. In addition, eschars form when wounds are exposed to dry air and are incapable of supporting overlying cells. Consistently, adult wounds treated by conventional dry therapy heal with contracting scars and severe disfigurement.

Finally, the process of tissue remodeling begins as the level of proliferative and migratory activity begins to slow down. This phase involves synthesis of extracellular proteins and proteoglycans and a balance of collagen lysis and collagen synthesis. Although macrophages and lymphocytes are involved in the process, the predominant cell types undergoing proliferation and migration include epithelial cells, fibroblasts, and endothelial cells. The processes are dependent on the nature of available metabolic substrates, oxygen concentration, and growth factors. Remodeling may last for a period of several weeks, months, or even years. During this phase, fibroblasts are the predominantly active cells as they combine to deposit a new matrix, reestablish tissue continuity, and determine the extent of scar formation. Therefore, the growth and differentiation of fibroblasts should be specifically regulated in order to prevent their hyperactivity of collagen deposition.

During the course of wound healing, growth factors have been implicated in diverse activities, such as mitogenesis, motogenesis, angiogenesis, chemotaxis, migration, and remodeling. In particular, TGF-β is the most studied since it is directly related to fibrosis. It is released by a number of cells involved in inflammation including platelets, monocytes, and macrophages and is involved in all most all stages of wound healing. It is known to chemoattract inflammatory cells, stimulate collagen deposition, inhibit collagenase, mediate extracellular matrix components, block plasminogen inhibitors, and promote angiogenesis. Chang et al. (1995) Aesth. Plast. Surg. 19:237–241. Elimination of the effects of results in reduction of excessive amount of angiogenesis, inflammatory cell infiltration, and upregulation of other growth factors.

Disappointingly, an increased level of TGF-β to healing wounds does not necessarily correlate with the improvement of the quality of scarring. The administered exogenous TGF-β results in increased inflammatory cell and fibroblast levels, collagen deposition, and fibrosis. Shah et al. (1992) Lancet 339:213–214. Hence, the balance of growth factors may play a crucial part in wound healing.

Currently, the prevailing thought in the art is that adult wound healing must be scarring healing because the adult-type, "normal" inflammatory wound healing is evolved to reduce the risk of infection at the expense of healing quality. As demonstrated in the present invention, this dogma is changed by the showing of the evidence of scarless wound healing in adults suffering from deep, extensive burns. Based on compelling evidence collected clinically showing dynamic changes of cells at both the cellular and tissue levels, the adult wound healing process under the conditions provided by using the methodology of the present invention mimics fetal scarless wound healing.

4) Fetal Scarless Wound Healing

In contrast to spontaneous, autonomous adult wound healing, fetal wound healing is marked by significant differences in inflammatory response and growth factor profiles. There is decreased infiltration of endogenous immunoglobulins in fetal wound. Longaker et al. (1990) J. Pediatr Surg. 25:63–69. This reduced neutrophil infiltration is not due to the inability of the fetus to produce neotrophils. Further, direct correlation has been reported between increased macrophage recruitment in older fetuses and the development of increased scarring. Hopkinson-Woolley et al. (1994) J. Cell. Sci. 107:1159–1167.

The growth factor profile of fetal healing also differs from adult healing. TGF-β and basic FGF are minimally detectable in fetal wounds by immunohistochemical techniques. Whitby and Ferguson (1991) Dev. Biol. 147:207–215. Although PDGFs are initially present in both adult and fetal wounds, they disappear more rapidly in the fetal wounds. This may be explained by the lower macrophage infiltration associated with fetal wounds. Thus, lack of growth factor degranulation can explain the decreased inflammatory cell recruitment. This may further contribute to lower levels of other growth factors in fetal wound. In addition, bathed in the warm, sterile amniotic fluid, a fetus could heal its wound spontaneously under such a physiological moist, isolated environment without scar and loss of function.

5) Wound Healing under the Conditions Provided by Using the Methodology of the Present Invention In contrast, the wound healing process in an adult with fully developed organs is carried out in a relatively more hostile environment than that for a fetus. The wound is susceptible to adverse effects caused by "normal" inflammatory response of the body to wounding and by exogenous agents such as bacteria that causes infection and further inflammation systemically and on the site. As discussed above, the prevailing thought in the art is that adult wound healing must be scarring healing because the adult-type, "normal" inflammatory wound healing is evolved to reduce the risk of infection at the expense of healing quality. The present invention changes this dogma by showing that an fully developed adult possesses an inherent ability of self-repair and regeneration in response to wounding if suitable conditions are provided exogenously, and the wound healing process can mimic that occurring in a fetus at the early gestation stage to result in scarless healing in severely damaged skin.

Using skin, the largest organ of the body, as a model for tissue repair and organ regeneration, the inventor demonstrated that adult skin can be regenerated without substantial loss of its structures and functions, including those of the appendages through cultivation of regenerative adult stem cells (ASCs) in vivo and in situ. Dynamic changes in the cells and tissues in the wound were monitored during the process of wound healing under the conditions provided by using the methodology of the present invention.

Figure 6:
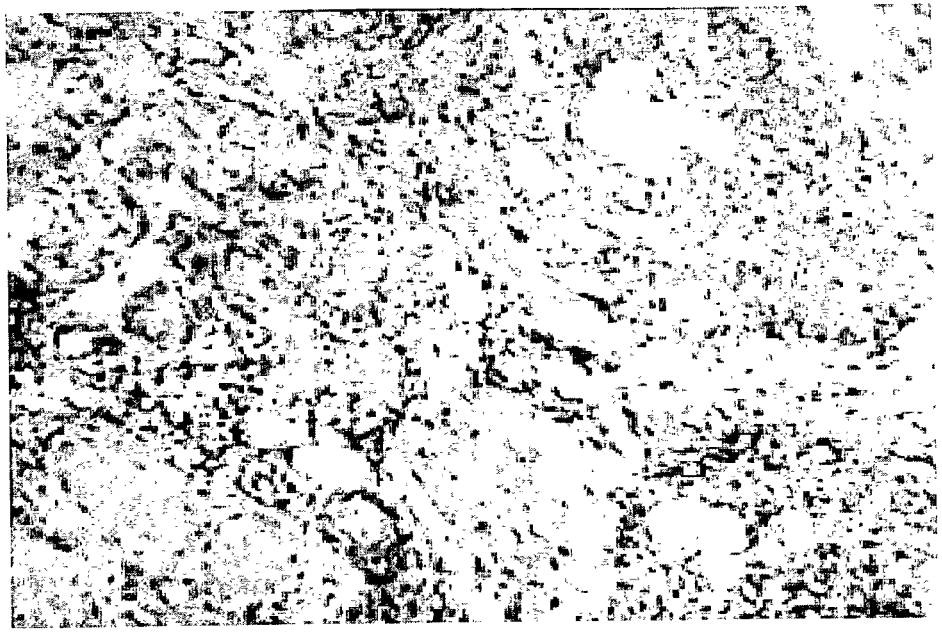
FIG. 6 shows proliferation of regenerative stem cells at the wound site of the patient described in FIG. 5C.
Figure 7:
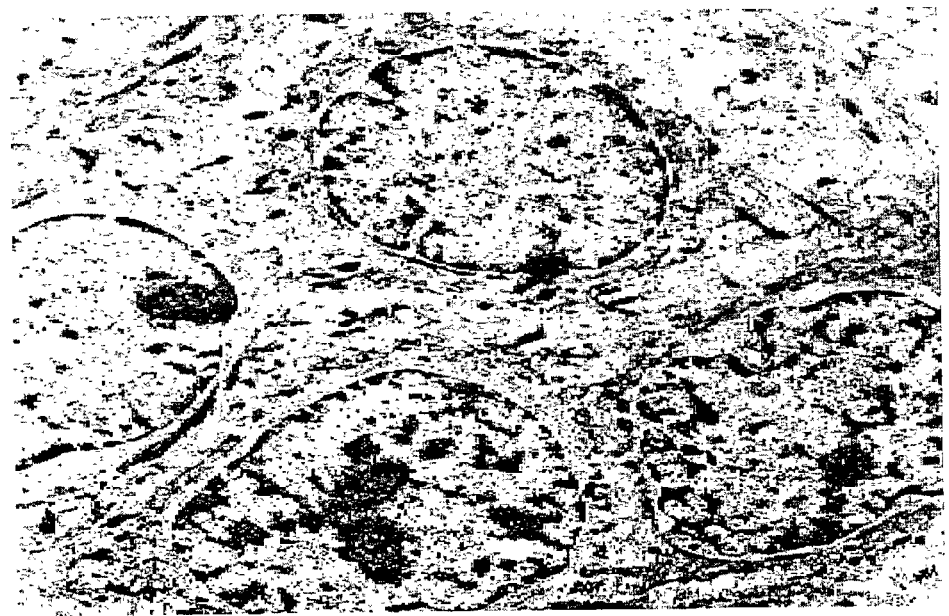
FIG. 7 shows tissue-specific conjunction between regenerative stem cells described in FIG. 6 observed at a higher magnification of a microscope.

FIGS. 5A-C show the changes in the cells and tissues in a wound caused by deep second degree burn in the first ten days of the injury. As shown in FIG. 5A, on day 1 post injury there was coagulation and necrosis of epidermis and degradation of collagenous fibrous in superficial layer of the dermis. At this stage, there was activation or induction of ASCs in response to wounding (to be shown in later part of this section). On day 6 post injury, under the treatment using the inventive composition, the necrotic tissues in the superficial layer was liquefied and discharged gradually (FIG. 5B). Because the necrotic tissues are liquefied instead of being surgically removed, the remaining viable tissues are protected from secondary injury caused by surgery. Under these conditions adult tissue cells in the viable tissues were induced to transform into ASCs which then developed into various tissue stem cells needed for regeneration of skin, such as blood vessels, hair follicles, collagenous fiber, interstitium and nerves. As shown in FIG. 5C, on day 10 post burn there was already high activity of regeneration at the wound site. As also shown in detail in FIG. 6, at this stage of wound healing, there was a lot of tissue stem cells actively proliferating at the site. At a higher magnification, tissue-specific conjunctions between such regenerative stem cells were observed (FIG. 7).

Figure 8:
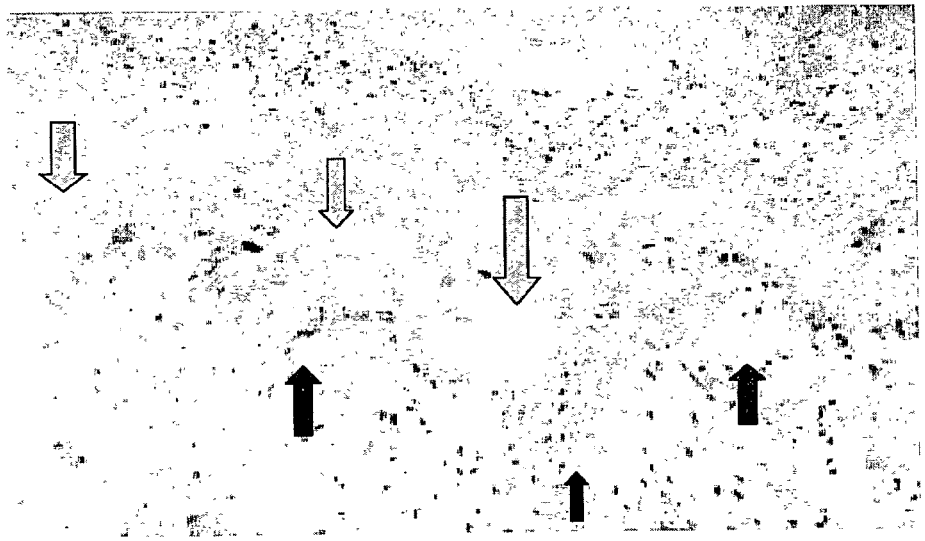
FIG. 8 shows dynamic movements of various types of cells during wound healing in the presence of an embodiment of the inventive composition.
Figure 9:
FIG. 9 shows active anabolism of fibroblasts at the wound site described in FIG. 8 observed at a higher magnification of a microscope.

These tissue stem cells then differentiate directionally into various types of cells which migrate and associate with each other by following the genetic programs already set up at the embryonic stage. As shown in FIG. 8, there was a dynamic movement of cells of various types towards the direction where their cognate tissues originally reside. For example, cells belonging to the dermis began to move downward (indicated by gray arrows) and epidermal cells upward (indicated by black arrows). At a higher magnification, active anabolism of fibroblasts was observed (FIG. 9). Fibroblasts play important roles in wound healing by producing collagen needed for maintaining the structure of the skin. However, during spontaneous, autonomous wound healing or wound healing under the treatment using the conventional methods, the growth of fibroblasts is more active than normal due to the increase in growth factor production in response to wound infection. Overgrowth of fibroblasts leads to overproduction of collagen which aggregates to form disorderly fibers and eventually causes scarring after closure of the wound.

In contrast, skin wounds regenerated by using the present methodology healed without scar for deep second degree burns or with only smooth, soft scars for third degree burns. The inventors believes that the growth of fibroblasts should be controlled and the ratio between fibroblasts and epithelial cells should be maintained at a physiological level. In the wound treated by using the inventive composition, the deposition of collagen of fibroblasts and the ratio between fibroblasts and epithelial cells were controlled at a physiological level, presumably through promotion of fibroblast maturation by the inventive composition. Consistently, in vitro experiments on mouse fibroblasts in cell culture demonstrated that in the absence of the inventive composition, the fibroblasts grew quickly and manifested morphology similar to transformed cells (FIG. 10A). In contrast, in the presence of the inventive composition, the fibroblasts maintain their morphology typical of a matured fibroblast (FIG. 10B).

Figure 11:
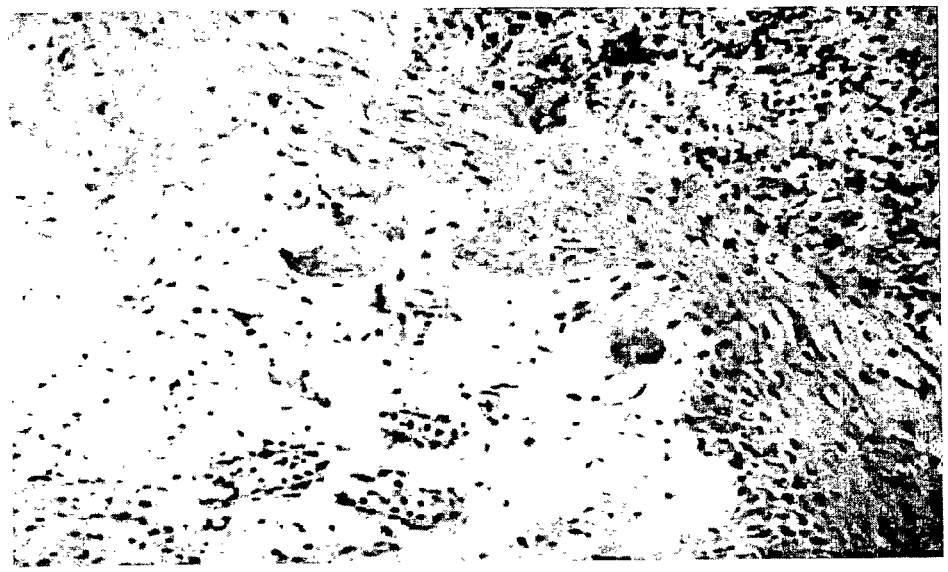
FIG. 11 shows that on day 20 post injury, most of the wound was covered by stratified squamous epithelium and most of the appendages started to form in the dermis.

On day 20 post injury, most of the wound was covered by stratified squamous epithelium and most of the appendages started to form in the dermis (FIG. 11). Meanwhile, there was also active exudation of cellular wastes out of the newly-formed epidermis.

Figure 12:
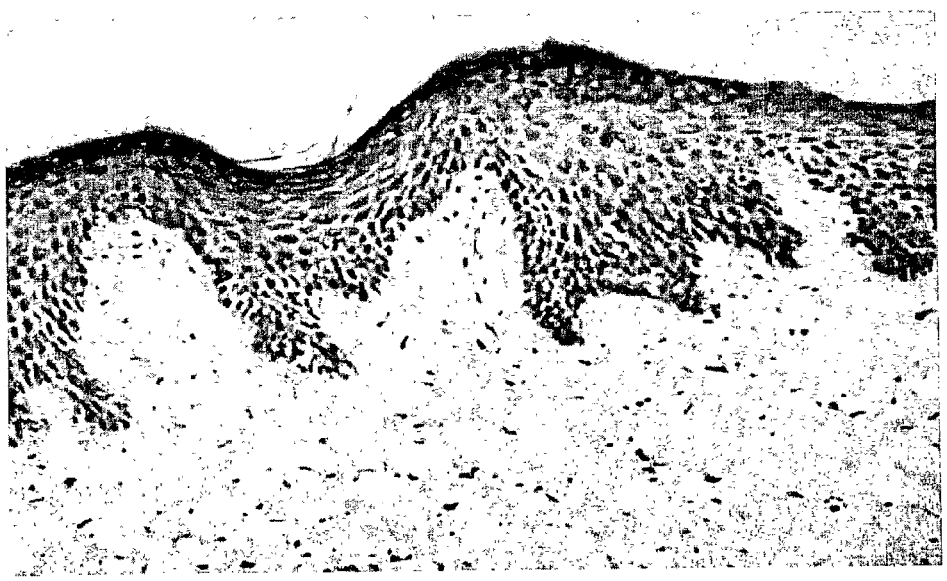
FIG. 12 shows that on day 22 post injury, the skin was regenerated with normal structure.
Figure 13:
FIG. 13 shows that at a higher magnification under electron microscope, the junction between the dermis and epidermis is completely natural.
Figure 14:
FIG. 14 shows that collagenous fibers in the new skin are arranged in a normal order three dimensionally.

On day 22 post injury, the skin was regenerated with normal structure as shown in FIG. 12. At a higher magnification under electron microscope, the junction between the dermis and epidermis is completely natural (FIG. 13). Moreover, collagenous fibers in the new skin are arranged in a normal order three dimensionally (FIG. 14).

Consistent with the effects of the inventive composition on cells and tissues during wound healing of burned patient in the clinic, in vitro experiments conducted on animal cell and tissue culture also demonstrated that the inventive composition has unique activities in promoting proliferation and tissue-specific adhesion of normal differentiated mammalian cells and mammalian stem cells, as well as maintaining the integrity of organ structure.

FIGS. 15A-D show the results of the in vitro experiments on mouse skin cell culture in the presence and absence of the inventive composition. On day 10 cells in both groups appeared to grow healthily (FIG. 15A). However, there was a dramatic change in cell survival and growth in the two groups. In the control group, cells started to die on day 30 whereas cells in the treatment group survived and retained normal morphology (FIG. 15B). On day 49 there was more cell death in the control group whereas the cells in the treatment continued to proliferate actively (FIG. 15C). On day 70 cells in the control group all died. In sharp contrast, cells in the treatment group still grew strongly and almost reached confluency (FIG. 15D). During the observation period of 6 months, cells in the treatment group still kept proliferation without showing abnormal morphology.

These results show that the inventive composition is capable of promoting the growth of primary cell, presumably by transforming primary skin cells into epidermal stem cells with a potential of continual proliferation. This is consistent with the effects on adult cells in human treated with the inventive composition.

FIGS. 16A-C show the results of the in vitro experiments on rat hair follicle stem cell culture in the presence and absence of the inventive composition. As shown in pictures in the right column of FIG. 16, the stem cells in the control group survived but grew as individual cells. In contrast, stem cells in the treatment group proliferated and started to adhere to each other and form clones (left column of FIG. 16). On day 41 there were many clones formed in the treatment group, manifesting a tissue-like morphology, whereas the cells in the control group, although proliferative, remained scattered without forming any clone.

These results demonstrate that the inventive composition is capable of promoting not only proliferation but also tissue-specific adhesion of stem cells. This is also consistent with the effects on adult cells in human treated with the inventive composition.

FIGS. 17A-C show the results of the in vitro experiments on mouse skin tissue culture in the presence and absence of the inventive composition. As shown in pictures in the right column of FIG. 17, there was migration and scattering of cells in the control group. In contrast, there was little migration and scattering of cells in the treatment group and the newly generated cells remained adhered to the skin pieces (left column of FIG. 17). On day 44 cells in the treatment group continued to proliferate and integrated into the skin pieces which showed clear margins under microscope. In contrast, the cells continued to dislodge from the skin pieces and scattered in the culture of the control group.

These results demonstrate that the inventive composition is capable of promoting adhesion of cells to its cognate tissue and maintaining the integrity of a normal skin structure. This is also consistent with the effects on adult cells in human treated with the inventive composition.

To monitor the dynamic changes of cells in growth and differentiation during the process of adult organ regeneration in vivo, wound healing of deeply burned skin was used as a clinical model to demonstrate how adult cells respond to endogenous and exogenous agents under the treatment using the methodology of the present invention.

As to be shown below, the present invention demonstrates for the first time that embryonic epidermal stem cells are induced or activated and able to proliferate in adult human under conditions favorable for physiological tissue repair and organ regeneration. Such regenerative conditions are provided by applying the methodology and compositions disclosed in the present invention.

During the treatment of an adult who suffered a superficial third degree burn, regenerative stem cells needed for regenerating various skin tissues were activated under the optimal condition provided by the inventive composition. Among these regenerative cells, embryonic epidermal stem cells expressing the marker keratin-19, i.e., K-19 keratinocytes, were specifically detected by using immunohistochemical and immunofluorescence techniques. Dynamic changes in the level of K-19 expressing regenerative cells were also monitored at different time points during the period of skin regeneration of this patient.

Figure 18:
FIG. 18 shows a 20 years-old female sustained a gasoline burn in her limbs with 35% total burn surface area (TBSA).
Figure 19:
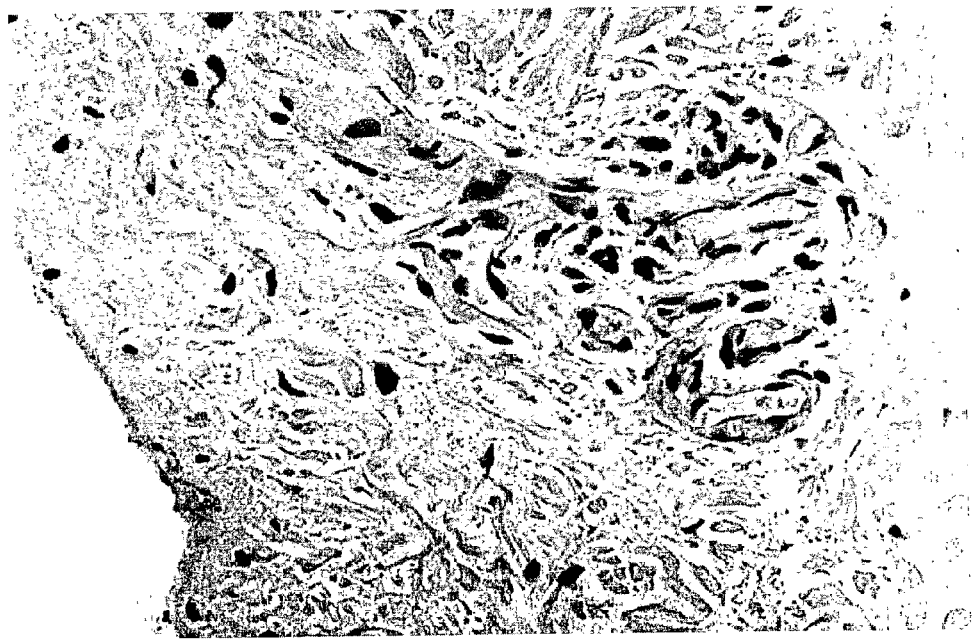
FIG. 19 shows pathological analysis revealed 15% deep partial-thickness burn and 20% superficial full-thickness burn.

A 20 years-old female sustained a gasoline burn in her limbs with 35% total burn surface area (TBSA) (FIG. 18). Pathological analysis revealed 15% deep partial-thickness burn and 20% superficial full-thickness burn. Microscopic examination of sections of the tissues from the burn wounds revealed full-thickness necrosis of skin cells, degeneration and structural disturbance of collagenous fibers in dermis and microcirculation stasis (FIG. 19).

Figure 21:
FIGS. 21 and 22 shows that there was active proliferation of nascent epithelial tissues, collagenous fibers and the skin embryonic base (EB).
Figure 22:
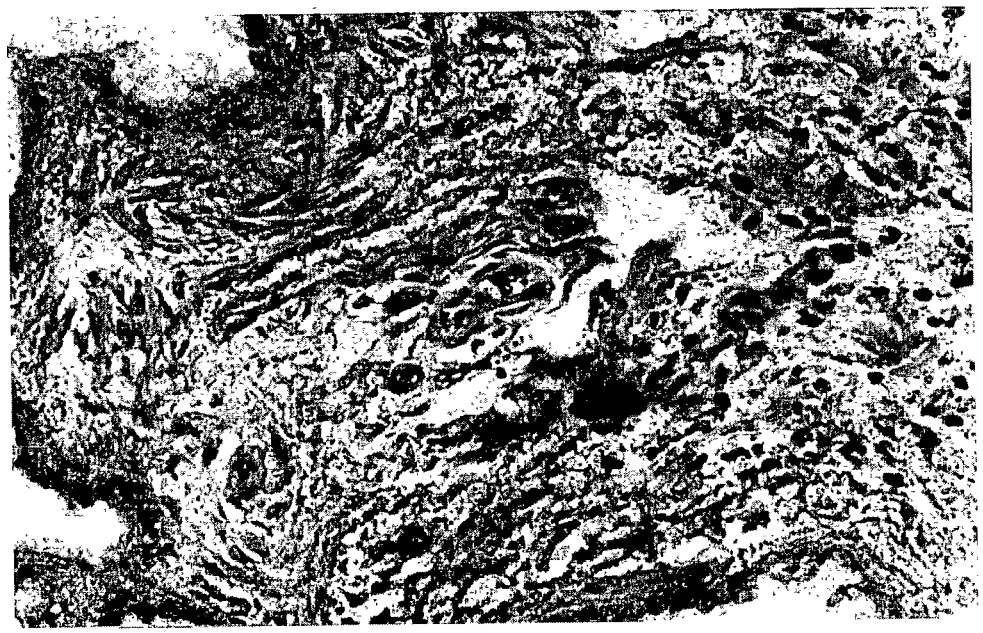

Immunohistochemical examinations of normal and burned skins were performed by treating with specific mouse anti-human keratin type 19 monoclonal antibody. The results revealed that in the normal epidermis of this patient, few cells were K-19 positive (FIG. 20A). In contrast, for skin in the wounds, there was a moderate amount of regenerative epidermal stem cells which were stained positive for K-19 24 hr post burn (FIG. 20B). On day 4 post burn, the number of regenerative epidermal stem cells increased around the sweat gland, capillaries and hair follicles (FIG. 20C). Microscopic examination of the sections of skin undergoing regeneration revealed that there was active proliferation of nascent epithelial tissues, collagenous fibers and the skin embryonic base (EB) (FIGS. 21 and 22).

On days 7 (FIG. 20D) and 14 (FIG. 20E) epidermal stem cells continued to increase, reaching a peak value during this period. Until day 21 (FIG. 20F) and day 28, the number of regenerative stem cells decreased to low levels.

Figure 28:
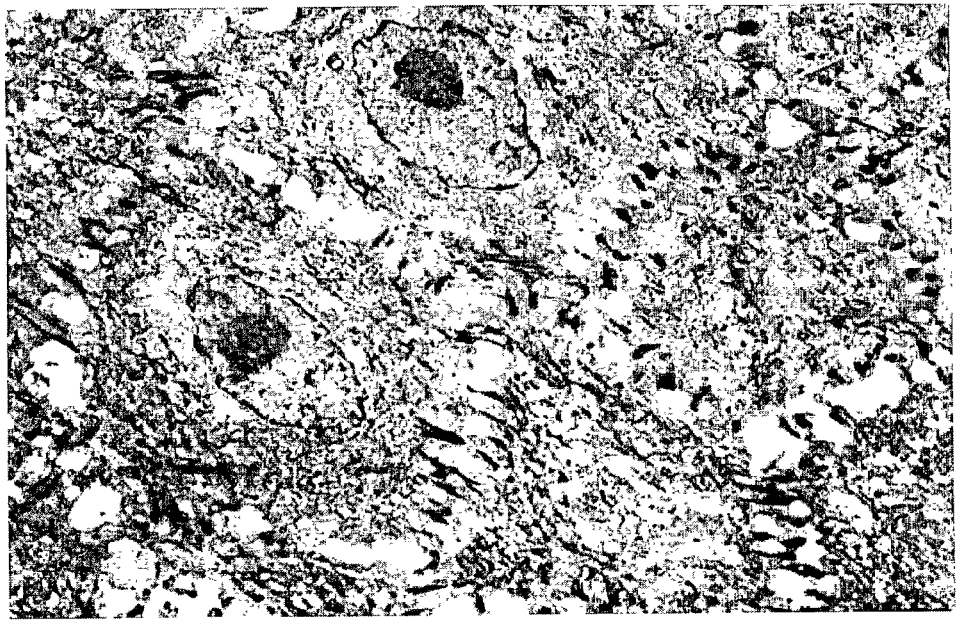
FIG. 28 shows that desmosome junctions formed between echinocytes in the regenerating skin on day 20 post burn.
Figure 29:
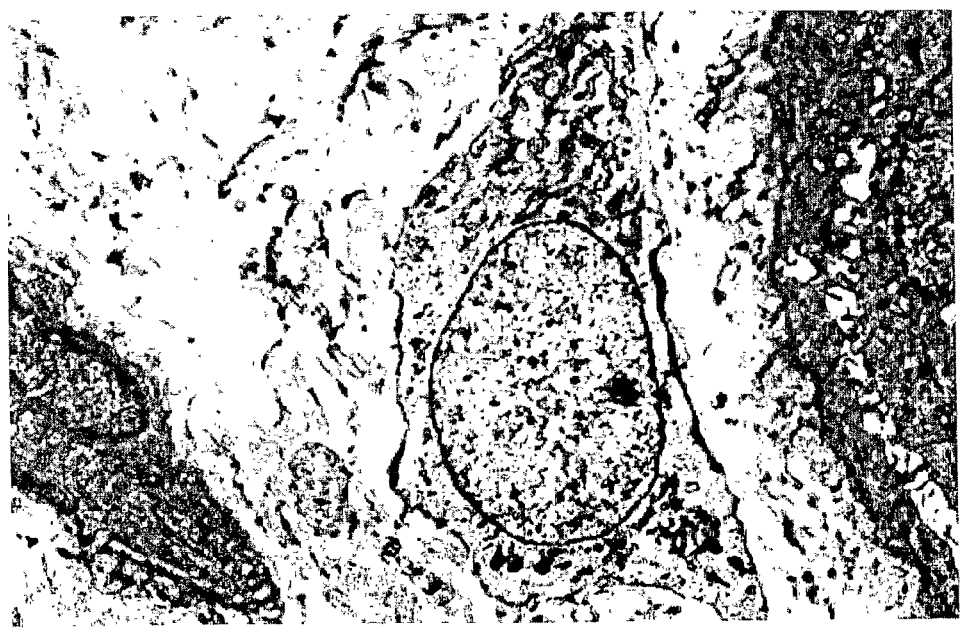
FIG. 29 shows that hemidesmosome junction formed between epithelial cells and the basement membrane on day 20 post burn.

On day 20 post burn, microscopic examination of the sections taken from the healing wound site revealed that hemidesmosome junction formed between epithelial cells and the basement membrane (FIG. 29). Further, desmosome junctions also formed between echinocytes (FIG. 28).

Figure 24:
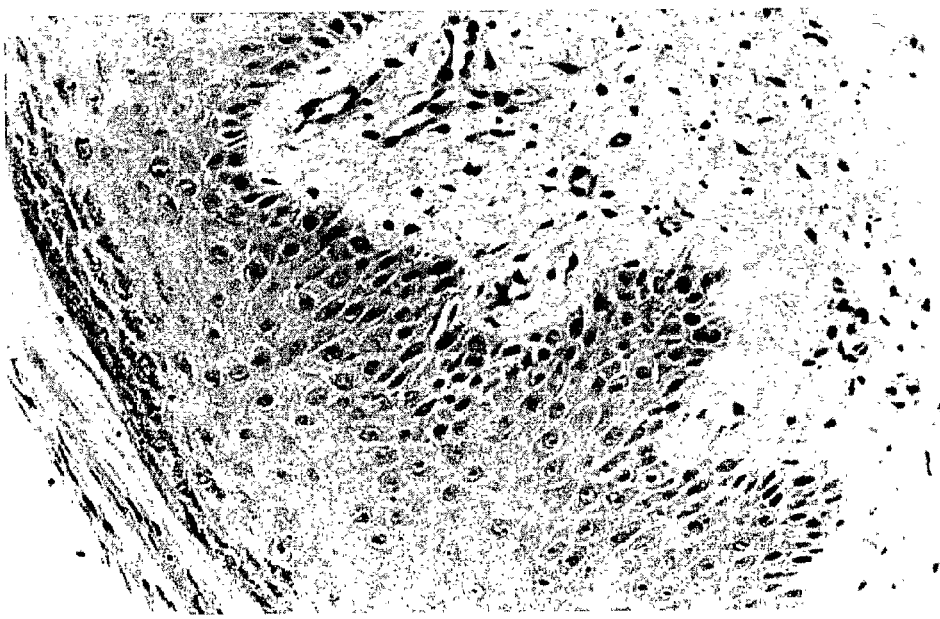
FIG. 24 shows that the skin regenerated by using the methodology of the present invention retains its normal, physiological structure.
Figure 25:
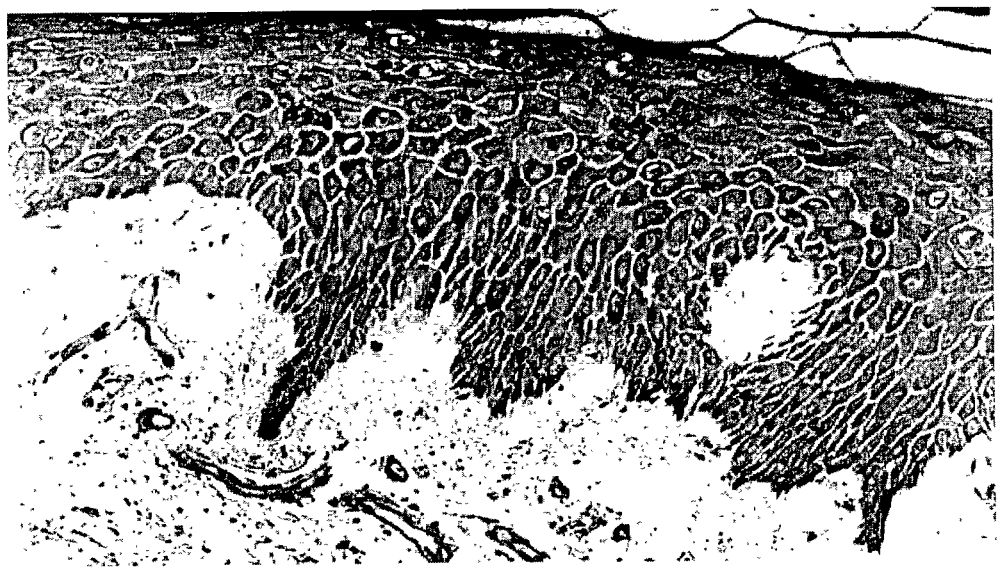
FIG. 25 shows that after the treatment with the inventive method and composition for 30 days, the basal membrane in basal lamina of epidermis was actively regenerative.
Figure 26:
FIG. 26 shows that the collagenous fibers in the regenerated new skin were normal in both size and spatial arrangement.

On day 30 post burn, electron microscopic examination of the sections taken from the new skin of the patient revealed that the skin regenerated by using the methodology of the present invention retains its normal, physiological structure (FIG. 24). Also, the collagenous fibers in the regenerated new skin were normal in both size and spatial arrangement, measured 0.1–05 $\mu$m and with characteristic light and dark periodic cross striation (64 nm) (FIG. 26). Argentaffin staining of the section showed that after the treatment with the inventive method and composition for 30 days, the basal membrane in basal lamina of epidermis was actively regenerative (FIG. 25).

Figure 23:
FIG. 23 shows the regenerated new skin of the patient described in FIG. 18 on day 30 post burn.

To confirm that the skin was regenerated from the patient's own body not from exogenous sources, immunohistochemical staining was performed on sections taken from the regenerated skin of this patient 30 days post burn. Immunohistochemical analysis of the section stained with $AE_3$ revealed positive protein of squamous epithelium, indicating spontaneous self-regeneration of the skin (FIG. 27A). Consistently, the section stained with $AE_1$ showed negative protein of glandular epithelium (FIG. 27B). These results demonstrate for the first time that a new human organ can be regenerated in vivo and in situ with normal, physiological structures and functions at both cellular and tissue levels (FIG. 23).

In burn wounds of deep second degree (deep partial-thickness burn) or worse, epidermal stem cells residing in the basal layer of epidermis are destroyed. More interestingly and challengingly, in burn wounds of superfacial third degree (full-thickness burn), the whole epidermis and dermis are destroyed with only hypodermis, the fatty layer of the skin, remaining viable. Treatment of full-thickness burn with conventional methods such as dry therapy and skin grafts results in wound-closure with disfiguring scars and substantial loss of normal functions of appendages of the skin. However, as shown above, an adult sustained both deep second degree and third degree burn could recover with skin regenerated without substantial loss of its structures and functions. What is the source(s) of cells that compose to form the tissues which constitute the regenerated organ?

The present invention provides the answer herein by demonstrating clinically that at least part, if not all, of the epidermal cells are originated from regenerative epidermal stem cells. As shown in FIGS. 20B–G, these stem cells were stained positive for K-19 while the body underwent active tissue repair and skin regeneration. These regenerative epidermal stem cells proliferated and differentiated to produce specific types of keratinocytes capable of synthesizing other types of keratin, e.g., keratin type 9 and 16, which moved upward towards the epidermis. These differentiated cells continued to move upward and further differentiated to produce keratinocytes capable of synthesizing harder keratin (e.g., keratin type 1 and 10), which is the typical keratin of mature epidermal cells.

However, it should be noted that only the regenerative epidermal stem cells were labeled here by using K-19 as a detectable marker. Regenerative stem cells for other tissues, such as blood vessels, hair follicles, collagenous fiber, interstitium and nerves, were also activated, proliferate, and differentiate to produce all cells needed for regeneration of a fully functional organ in vivo and in situ (FIGS. 6 and 11).

The next question to be answered is: "where did the regenerative cells come from?" Under normal physiological conditions, some cells long stay at phase $G_o$ or $G_1$ of the cell cycle and their proliferation starts only when the condition becomes favorable. However, some cells proliferate continuously through out the body's life, thus demanding a continuous supply of stem cells. Part of the daughter-cells of stem cells differentiate to become mature, specialized cells and part of them keep their proliferation ability. For an intact, normal skin, stem cells in the basal layer of epidermis are capable of proliferating continuously. Newly proliferated cells move upward towards the epidermis. When reaching the deep area of the spinous layer, they proliferate again two or three times and then lose their proliferation ability.

As discussed above, in deep second and third degree burn wounds, epidermis and dermis deep layers are injured, and stem cells in the basal layer of epidermis are destroyed. Based on the observation of the wound healing process at both the cellular and the tissue levels, the inventor believes that the residual surviving mesenchymal cells around the follicles, sweat glands and capillaries in subdermal tissue may provide most, if not all, of the regenerative stem cells, including the multipotent epidermal stem cells.

Figure 30:
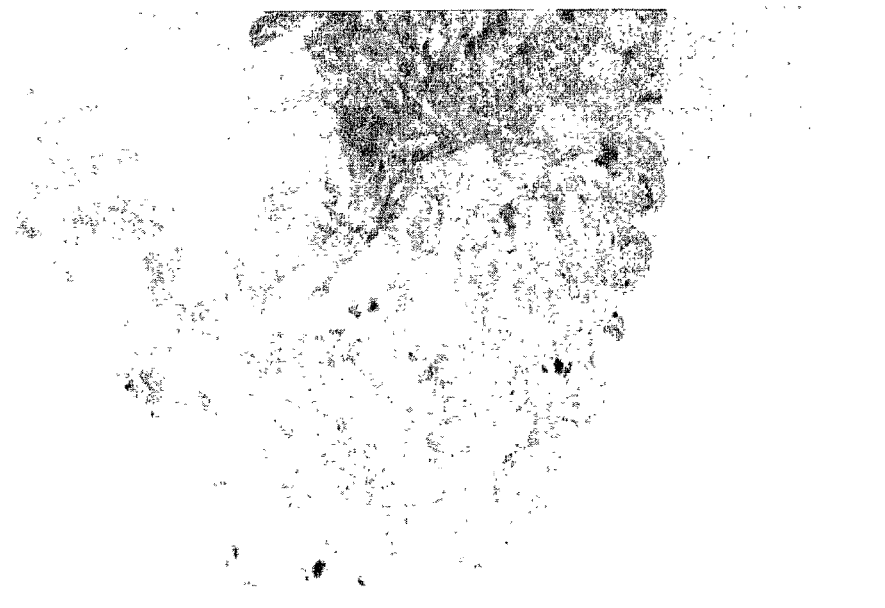
FIG. 30 shows a section of the skin of a patient suffering from full-thickness burn on the face.
Figure 31:
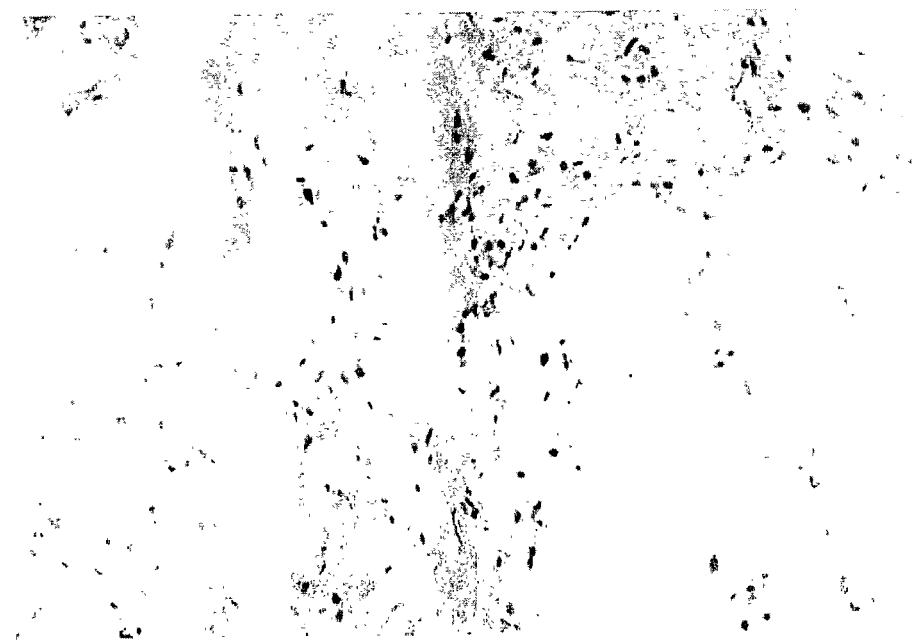
FIG. 31 shows that mesenchymal cells in the remaining viable tissues in the fatty layer of the hypodermis were activated and converted to adult stem cells (ASCs) in response to injury of the body and/or by the stimulation of the active ingredients in the inventive composition.
Figure 32:
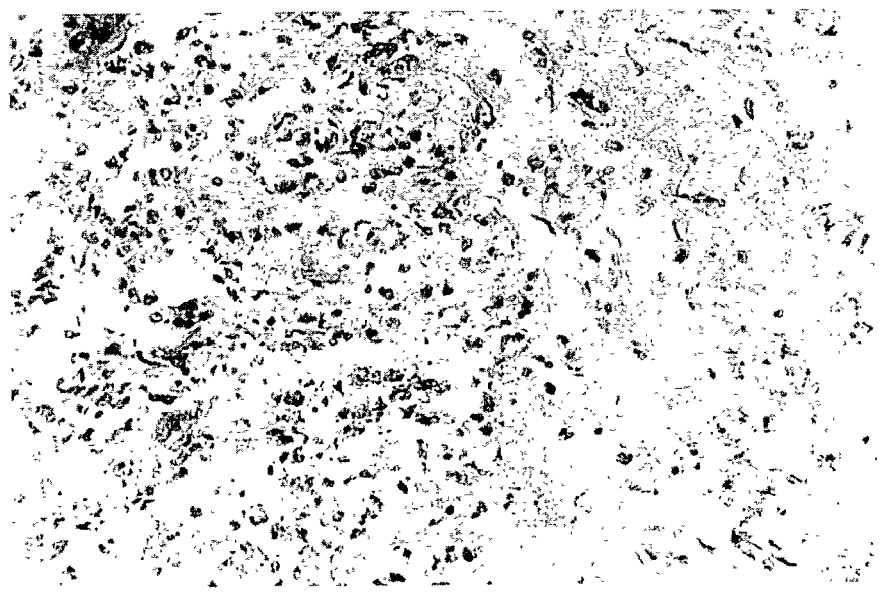
FIG. 32 shows that multipotent ASCs, under the regenerative conditions provided by the inventive composition, can be induced to differentiate directionally into various tissue stem cells for tissues.

This theory is supported by clinical data collected on another patient suffering from full-thickness burn on the face (FIG. 30). As shown in FIG. 31, the mesenchymal cells in the remaining viable tissues in the fatty layer of the hypodermis were activated and converted to adult stem cells (ASCs) in response to injury of the body and/or by the stimulation of the active ingredients in the inventive composition. These ASCs are multipotent, and under the regenerative conditions provided by the inventive composition can be induced to differentiate directionally into various tissue stem cells for tissues, such as dermis, epidermis, blood vessels, hair follicles, collagenous fiber, interstitium and nerves (FIG. 32). The tissue stem cells from their cognate organ communicate with each other following the genetic programs set up at the embryonic development stage and associate with each other in an organ-specific manner (FIGS. 33A and B).

Figure 34:
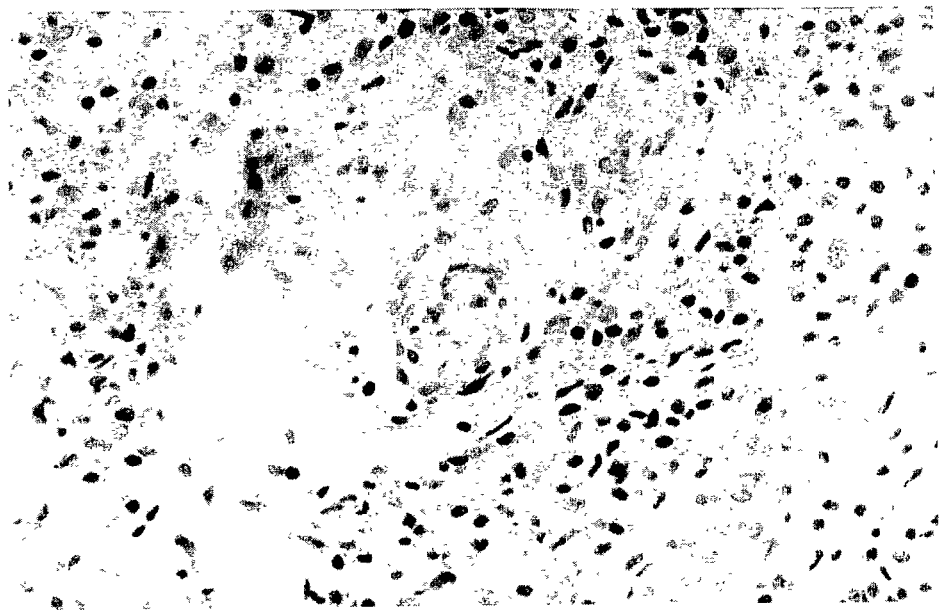
FIG. 34 shows the organ-specific association of blood vessels and nerves.
Figure 35:
FIG. 35 shows the formation of a hair follicle during the skin regeneration process under the conditions provided by using the methodology of the present invention.
Figure 36:
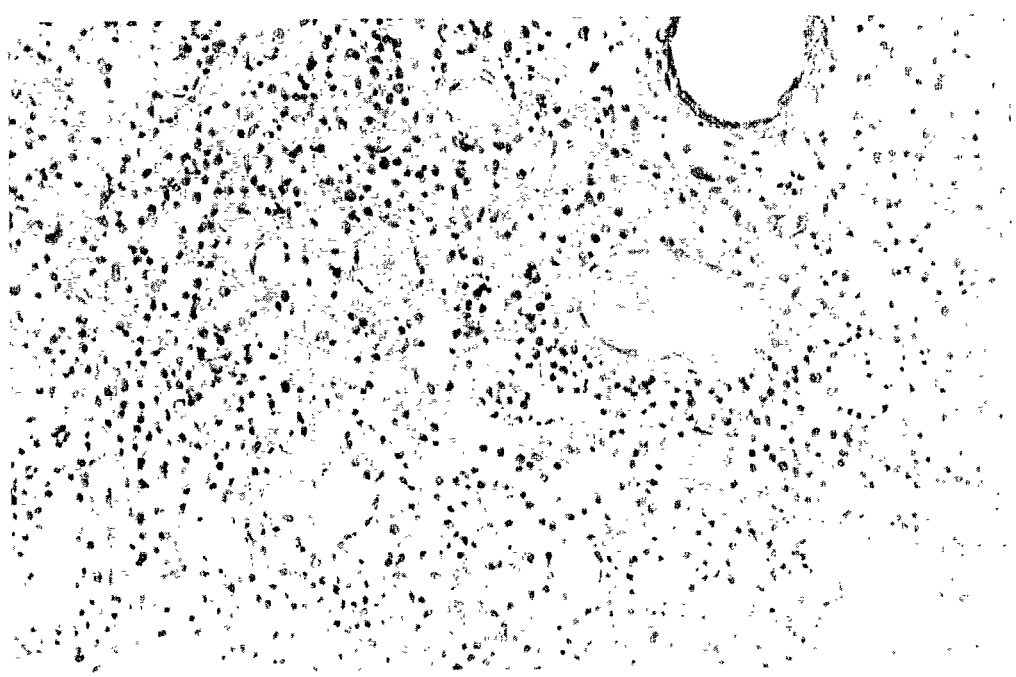
FIG. 36 shows that appendages of the skin including blood vessels, nerves and various glands were regenerated and assembled into the nascent skin.

These specialized tissue stem cells are cultivated under the regenerative conditions provided by the inventive composition to produce daughter stem cells, part of which are induced to differentiate tissue-specifically into various cells needed for regeneration of a fully functional organ in vivo and in situ. These cells communicate with each other by forming junctions specific and characteristic for their cognate tissue (e.g., the desmosome junctions between two echinocytes as shown in FIG. 28), which results in the regeneration of the nascent tissue. FIG. 34 shows the organ-specific association of blood vessels and nerves; and FIG. 35 shows the formation of a hair follicle during the skin regeneration process under the conditions provided by using the methodology of the present invention. The regenerated nascent tissues are cultivated under the favorable conditions provided by the inventive composition and communicate with each other by forming junctions specific and characteristic for their cognate organ, such as the hemidesmosome injunction between epithelial cells and the basement membrane as showed in FIG. 29. Further, these nascent tissues are assembled organ-specifically to constitute a nascent organ. As shown in FIG. 36, appendages of the skin including blood vessels, nerves and various glands were regenerated and assembled into the nascent skin. Finally the tissues in the nascent organ mature into their corresponding adult tissues which constitute the regenerated, fully functional organ. Through these cell-cell, cell-tissue and tissue-tissue communications within a live body, tissues and organs can be regenerated with restoration of their physiological structures and functions. For example, as demonstrated above, an adult who lost the epidermis and dermis in a significantly large area of her body can recover with new skin that is normal in both structure and function (FIG. 25).

These discoveries and inventions are significant theoretically and practically. First, they reveal for the first time that adult tissues and organs can be repaired and regenerated with restoration of full physiological functions through cultivation of stem cells in vivo and in situ. This outcome has been dreamed by scientists and physicians in the art but never achieved clinically. The inventor believes that although transplantation of stem cells cultivated in vitro has enjoyed limited successes in repairing damaged epidermis and dermis, the healing of the wounds is not physiological. In other words, the skin repaired by using the transplantation method sustains disfiguring scars and loss of physiological functions of the appendages such as hair follicles, apocrine and eccrine sweat glands. Microscopically, only in the present invention is demonstrated that junctions between cells in the same tissue and between neighboring tissues (e.g., between epidermis and dermis) are restored structurally and functionally to the full physiological extent. By contrast, junctions between tissues repaired by using other methods in the art are reconstructed pathologically, manifesting abnormal structures and functions.

Second, it is for the first time that multipotent embryonic stem cells are induced or activated in a fully developed human body during its self-tissue repair and organ regeneration. As shown above, a large number of regenerative stem cells on the wounds expressed K-19 during the physiological wound healing process directed by using the methodology of the present invention. It has been well acknowledged that keratin 19 is expressed in the basal cell layer of fetal epidermis and in the bulge of the developing hair of human fetuses. Thus the cultivation of these embryonic stem cells in vivo and in situ for adult tissue repair and organ regeneration is not only innovative in medicine but also has a profound impact on developmental and cell biology.

4. Formulation and Routes of Administration for Tissue Repair and Organ Regeneration The present invention provides novel compositions for pharmaceutical or nutraceutical use in an animal, preferably in a human.

In one aspect, compositions are provided for promoting cell growth, tissue repair and organ regeneration, preferably in vivo. It should be noted the compositions may be adapted for use in vitro as cell growth culture media or in ex vivo reconstruction of tissues and/or organs.

In one aspect of the invention, compositions are provided for promoting cell growth, tissue repair and organ regeneration, preferably in vivo and in situ. In one embodiment, the composition comprises a sterol compound dissolved in oil at a concentration at least 0.5% by weight based on the total weight of the composition, preferably a sterol compound dissolved in a fatty acid-containing oil at a concentration at least 1% by weight based on the total weight of the composition. In the composition, the sterol compound preferably forms ester with the fatty acid in the oil under suitable conditions such as high temperature (e.g., >100° C.).

The concentration of the sterol compound preferably ranges from about 1.2% to 40% by weight, more preferably about 1.2% to 20% by weight, and most preferably about 2% to 6% by weight.

The fatty acid-containing oil is preferably vegetable oil, more preferably vegetable oil selected from the group consisting of corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof, and most preferably sesame oil.

The fatty-acid is preferably selected from the group consisting of palmitic acid, linoleic acid, oleic acid, trans-oleic acid, stearic acid, arachidic acid, and tetracosanoic acid.

The sterol compound may be an animal sterol or a plant sterol (also called phytosterol). Examples of animal sterol include cholesterol and all natural or synthesized, isomeric forms and derivatives thereof. Preferably, the sterol compound is selected from the group consisting of stigmasterol, campesterol, β-sitosterol, chalinosterol, clionasterol, brassicasterol, α-spinasterol, daucosterol, avenasterol, cycloartenol, desmosterol, poriferasterol, and all natural or synthesized, isomeric forms and derivatives thereof. More preferably, the sterol compound is a combination of stigmasterol, β-sitosterol, and campesterol, collectively referred to herein as "sitosterol".

Optionally, the sterol compound is a combination of stigmasterol and β-sitosterol; a combination of brassicasterol and β-sitosterol; a combination of brassicasterol, stigmasterol and β-sitosterol; or a combination of campesterol, stigmasterol and β-sitosterol.

Although not wishing to be bound by the theory as to the mechanism of action of the sterol compound in tissue repair and organ regeneration, the inventor believes that the sterol compound may play important roles in inducing morphogenesis of the cells by changing the fluidity and permeability of the cell membrane. As a result, many cell membrane-associated proteins such as kinases and phosphotases may be activated to stimulate cell growth. It is also plausible that dormant stem cells may be activated due to morphogenic changes in the membrane. Further, differentiated adult tissue cells may also be induced to undergo transformation into a non-differentiated phenotype, i.e., the process called "dedifferentiation". With the change of permeability of the cell membrane, other mitogens and regulatory molecules may be more readily uptaken by the cells so as to stimulate a balanced growth of a wide variety of cells needed for physiological tissue repair and functional organ regeneration. Moreover, expression and phosphorylation of cell adhesion molecules (CAMs) may be stimulated, presumably due to activation of membrane-bound proteins during the morphogenesis process, thus further enhancing association of cognate cells to form a specific tissue, and assembly of cognate tissues to form a fully functional organ within the body.

The composition further comprises beeswax at a concentration ranging from about 1% to 20% by weight, more preferably from about 2% to 10% by weight, and most preferably from about 3% to 6% by weight.

Beeswax has long been used as an excipient for manufacturing drugs for external use. In traditional Chinese medicine, beeswax is a drug for detoxication, granulation promotion, for relieving pain and cardialgia and treating diarrhea, pus and bloody stool, threatened abortion with vaginal bleeding, septicemia, refractory ulcer and thermal injury ("A Dictionary of Chinese Materia Medica", in Chinese, "Zhong Yao Da Ci Dian", Science and Technology Press, Shanghai, 1986, page 2581).

The constituents of beeswax can be grouped into four categories, i.e., esters, free acids, free alcohols and paraffins. Beeswax also contains trace amount of essential oil and pigment. Among the esters, there are myricyl palmitate, myricyl cerotate, and myricyl hypogaeate. In free acids, there are cerotic acid, lignoceric acid, montanic acid, melissic acid, psyllic acid, hypogaeic acid and neocerotic acid. Among free alcohols, there are n-octacosanol and myricyl alcohol and in the paraffins, pentacosane, heptacosane, nonacosane and hentriacontane, and an olefin called melene. An aromatic substance called cerolein is also found in beeswax.

Beeswax in the inventive composition provides structural support to the sterol compound dissolved in oil. As described in detail in a later section of the Specification, beeswax can form a pigeonhole-like three-dimensional structure within which oil drops containing the sterol compound are enclosed. The dimension of at least 50% of the holes in the pigeon-hole like structure of beeswax formed in the composition is preferably below 50 micron, more preferably below 30 micron, and most preferably below 20 micron. In a particular embodiment, the dimension of at least 50% of the holes in the pigeon-hole like structure is between 10–50 micron.

When administered in an oral dosage form such as a soft gel capsule, beeswax may form a protection membrane on the mucosa of the GI tract and the oil drops contained in the "pigeonholes" may be released into the damaged site in a timed-release manner as the pigeonhole-structure collapses gradually.

Alternatively, the composition further comprises propolis at a concentration ranging from about 0.1% to 30% by weight, more preferably from about 1% to 20% by weight, and most preferably from about 5% to 10% by weight.

Propolis is known as a sticky, gum-like substance which is used to build the beehives. In intact propolis a variety of trace ingredients in form of a homogenous mixture with resins, beeswax, essential oils and pollens as predominant ingredients, as well as other ingredients such as flavonoids and phenol carboxylic acids. Natural propolis hardly dissolves in water and has a peculiar odor. Propolis can be prepared from beehives by extraction with organic solvents such as ethonol, ether and chloroform.

The composition preferably contains minimum amount of water, more preferably containing less than 0.5% of water by weight, and most preferably containing less than 0.1% water by weight.

For oral administration, the inventive composition can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated.

In a preferred embodiment, the inventive composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. More preferably, the inventive composition is contained in soft capsules. The inventive composition may be dissolved or suspended in suitable liquids, such as fatty oils or liquid polyethylene glycols. In addition, stabilizers may be added. All formulations for oral administration should be in dosages suitable for such administration.

Optionally, the inventive composition for oral use can be obtained by mixing the inventive compositioon with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal administration, the inventive compositions may take the form of tablets or lozenges formulated in conventional manner.

For administration by inhalation, the inventive composition for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

In another embodiment, the pharmaceutically acceptable composition comprises: a sterol compound dissolved in an injectable oil at a concentration at least 0.5% by weight. The concentration of the sterol compound preferably ranges from about 0.5% to 20% by weight, more preferably about 1% to 10% by weight, and most preferably about 2% to 6% by weight.

The injectable oil is preferably vegetable oil that has been processed to render it suitable for clinical injection into a human, preferably selected from the group consisting of corn oil, peanut oil, cottonseed oil, safflower oil, tea tree oil, sesame oil, olive oil or soybean oil, and most preferable soybean oil. Examples of the processed vegetable oil are described in U.S. Pat. No. 3,798,246 (using silica gel in combination with an eluting organic solvent), U.S. Pat. No. 4,101,673 (using silica gel or silicic acid), and U.S. Pat. No. 4,588,745; and in Min et al. (1972) J. Am. Oil Chem. Soc. 49:675–677, and Singleton et al. (1966) J. Am. Oil Chem. Soc. 43:592–595. The vegetable oil may be deodorized by passing it through silica gel, or acid clay, and then filtered.

For example, the injectable oil may be triglycerides obtained from the vegetable oil by following the method described in U.S. Pat. No. 4,588,745. Such an injectable oil is a triglyceride with each fatty acid in the ester having from 12 to 20 carbon atoms; having higher free fatty acid content; having reduced trilinolenin content; having reduced diglyceride content and reduced natural tocopherol content based on the starting oil.

In yet another embodiment, the composition suitable for parental administration comprises: a clinically accepted fatty emulsion having an oil phase and a sterol compound dissolved in the oil phase, the concentration of the sterol compound ranging from about 0.1% to 20% by weight.

It is to be understood that modifications to the sterol compound i.e. to include side chains also fall within the purview of this invention. It is also to be understood that this invention is not limited to any particular combination of sterols forming a composition. In other words, any sterol compound alone or in combination with other sterol compound in varying ratios as required depending on the nature of the ultimate formulation fall with the purview of this invention.

The sterol compound for use in this invention may be procured from a variety of natural sources. For example, phytosterol may be obtained from the processing of plant oils (including aquatic plants) such as corn oil, wheat germ oil, soy extract, rice extract, rice bran, rapeseed oil, sesame oil, and other vegetable oils, and fish oil. Without limiting the generality of the foregoing, it is to be understood that there are other sources of phytosterols such as marine animals from which the composition of the present invention may be prepared. For example, phytosterols may be prepared from vegetable oil sludge using solvents such as methanol. Alternatively, phytosterols may be obtained from tall oil pitch or soap, by-products of the forestry practice.

The clinically accepted fatty emulsion comprises at least one vegetable oil, preferably corn oil, peanut oil, safflower oil, sesame oil, olive oil or soybean oil. Clinically accepted fatty emulsions usable in the practice of the present invention include emulsions such as Liposyn, Soyacal, Intralipid or Travemulsion, for example. The formulation of the present invention is preferably essentially free of exogenous detergent.

To prepare the composition suitable for parental administration, it was desired to use commercially and medically accepted fat emulsions. Such emulsions were exemplified by INTRALIPID (Kabi-Vitrum of Emoryville, Calif. and Stockholm, Sweden); LIPOSYN (Abbott Laboratories, North Chicago, Ill.); SOYACAL (Alpha Therapeutic Corp., 555 Valley Blvd., Los Angeles, Calif.); and TRAVEMULSION (Travenol Labs, Inc., 1 Baxter Parkway, Deerfield, Ill.). These commercial fat emulsions for practical use in clinical medicine, were known to be acceptably safe and also to have a shelf storage life of up to two years or longer. Such medically useful and marketed fat emulsions generally contain 10–20% of a vegetable oil, which is commonly soybean oil, although safflower oil and other vegetable oils may be correspondingly useful and practical.

Alternatively, the sterol compound may be dissolved in a pharmaceutically-acceptable, water-miscible, non-fatty acid solvent and used for parental administration. Examples of such a solvent include, but are not limited to, N-methyl pyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (s)-(-)-ethyl lactate; acetone; glycerol; alkyl ketones such as methylethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

Solobilizers may also be used in conjunction with this type of solvent to render the sterol compound more soluble in solution. The solubilizers are typically amphiphiles—those molecules that have the dual properties of being both polar and non-polar—in the solution that have the ability to increase the solubility of materials that are normally insoluble or only slightly soluble, in the dispersion medium. Solubilizers often have surfactant properties. Their function may be to enhance the solubility of a solute in a solution, rather than acting as a solvent, although in exceptional circumstances, a single compound may have both solubilizing and solvent characteristics. Solubilizers useful in the practice of this invention include, but are not limited to, triacetin, polyethylene glycols (such as PEG 300, PEG 400, or their blend with 3350), polysorbates (such as Polysorbate 20, Polysorbate 40, Polysorbate 60, Polysorbate 65, or Polysorbate 80), poloxamers (such as Poloxamer 124, Poloxamer 188, Poloxamer 237, Poloxamer 338, or Poloxamer 407), polyoxyethylene ethers (such as Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether), polyoxylstearates (such as Polyoxyl 30 stearate, Polyoxyl 40 stearate, Polyoxyl 50 stearate, Polyoxyl 100 stearate), polyethoxylated stearates (such as a polyethoxylated 12-hydroxy stearate), and Tributyrin. In a preferable embodiment, pharmaceutically-acceptable solubilizers are excluded from the inventive composition. In another preferable embodiment, polyoxyethylated castor oil is excluded from the inventive composition.

The inventive composition may further comprise baicalin, preferably at a concentration ranging from about 0.1 to 2% by weight, more preferably about 0.2 to 1% by weight, and most preferably about 0.5% to 1% by weight. Baicalin may have anti-inflammatory effects on the damaged or diseased tissue, which helps providing a low inflammation environment for organ regeneration, mimicking that in scarless wound healing of a fetus at its early gestation stage. It might also be possible that baicalin might bind to cell membrane receptors for polysaccharides such as selectin and further promote cell adhesion.

Baicalin may be obtained by extracting huangqin (*Scutellaria baicalensis* Georgi) in oil, alcohol or other organic solvent, preferably in oil at temperature higher than 100° C., more preferably between about 120–200° C., and most preferably between about 160–180° C. Preferably, the root of huangqin is used and may be obtained from the plant selected from one or more members of the group of *Scutellaria viscidula* Bge, *Scutellaria amoena* C. H. Wright, *Scutellaria rehderiana* Diels, *Scutellaria ikonnikovii* Juz, *Scutellaria likiangensis* Diels and *Scutellaria hypericifolia* Levl of Labiatae Family. Dictionary of Chinese Materia Medica, Shanghai Science and Technology Press, 1988, pages 2017 to 2021.

The inventive composition may further comprise obaculactone (also called limonaic acid), preferably at a concentration ranging from about 0.1 to 2% by weight, more preferably about 0.2 to 1% by weight, and most preferably about 0.5% to 1% by weight. Obaculactone may be obtained by extracting huangbai (*Phellodendron amurense* Rupr) in oil, alcohol or other organic solvent, preferably in oil at temperature higher than 100° C., more preferably between about 120–200° C., and most preferably between about 160–180° C. Alternatively, obaculactone may also be obtained by extracting huangbai in alcohol such as ethanol. Preferably, the bark of huangbai is used and may be obtained from the plant selected from one or more members of the group of Phellodendron chinense Schneid, Plellodendron chinense Scheid var. glabriusculum Schneid, Phellodendron chinense Schneid var. omeiense Huang, Phellodendron Schneid var. yunnanense Huang and Phellodendron chinense Schneid var. falcutum Huang. A Dictionary of Chinese Materia Medica, Shanghai Science and Technology Press, 1988, pages 2031 to 2035.

Optionally, the inventive composition may further comprise obabenine, preferably at a concentration ranging from about 0.001% to 2% by weight, more preferably about 0.002% to 0.5% by weight, and most preferably about 0.003% to 0.1% by weight.

Obabenine may be obtained by extracting huangqin, huangbai, and/or huanglian (coptis chinensis Franch) in oil, alcohol or other organic solvent. Root of huanglian is preferably used. Huanglian may be selected one or more from the group of Coptis deltoidea C. Y. Cheng et Hsiao, *Coptis omeiensis* (Chen) C. Y. Cheng, and *Coptis teetoides* C. Y. Cheng of Ranunculaceae Family. A Dictionary of Chinese Materia Medica, Shanghai Science and Technology Press, 1988, pages 2022 to 2030.

Also optionally, the inventive composition may further comprise an extract of heshouwu (*Polygonum multiflorum* Thunb which belongs to the family of Polygonacea), preferably the root tuber of heshouwu (Radix polygoni multiflori). Its common name in English-speaking countries is Fleeceflower Root and is known in China as Heshouwu, Shouwu, or Chishouwu.

Heshouwu can be harvested in autumn and winter when leaves wither, washed clean, and the large one cut into pieces, and then dried to produce a dried heshouwu. Heshouwu can also be prepared by steaming (e.g., for 3 hr) to produce a steamed heshouwu, optionally in the presence of wine to produced the so-called wine-processed heshouwu. The slices or pieces of heshouwu may be mixed with thoroughly with black bean juice and stewed in a suitable non-ferrous container until the juice is exhausted.

The mixture is dried to solidify and then cut into slices to produce the so-called prepared heshouwu.

Crude heshouwu and prepared heshouwu may differ in the composition. It is known that all kinds of heshouwu contain free phosphatidylcholine (lecithin), phosphatidylinositol, phosphatidylcholine, phosphatidylethanolamine (cephalin), N-free phosphatidylethanolamine and sphingolipids. Crude heshouwu usually contains 3.7% phospholipids, and higher than processed heshouwu. Heshouwu also contains emodins such as anthraquinones or anthrones which mainly glycoside with glucose and rhamnose to form mono- or di-glycoside, chrysophanol, emodin, rhein, chrysophanol ester, and chrysophanin acid anthrone. Processed heshouwu has a lower concentration of anthraquinones. Heshouwu also contains tetrahydroxystilbene glycoside and its analogues, and the processed heshouwu have slight higher concentration. Heshouwu is abundant of trace elements, such as calcium, iron, manganese, copper, and zinc at a concentration of about 421 ug/g, tens times higher than most herb. In addition, heshouwu has high concentration of starch, soluble amylose, vitamins, amino acids, and coarse fat.

Also optionally, the inventive composition may further comprise berberine, preferably at a concentration ranging from about 0.001% to 2% by weight, more preferably about 0.002% to 0.5% by weight, and most preferably about 0.003% to 0.1% by weight.

Also optionally, the inventive composition may further comprise narcotoline, preferably at a concentration ranging from about 0.001% to 2% by weight, more preferably about 0.002% to 0.5% by weight, and most preferably about 0.003% to 0.1% by weight.

Obabenine, berberine and narcotoline alone or in combination may suppress pain in the damaged tissue by inhibiting smooth muscle contraction.

Optionally, the inventive composition may further comprise various amino acids, preferably all 20 natural amino acids (e.g., alanine, asparagines, aspartic acid, cysteine, glutamic acid, glutamine, glycine, phenylalanine, histidine, isoleucine, lysine, leucine, methionine, proline, arginine, serine, threonine, valine, tryptophan, and tyrosine), for providing nutrition support to cell growth. The amino acids may be chemically synthesized or obtained from natural sources. For example, a full spectrum of natural amino acids may be obtained by extracting earthworms, a rich source of protein/amino acids, in oil or alcohol.

In a particular embodiment, the inventive composition further comprises an extract of earthworm in an amount of 10–90% by weight based on the total weight of the composition, wherein the amount of earthworm is 2–60% by weight based on the total weight of the oil.

The inventive composition may further comprise nucleic acid bases such as adenine, cytidine, guanine, thymine and uridine.

In another aspect of the invention, a method of repairing a damaged tissue or organ is provided. The method comprises: administering to a mammal having a damaged or diseased tissue or organ a pharmaceutically acceptable composition comprising a sterol compound dissolved in oil at a concentration at least 0.5% by weight, such that the physiological structure and function of the tissue or organ are substantially restored.

In one embodiment, a method is provided for treating a wound of the skin, bone, mucus, tendons, muscles or connective tissue in a mammal, preferably a human. The method comprises: administering in vivo to said mammal at the site of the wound a composition comprising a fatty acid-containing oil at a concentration at least 10% by weight based on the total weight of the composition; and a sterol compound added to and dissolved in said oil at a concentration at least 1% by weight based on the total weight of the composition. The concentration of the sterol compound preferably ranges from about 1.2% to 40% by weight, more preferably about 1.2% to 20% by weight, and most preferably about 2% to 6% by weight based on the total weight of the composition. The pharmaceutically acceptable composition may be any of the inventive compositions described above.

The method may further comprise: liquefying a necrotic tissue of the wound; and removing the liquefied necrotic tissues from the wound site without surgical debridement.

The method may be used to treat acute wounds such as a wound resulted from physical trauma, thermal, wind, frost, optical or electric injury.

The method may also be used to treat chronic wounds such as chronic surface ulcer, diabetic ulcer, decubital ulcer, chronic wound as a result of a lower limb vascular disease, chronic wound as a result of poor blood flow, wound due to cancer or cancer metastasis, erosion caused by bacterial or viral infection, herpes simplex corneal ulcer, subcutaneous tissue ulcer, radiation-caused skin ulcer, vaginitis, cervical erosion, gingivitis, wounds due to dilation and enlargement of veins, and hemorrhoid.

For a chronic wound, the method may further comprise: debriding the chronic wound before administering the composition to the wound. The debridement may include surgically removing necrotic tissues from the wound or chemically removing necrotic tissues from the wound, while avoiding injury to the viable tissue surrounding the wound site.

According to the method, the composition may be administered topically to the wound, for example, at least three times a day in a sufficient amount to such that the wound site is maintained moist. The moist level is preferably maintained between 1–5 folds of the physiological moist level of a normal human body. Optionally, the composition is in a form of ointment and is administered in a sufficient amount to cover the wound at a thickness of 0.5–5 mm of the ointment, preferably a thickness of 1–3 mm of the ointment.

The present invention also comprises a method for preparing a stable and non-toxic formulation suitable for parenteral administration to an animal. This method involves thoroughly mixing a clinically accepted fatty emulsion having an oil phase with an amount of the sterol compound sufficient to result in a formulation at the concentration ranging from about 0.1% to 20% by weight, preferably from about 0.2% to 15%, more preferably from about 1% to 10%, and most preferably about 3% to 6%. The thorough mixing may be accomplished by many means well-known in the field and may, for example, involve sonication or repeated passage through a small orifice such as that of a syringe needle.

The inventive composition is suitable for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

In another aspect, compositions are provided for reducing pain in an animal by a novel mechanism of action. The inventor discovered that reversible inhibition of the contraction of smooth muscles can reduce pain caused by various reasons, such as trauma and burns. In an in vitro experiment, small intestines from a mouse were obtained immediately after beheading, cut into to 7 1-cm fragments, and immersed in normal saline. The rate of contraction of the intestine fragments was at 6 times/min in average. With the addition of the inventive composition into the saline, contraction of the intestine fragments gradually slowed down, eventually stopped. However, when these intestine fragments were removed from the saline containing the inventive composition to normal saline, contraction resumed. The inventive composition can also inhibit contraction of arrectores pilorum connected to the upper part of a vellus hair follicle and located in the area of dermis close to the basal layer. In the clinic, application of inventive composition effectively reduced the pain of patients suffering from trauma and burns.

In one embodiment, the inventive composition for pain reduction comprises alkaloids selected from the group consisting of narcotoline, papaverine, coptisine, phellodendrine, obabenine, berberine, lumbricin and combinations thereof. For example, narcotoline and papaverine may be obtained by extracting dry capsules of poppy (*Papaver somniferam* L.) in alcohol, oil, or other solvents. Coptisine may be obtained by extracting the root of huanglian in alcohol, oil, or other solvents. Phellodendrine and berberine may be obtained by extracting the bark of huangbai in alcohol, oil, or other solvents. Obabenine may be obtained by extracting huanglian, huangbai, and/or huangqin in alcohol, oil, or other solvents. Lumbricin may be obtained by extracting the root of huanglian in alcohol, oil, or other solvents.

In a preferred embodiment, the composition comprises alkaloids extracted from huanglian, huangbai, and huangqin. Optionally, the composition may further comprise narcotoline extracted from poppy capsule. Alternatively, the composition is substantially free of narcotoline, e.g., contains less than 0.01%, preferably less than 0.001% of narcotoline.

The inventive composition may be used to reduce pain in various part of the body. For example, it may be applied topically to reduce pain of the skin caused by trauma, bruise, burns and various other assaults through inhibition or relaxation of the contraction of arrectores pilorum in the injured dermis. It may also be administered locally to internal organs suffering from pain caused by infection, trauma and other reason through inhibition or relaxation of the contraction of smooth muscles.

The inventive compositions may be administered or coadministered orally, topically, parenterally, intraperitoneally, intravenously, intraarterially, transdermally, sublingually, intramuscularly, rectally, transbuccally, intranasally, via inhalation, vaginally, intraoccularly, via local delivery (for example by catheter or stent), subcutaneously, intraadiposally, intraarticularly, or intrathecally.

In a preferred embodiment, the inventive composition is administered locally to a site where the damaged or diseased tissue/organ is located via various routes of administration, such as transdermally, intramuscularly, by catheter or stent, intraperitoneally, intraarterially and vaginally. The inventive composition may also be administered or coadministered in slow release dosage forms.

In a more preferred embodiment, the inventive composition is administered directly and locally to the tissues of the diseased or damaged organ. For example, the inventive composition comprising sterol dissolved in injectable oil may be directly injected into heart muscles and be directly taken up by the cells of these tissues without going through blood vessels. This approach is similar to the nerve block therapy where local anesthetics such as lidocaine are injected directly to the target tissue via a block needle.

Alternatively, other delivery systems for hydrophobic pharmaceutical compounds may be employed to deliver the inventive composition. Liposomes and emulsions are well known examples of delivery vehicles or carriers for hydrophobic drugs. In a preferred embodiment, long-circulating, i.e., stealth liposomes are employed. Such liposomes are generally described in Woodle, et al., U.S. Pat. No. 5,013,556, the teachings of which are hereby incorporated by reference.

Optionally, the inventive composition may be administered in a targeted drug delivery system, for example, in a liposome coated with an antibody targeting the tissue/organ to be repaired or regenerated, such as a tumor-specific antibody. Such liposomes will be targeted to and taken up selectively by the site of interest (e.g., tumor cell).

Also optionally, the inventive composition may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the inventive compositions for a few weeks up to over 100 days.

Via various routes of administration in vivo and in vitro, the inventive compositions and methods described above have a wide variety of applications in biology and medicine.

Morphologically, the inventive compositions and methods may be used to activate dormant adult stem cells (ASCs) or to induce transformation of adult tissue cells into ASCs in vivo, as well as in vitro. Further, these inventive compositions may be used to induce tissue-specific morphogenesis of cells to render morphological changes of the cells, which may lead to dedifferentiation of cells, i.e., reversion of a differentiated cell to a non-differentiated cell (stem cell). In addition, they can also be used to inhibit toxicity of bacteria, presumably through modulation the structure and function of the bacterial membrane and alteration of the bacterial cell cycle.

Intracellularly, the inventive compositions may be used to activate various enzymes such as kinases and phosphatases and signaling molecules such as cAMP which play important roles in cell growth and differentiation, and thus support the growth of cells and maintain the balance of various types of cells to ensure repair and regeneration of physiologically functional tissues and organs.

Intercellularly, the inventive compositions may be used to promote tissue-specific association of cells of the same or different type, presumably through stimulation of expression and activation of various cell adhesion molecules (CAM) such as connexin and cadherin to form various physiological junctions.

At the tissue level, the inventive compositions may be used to promote organ-specific assembly of tissues by promoting formation of physiological junctions between these tissues.

In human and veterinary medicine, the inventive compositions may be used in the treatment of various conditions caused by injury, diseases and aging. As shown clinically, the methodology disclosed in the present invention was used to regenerate or clone a new organ through cultivation of regenerative stem cells in vivo and in situ, i.e., at the site where the original organ resides. Such an innovative approach promises to revolutionize the field of regenerative medicine, benefit the human health and improve the quality of life.

5. Method and Composition for Removing Necrotic Tissue with Minimum Injury to Viable Cells The present invention also provides methods and compositions for removing necrotic tissues or cells with minimum injury to remaining viable cells in the diseased or damaged tissue or organ.

In a diseased or wounded tissue cells undergo a serious of biochemical reactions in response to various signals from the microenvironment and often die as a result. There are two modes of cell death: necrosis and apoptosis. Necrosis is the common mode of death for cells that are wounded by physical forces such as thermal injury or by acute, exogeneous chemical damage to the tissue. Apoptosis or programmed cell death, on the other hand, is the mode of death taken by cells in through their intrinsic genetic programs of suicide in response to signals such as chemotherapeutics and expression of apoptosis regulatory proteins.

Regardless of the mode of cell death, the dead cells in the tissue need to be discharged in order to promote regeneration of tissue. If the necrotic cells remain in the diseased or the wounded site, various biochemical products from these cells will trigger inflammatory response of the body, which in turn inhibits the tissue regeneration and induces damage to the remaining viable cells.

In contrast to the conventional method of surgical debridement of the eschar or necrotic tissues, the present invention provides an innovative approach to solving the problems faced by many physicians in treating wounds and ulcers. Traditional surgical debridement often leads to secondary surgical injury to the viable tissues which are critical for tissue repair and organ regeneration according to the present invention. Enzymatic debridement with proteases also has cytotoxic effects on viable cells in general.

According to the present invention, necrotic tissues are removed through liquefaction and subsequent exudation out of the damaged site. To achieve these effects, novel compositions with unique 3-dimensional (3D) physical structure.

In one embodiment, a non-invasive method for debriding a necrotic tissue in a mammal, preferably a human, is provided. The method comprises:

administering in vivo to said mammal at the site of the necrotic tissue a composition comprising a fatty acid-containing oil at a concentration at least 10% by weight based on the total weight of the composition; a sterol compound added to and dissolved in said oil at a concentration at least 1% by weight based on the total weight of the composition; and a wax at a concentration at least 1–20% by weight based on the total weight of the composition, wherein the wax in the composition forms a pigeon-hole like structure at ambient temperature or below;

liquefying at least 20% of the necrotic tissue; and removing the liquefied necrotic tissues from the mammal without surgical debridement.

According to the method, the necrotic tissue may be liquefied without substantially damaging the viable tissues in the mammal. Preferably, at least 80% of the viable tissues immediately adjacent to the necrotic tissue is still viable after liquefaction of the necrotic tissue. More preferably, at least 90% of the viable tissues immediately adjacent to the necrotic tissue is still viable after liquefaction of the necrotic tissue.

Figure 37:
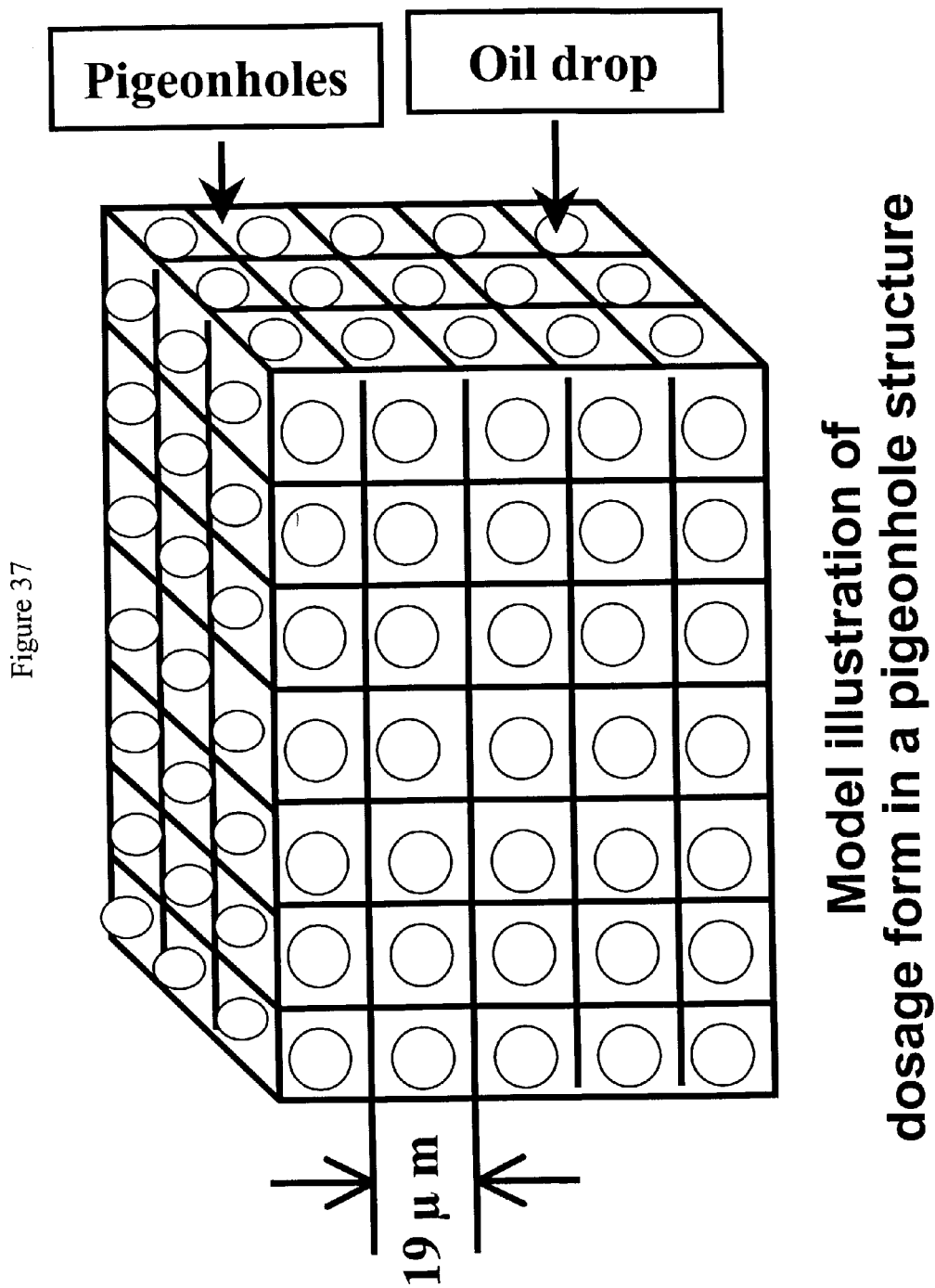
FIG. 37 illustrates a model structure with beeswax forming the pigeonholes and oil drops enclosed therein.

The inventor has designed the pigeonhole-like structure by exploiting the differential thermo-physical properties of beeswax and oil. Beeswax melts when heated to about 70–80° C. The melted beexwax is then mixed with oil such as animal or vegetable oil (e.g., soybean, sesame, and corn oil) and allowed to gradually cool down to ambient temperature (i.e. 20–25° C.). Since beeswax cools down much faster than oil the solidified wax forms a 3-dimensional structure with small "pigeonholes" within which oil drops are enclosed. FIG. 37 illustrates a model structure with beeswax forming the pigeonholes and oil drops enclosed therein. Ideally, the oil drops are separately enclosed in the holes and not contacting each other. The dimension of the holes in average is preferably 5–50 $\mu$m, more preferably 10–30$\mu$m, and most preferably 15–20 $\mu$m.

Figure 38:
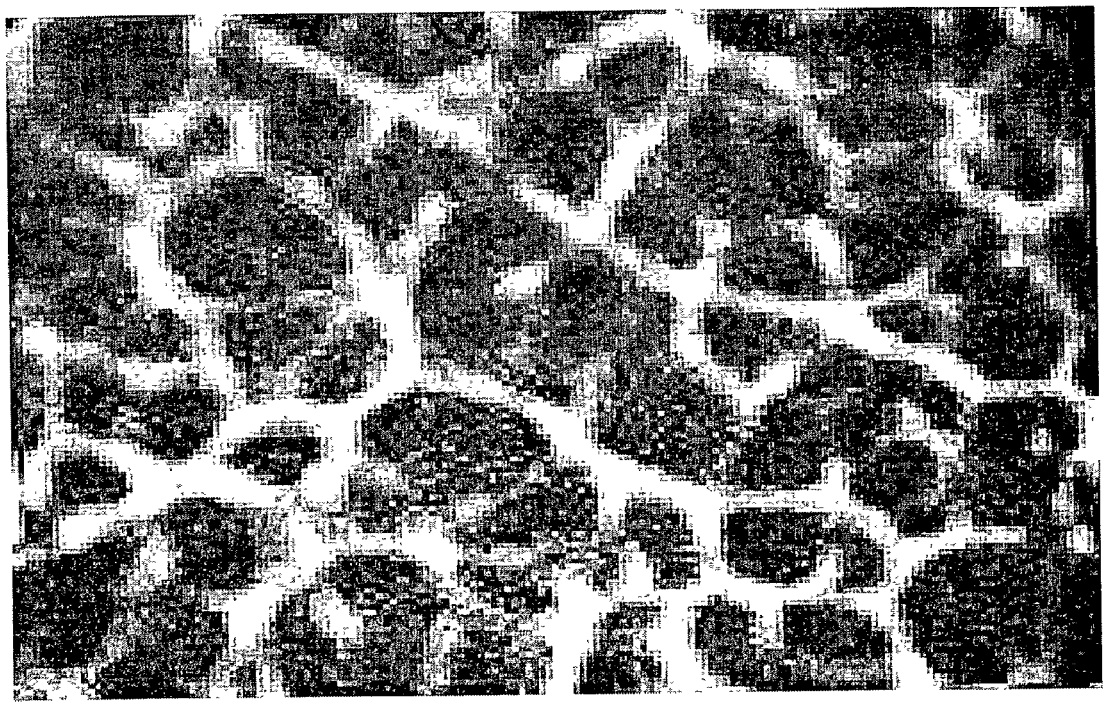
FIG. 38 shows an electronograph of an embodiment of the composition comprising about 10% beeswax and about 90% sesame oil.

FIG. 38 shows an electronograph of an embodiment of the composition comprising about 10% beeswax and about 90% sesame oil. As shown in FIG. 38, beeswax indeed forms a pigeonhole structure in 3D and has individual oil drops enclosed therein.

To maintain the structural integrity, the composition contains minimum amount of water, preferably less than 1% by weight, more preferably less than 0.1% by weight, and most preferably less than 0.01% by weight.

Figure 39:
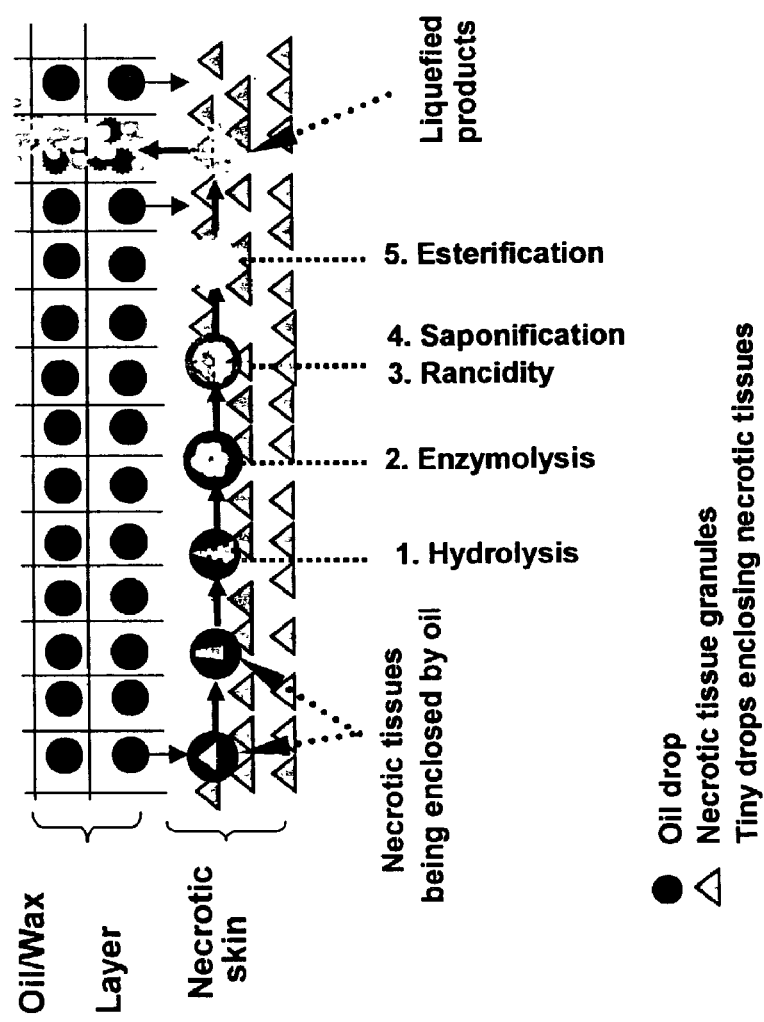
FIG. 39 illustrates that when the composition is applied to a damaged tissue such the wound site of a burn patient, a serious of biochemical reactions occur as a result of the release of the oil from the pigeonholes formed by beeswax.

The unique structure of the composition plays significant roles in its use for removing necrotic tissues through liquefaction. When the composition is applied to a damaged tissue such the wound site of a burn patient, a serious of biochemical reactions occur as a result of the release of the oil from the pigeonholes formed by beeswax (FIG. 39). While not wishing to be bound by the exact molecular mechanisms as to the reactions, the inventors believes that at least five types of biochemical reactions between the oil and the necrotic tissues occur at the wound site, including hydrolysis, enzymolysis, rancidity, saponification, and esterification.

Figure 40:
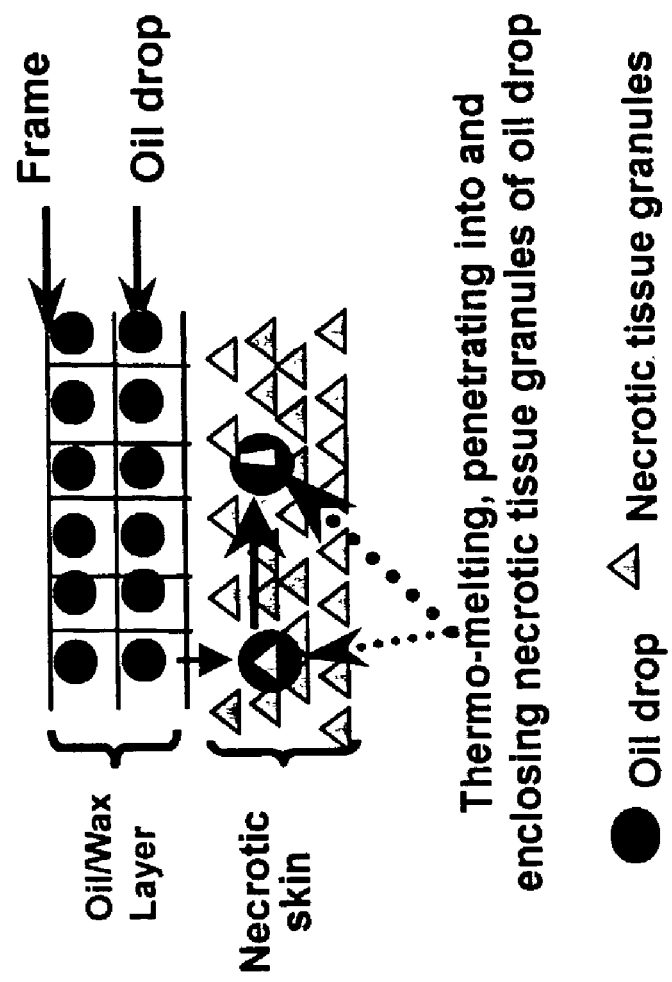
FIG. 40 illustrates that when the composition is applied to the wound site, the part of the structure contacting the wound is warmed up by the body temperature (about 37° C.) and started to break down to release the enclosed oil drops.

First, when the composition is applied to the wound site, the part of the structure contacting the wound is warmed up by the body temperature (about 37° C.) and started to break down to release the enclosed oil drops (FIG. 40). The released oil penetrates into the tissues of the wound site and encloses the granules of necrotic tissues within.

Figure 41:
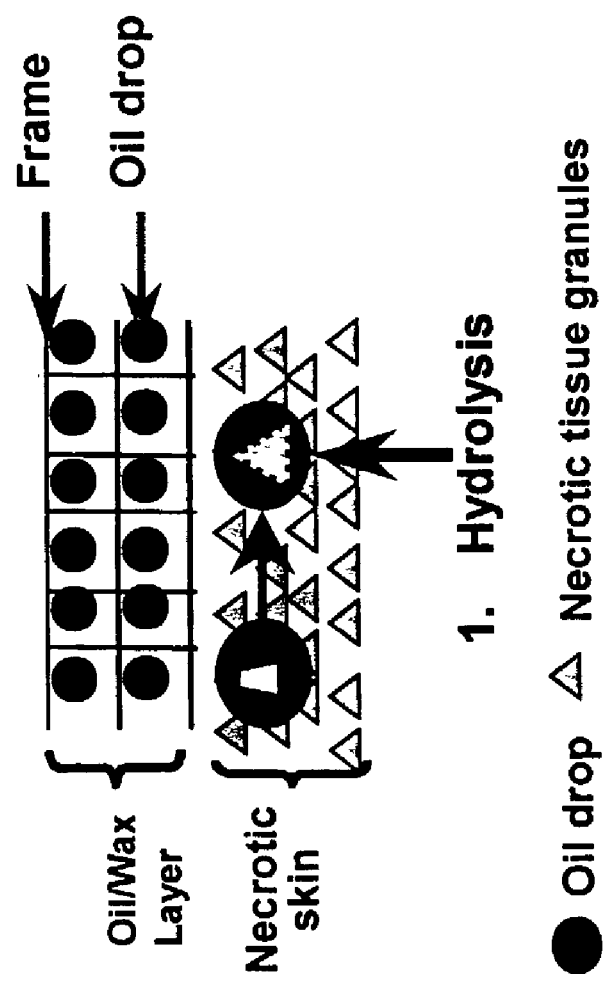
FIG. 41 illustrates that the enclosed necrotic tissue enclosed by oil undergoes hydrolysis of the cells and various enzymes from the cells are released as a result.

Second, the enclosed necrotic tissue enclosed by oil undergoes hydrolysis of the cells (FIG. 41) and various enzymes from the cells are released as a result.

Figure 42:
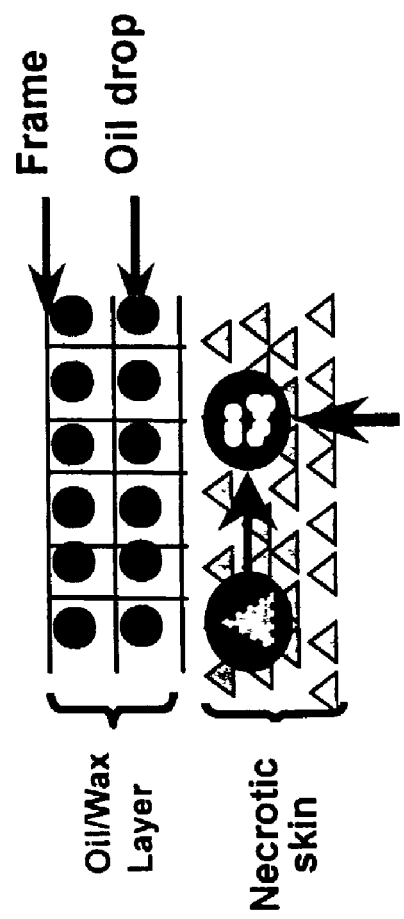
FIG. 42 illustrates that the cellular enzymes released further digest the necrotic tissue granules enclosed by the oil.

Third, the cellular enzymes released further digest the necrotic tissue granules enclosed by the oil (FIG. 42).

Figure 43:
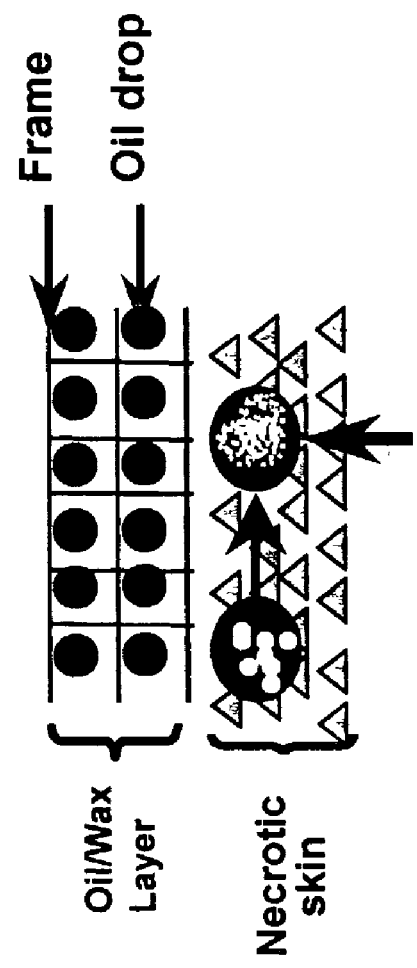
FIG. 43 illustrates that through rancidity and saponification between the digested tissue and the oil, the solid tissue granules are liquefied.

Fourth, through rancidity and saponification between the digested tissue and the oil, the solid tissue granules are liquefied (FIG. 43).

Figure 44:
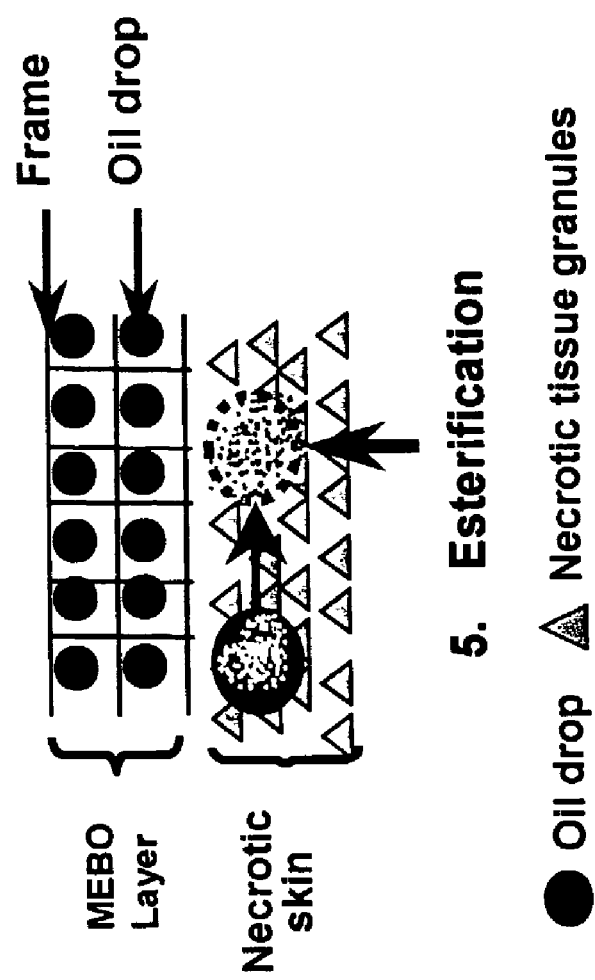

Fifth, through esterification of the liquefied tissue, active ingredients that may have been esterified by the fatty acid in oil can be released to the wound site (FIG. 44).

Figure 45:
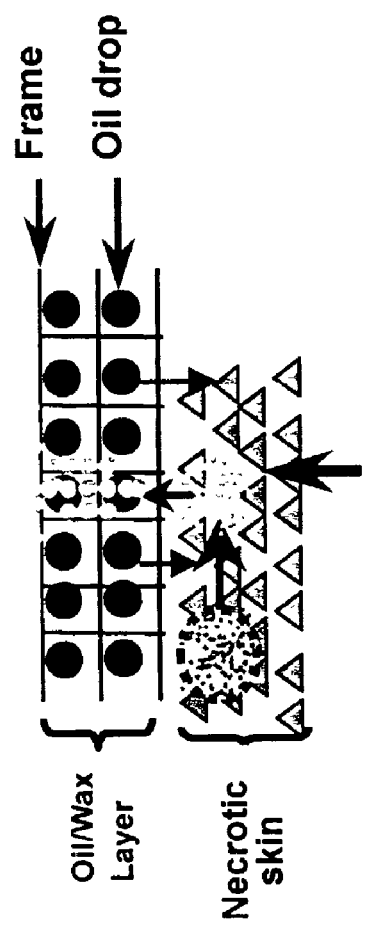
FIG. 45 illustrates that through esterification of the liquefied tissue, active ingredients that may have been esterified by the fatty acid in oil can be released to the wound site.

Finally, with the gradual breakdown of the pigeonhole structure of the composition, more oil together with active ingredients therein is released to the wound site to enclose the residual necrotic tissue granules. Meanwhile, the liquefied necrotic tissue is forced to exude with the breakdown of the pigeonhole structure due to its incompatibility with the remaining viable tissues (FIG. 45).

By this unique mechanism of action of the inventive composition, the solid necrotic tissues that are difficult to be removed by following traditional methods such as surgical debridement are transformed into liquid that is automatically drained out of the wound sit, leaving the viable tissues intact.

This noninvasive approach is extremely advantageous in several aspects. First, the necrotic tissues are quickly removed and thereby are prevented from inducing inflammatory response of the body. Second, with the effective removal of the necrotic tissues, the conditions favorable for bacteria growth are destructed, thus dramatically reducing the risk of bacteria infection.

Figure 46:
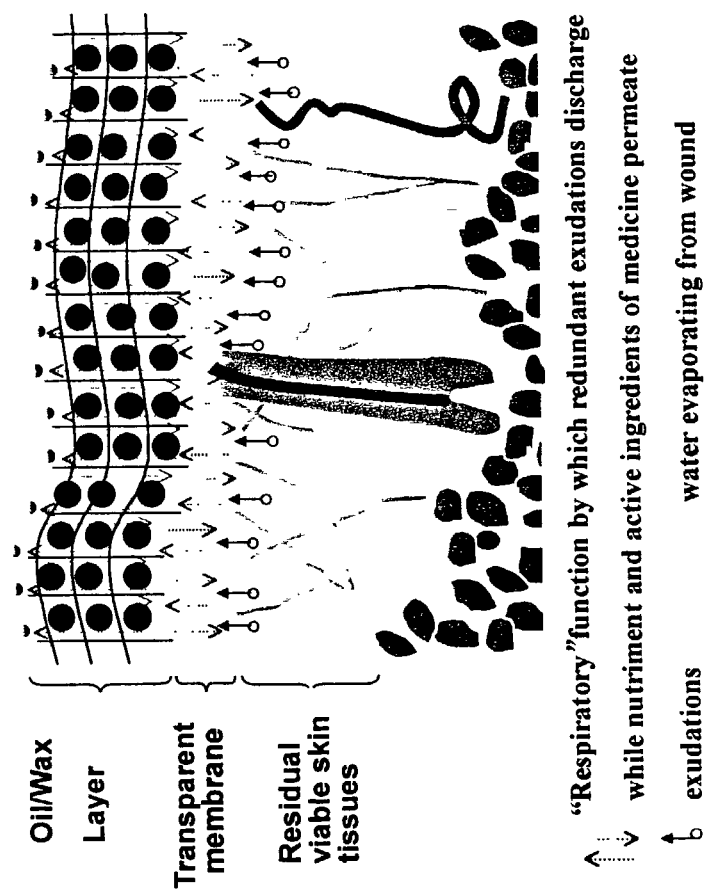
FIG. 46 illustrates that a transparent proteinous membrane forms on the surface of the viable skin tissues.

More importantly, the remaining viable tissues are not enclosed by the oil; instead, are protected by a layer of almost transparent membrane formed on their surface when the necrotic tissues are completely removed. As illustrated in FIG. 46, a transparent proteinous membrane forms on the surface of the viable skin tissues, through which active ingredients in the composition can permeate into the viable tissue to promote regeneration while the metabolic wastes and other exrecta can be discharged. This membrane acts as a protective layer isolating the fragile, nascent tissues that are undergoing active regeneration from the hostile environment outside. In a way, it serves as a substitute for the epidermis to protect the vital tissues in the dermis from environmental assaults. As illustrated in FIG. 46, this membrane has a "respiratory" function which allows active discharging of metabolic waste and intaking of nutrients and oxygen into the regenerating cells and tissues.

Figure 47:
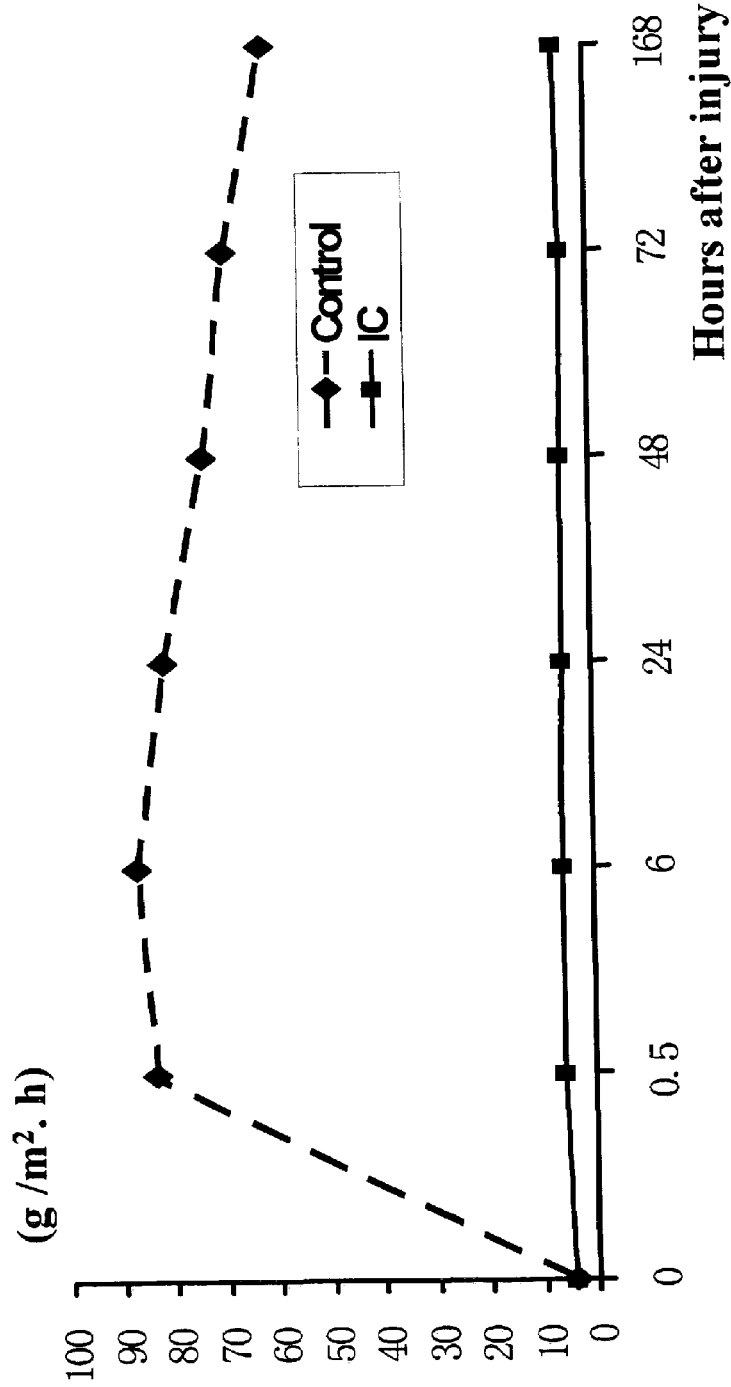
FIG. 47 is a plot indicating that burn wounds of rabbits that were exposed to open air undergo active evaporation of water, causing overdrying of the wound.
Figure 48:
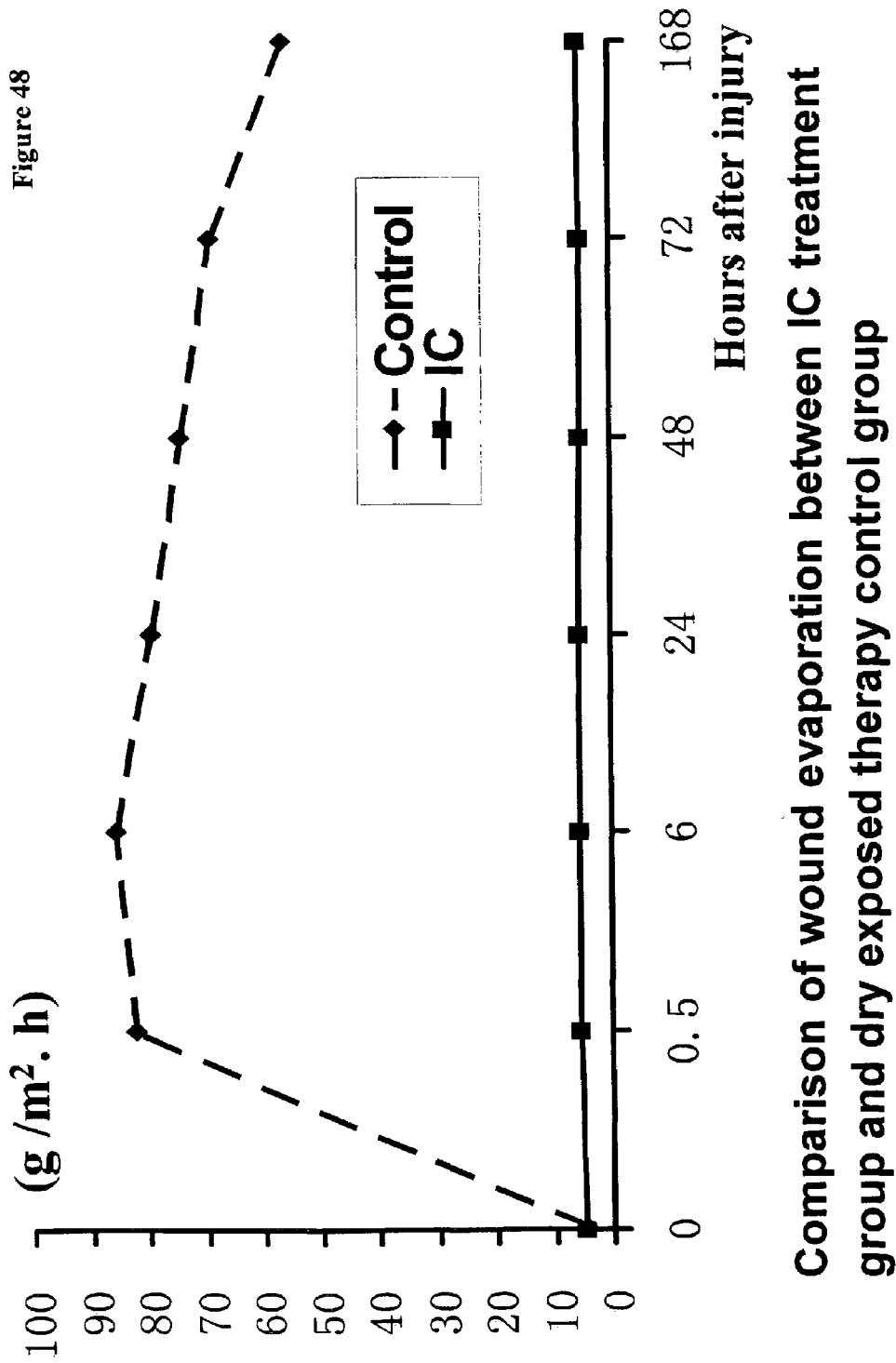
FIG. 48 is a plot indicating that evaporation of wounds treated by using the conventional dry therapy, i.e., with exposure to heat to hasten drying, was at much higher levels than those treated with the inventive composition.

In addition, the wound site is kept in a physiological moist environment due to the unique structure formed by beeswax having oil drops enclosed therein. The structure with tiny pigeonholes isolates the wound from the environment, prevents the wound from overdrying and yet allows active "breathing" of the viable tissues underneath. As shown in FIG. 47, burn wounds of rabbits that were exposed to open air undergo active evaporation of water, causing overdrying of the wound. In contrast, evaporation of the wound treated by the inventive composition (IC) was much less and was kept at a physiologically lower level. Similar to the auto-control group, evaporation of wounds treated by using the conventional dry therapy, i.e., with exposure to heat to hasten drying, was at much higher levels than those treated with IC (FIG. 48).

Figure 49:
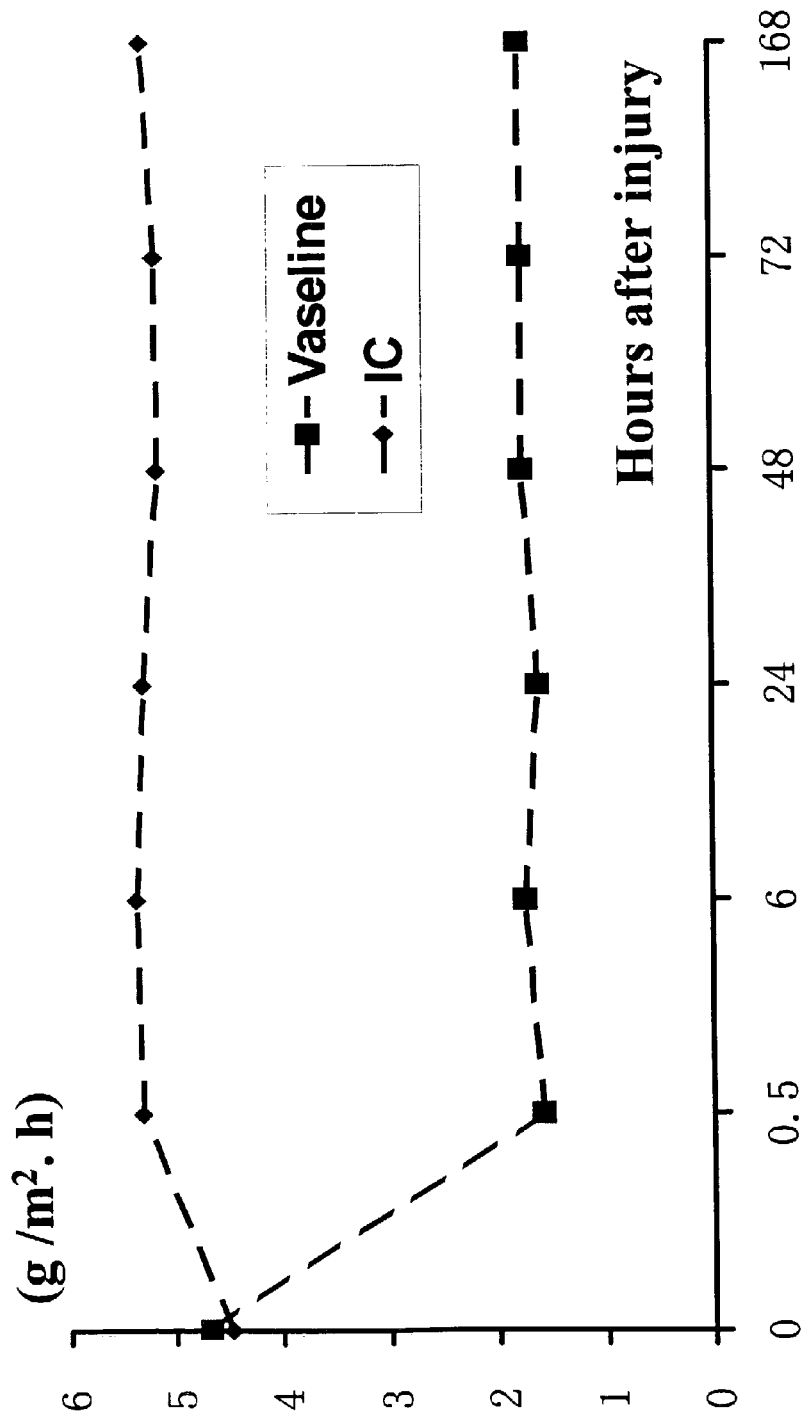
FIG. 49 is a plot indicating that evaporation of the wounds covered with Vaseline was inhibited at levels twice as low as those covered by the inventive composition.

Importantly, the inventive composition, while keeps the wound site in a physiologically moist environment, does not cause excess drenching of the tissues as Vaseline does. As compared in FIG. 49, evaporation of the wounds covered with Vaseline was inhibited at levels twice as low as those covered by the IC. Physiologically, as compared in FIGS. 50A and B, the burn wound of a rabbit treated with the IC was moist and liquefied within 48 hours gradually from the outer layer to the inner layers (FIG. 50A). In contrast, the burn wound of the rabbit covered by Vaseline is drenched, showing signs of dislodging of tissues; and the normal skin surround the wound also suffered excessive drenching. Observed under the microscope, for the wound treated by the dry therapy there was infiltration of inflammatory cells between the necrotic tissues and the viable tissues (FIG. 51A). In contrast, for the wound treated by the inventive composition there was only mild infiltration of inflammatory cells in the junction between the necrotic tissues and the viable, and slight dilation and congestion of micro blood vessels (FIG. 51B). In the wound treated by Vaseline tissue vacuolation and infiltration of inflammatory cells at 48 hours post burn (FIG. 51C). As also shown in a table in FIG. 52, the wound healing time of the rabbits treated by the IC was much faster (15 days) than the control without any treatment (20 days). These results demonstrate that the inventive composition with its unique 3D structure is capable of replacing skin as a protective layer and maintaining the physiologically moist environment of the skin.

It should be noted that compositions that are made with material other than beeswax to adopt a pigeonhole structure that enclose oil drops therein are also within the purview of the present invention.

The inventive composition may serve as a base for a wide variety of pharmaceuticals, nutraceuticals and cosmetics. Many active ingredients may be dissolved or suspended in oil, the drops of which are then enclosed in the pigeonholes formed by beeswax. The resultant dosage forms may be administered topically, orally, via inhalation or other suitable routes of administration.

6. Controlling Microbial Infection with Minimum Injury to Vial Tissues

The present invention also provides a method for controlling microbial infection in the skin or mocusal tissue of a mammal, preferably a human. The method comprises: administering in vivo to said mammal at the site suspected of infection a composition comprising a fatty acid-containing oil at a concentration at least 10% by weight based on the total weight of the composition; and a sterol compound added to and dissolved in said oil at a concentration at least 1% by weight based on the total weight of the composition.

According to the method, the sterol compound may be esterified by the fatty acid in the oil in the composition. The concentration of the sterol compound is preferably 1.2–40% by weight, more preferably about 1.2–20% by weight, and most preferably 2–6% by weight.

The sterol compound is preferably a phytosterol. Examples of the phytosterol compound include, but are not limited to, stigmasterol, campesterol, β-sitosterol, chalinosterol, clionasterol, brassicasterol, α-spinasterol, daucosterol, desmosterol, avenasterol, cycloartenol, poriferasterol, and natural or synthesized, isomeric forms and derivatives thereof. In particular, the sterol compound is more preferably a combination of stigmasterol and β-sitosterol, a combination of brassicasterol and β-sitosterol, a combination of brassicasterol, stigmasterol and β-sitosterol, or a combination of campesterol, stigmasterol and β-sitosterol.

Also according to the method, the microrobial infection may be infection of bacteria, fungus, virus, or a combination thereof. s In particular, the method may be used for inhibiting toxicity of a wide spectrum of bacteria. Compared to conventional methods of using antibiotics and alcoholic antiseptics, the present inventive approach is directed toward a completely different mode of bacteria inhibition. In general, the bacterial cells need not undergo cell death immediately following application of the inventive composition. Instead, bacterial cells are still capable of genetic replication and yet the toxicity of bacteria is severely inhibited by the inventive composition's intervention with the bacterial cell division and thus the production of toxin. According to extensive cell biological and microscopic studies, this inhibitory effect is achieved by modulating the morphology and cellular structures of bacterial cells and by changing the ecology of bacterial growth.

Bacterial cells are prokaryotic cells that form the simplest organisms found in most natural environments. Typical bacterial cells adopt spherical or rod shapes, usually several microns (i.e., micrometers) in linear dimension. The structure of a bacterial cell is quite simple. Beneath a protective coat called cell wall, a plasma membrane encloses a single cytoplasmic compartment containing DNA, RNA, protein, and small molecules.

Bacteria can replicate rapidly following a mode of cell replication called binary fission. Under optimal conditions, a single bacterial cell can divide every twenty minutes and thereby give rise to 5 billion cells in less than 11 hours. Certain types of bacteria exert their toxicity to animal through production of bacterial toxin which triggers the infected host animal's immune response, causing inflammation and damage of organs. Bacterial infection, if not controlled timely, can result in severe organ damage and sometimes death of the infected host.

The most common way of inhibiting bacteria is through bactericidal effects of antibiotics. Many antibiotics are made by fungi in order to prevent bacterial infection. Almost all of the known antibiotics exert their bactericidal effects through interference with bacterial cell cycle at the gene replication level. Rifamycin, for example, inhibits bacterial gene replication at the stage of transcription from DNA to RNA. Rifamycin can block initiation of RNA chains by binding to RNA polymerase. However, most of the antibiotics interfere with bacteria growth at the translation stage of gene replication. These antibiotic bind to different regions of bacterial ribosome, thereby inhibiting different steps in the protein synthetic process. For example, streptomycin prevents the transition from translational initiation complex to chain elongating ribosome and also causes miscoding. Tetracycline blocks binding aminoacyl-tRNA to the A-site of ribosome. During the polypeptide chain elongation of protein synthesis, the carboxyl end of the polypeptide chain is uncoupled from the tRNA molecule in the P-site of the small ribosomal subunit and joined by a peptide bond to an amino acid linked to the tRNA molecule in the A-site. This central reaction of protein synthesis is catalyzed by a peptidyl transferase. Chloramphenicol can block the peptidyl transferase reaction on ribosomes. When the new peptidyl-tRNA in the A-site is translocated to the P-site as the ribosome moves exactly three nucleotides along the mRNA molecule. This step requires energy and is driven by a series of conformational changes induced in one of the ribosomal components by the hydrolysis of a GTP molecule. Erythromycin can block this translocation reaction on ribosomes. These drugs exploit the structural and functional differences between prokaryotic and eucaryotic ribosomes so as to interfere with the function of prokaryotic ribosomes preferentially.

However, some antibiotics can act on both prokaryotes such as bacteria and eukaryotes such as mammal at the stage of gene translation. For example, puromycin can cause premature release of nascent polypeptide chains by its addition to growing chains end. Actinomycin D, on the other hand, interfere with gene transcription by binding to DNA and blocking the movement of RNA polymerase in order to inhibit RNA synthesis.

Another common way of killing bacteria is to apply alcohol, such as ethanol or isopropanol, onto the surface to be treated, such as a wound site. Alcohol can be very effective in killing bacteria, probably by causing instant, necrotic cell death through complete disruption of bacterial cell wall. These alcoholic reagents, however, are not selective in terms of cell killing and can be too harsh as to injure the nascent, fragile regenerative cells in the wound site.

In contrast to the conventional approach employing antibiotics and antiseptics, the present invention discloses a novel way of inhibiting toxicity of bacteria through a non-bactericidal mechanism of action. Inventive compositions are provided that comprise an animal sterol or phytosterol dissolved in oil at a concentration at least 0.5% by weigh. The concentration of the sterol compound preferably ranges from about 0.5% to 20% by weight, more preferably about 1% to 10% by weight, and most preferably about 2% to 6% by weight.

While not wishing to be bound by the exact mechanism of action by which the inventive composition inhibits bacterial toxicity, the inventor proposes in the present invention that an animal sterol or phytosterol, once incorporated into the membranes of bacterial cells, may change the structure and fluidity of the bacterial membranes, leading to morphologically changes of the cells. Morphogenesis of the bacterial cells causes a serious of biophysical and biochemical changes in the bacteria, possible by inhibition of cell division and production of bacterial toxin.

This hypothesis is supported by a bulk of experimental evidence. In vitro experiments were conducted on culture media containing various types of bacteria, including *Bacilius tetani, Bacteroides fragilis, Propionibacterium acne, Candida albicans, Bacillus proteus, E. coli*, and *Pseudomonas aeruginosa.*

FIGS. 53A–C show the morphological changes of the cells of *Bacilius tetani* growing in a culture medium containing the inventive composition. FIG. 53A shows the normal morphology of *Bacilius tetani* cells adopting a slender rod-like shape. The 1–2 generation of *Bacilius tetani* cells cultured in the medium containing the inventive composition adopted a long rod or filament shape (FIG. 53B). The 3–4 generation of *Bacilius tetani* cells showed greater variation in length, many having spores of drumstick shape (indicated by arrows), and a few long rod or filament shape (FIG. 53C).

FIGS. 54A-C show the morphological changes of the cells of *Bacteroides fragilis* growing in a culture medium containing the inventive composition. FIG. 54A shows the normal morphology of *Bacteroides fragilis* cells with a moderate size. The 3–4 generation of *Bacteroides fragilis* cells cultured in the medium containing the inventive composition had various lengths and the colonies fused together (FIG. 54B). The 5–6 generation of *Bacteroides fragilis* cells adopted a sphere or egg shape and many colonies fused to from irregular spheres (FIG. 54C).

FIGS. 55A and B show the morphological changes of the cells of *Propionibacterium acne* growing in a culture medium containing the inventive composition. FIG. 55A shows the normal morphology of *Propionibacterium acne* cells adopting a slend, short rod shape. In contrast, the 3–4 generation of *Propionibacterium acne* cells cultured in the medium containing the inventive composition adopted various longer, bulkier rod or filament shapes (FIG. 55B).

FIGS. 56A–C show the morphological changes of the cells of *Candida albicans* growing in a culture medium containing the inventive composition. FIG. 56A shows the normal morphology of *Candida albicans* cells in egg shape and with many blastospores. The 3–4 generation of *Candida albicans* cells cultured in the medium containing the inventive composition adopted a rounder shape in various sizes and there were some stick-shaped fungi with few blastospores observed (FIG. 56B). The 5–6 generation of *Candida albicans* cells adopted a stick or long rod shape and bacterial filaments had various lengths and few blastospores were observed (FIG. 56C).

FIGS. 56D and E show the results of germ tubes tests conducted on *Candida albicans* cells. Normal *Candida albicans* cells produced germ tubes at a rate of 90% (FIG. 56D). In contrast, the germ tube production rate of the 5–6 generation of *Candida albicans* cells grown in a culture medium containing the inventive composition was only 0.5–2% (FIG. 56E).

FIGS. 57A and B show the morphological changes of the cells of *Bacillus proteus* growing in a culture medium containing the inventive composition. FIG. 57A shows the normal morphology of *Propionibacterium acne* cells adopting a slend, short rod shape. In contrast, the 1–2 generation of *Bacillus proteus* cells cultured in the medium containing the inventive composition adopted a much longer, bulkier rod or filament shape (FIG. 57B).

FIGS. 58A and B show the morphological changes of the cells of E. coli growing in a culture medium containing the inventive composition. FIG. 58A shows the normal morphology of E. coli cells adopting a short rod shape. In contrast, the 5–6 generation of E. coli cells cultured in the medium containing the inventive composition adopted a much longer, bulkier rod or filament shape (FIG. 58B).

FIGS. 59A and B show the morphological changes of the cells of Pseudomonas aeruginosa growing in a culture medium containing the inventive composition. FIG. 59A shows the normal morphology of Pseudomonas aeruginosa cells adopting a short rod shape. In contrast, the 5–6 generation of Pseudomonas aeruginosa cells cultured in the medium containing the inventive composition adopted various longer rod or filament shapes (FIG. 59B).

These results confirmed that the inventive composition is capable of inducing morphological changes of bacterial cells while not causing immediate death of the cells. The cells continued to replicate genetically and yet appeared to change the invasiveness of the bacteria. This mode of action is in sharp contrast with those by antibiotics which generally inhibit genetic replication at the transcription and translation levels.

To demonstrate that the inventive composition not only induced morphological changes in bacteria but also altered its toxicity, in vitro experiments were conducted to test the effects of the IC on plasma-coagulase of Staphylococcus aureus. As shown in the table in FIG. 60, the control cell culture had high activity of the enzyme and the liquid was clear with many large bacteria clots. In contrast, enzymatic activity of the cells growing in the medium containing the IC was gradually reduced. By the 7–8 generation there was very few, small bacteria clots in the turbid culture. As shown in FIG. 61, there was a dosage response of the bacteria to various concentration of the IC. At lower concentrations it took a longer time for bacteria to have reduced plasma-coagulase activity.

The effects of the inventive composition on the proliferation of Staphylococcus aureus and Pseudomonas aeruginosa was determined. As shown in FIG. 62, After the $10^{th}$ generation of these two types of bacteria there was about 20–30 reduction in the total number of bacteria.

Although the bacterial cell number did not decrease dramatically, the invasiveness of these treated with the IC was significantly reduced. As also shown in FIG. 62, pathological examination of animals reveals the difference. In the subcutaneous tissue of the control animal there were congestion and edema, infiltration of inflammatory cells and suppurative zone, indicating a full-blown infection of Pseudomonas aeruginosa. In contrast, in the subcutaneous tissue and striated muscles of the animal infected with the bacteria there was infiltration of a few inflammatory cells without suppurative phenomenon.

As shown above, the inventive composition containing sterol in oil is capable of not only inducing dramatic changes of the morphology of bacteria and but also significantly reducing the toxicity and invasiveness of the bacteria with killing them. As also shown in animal and clinical trials of inventive compositions containing sterol, toxicity of bacteria on the wound was dramatically inhibited while nascent, regenerative animal cells could coexist with the bacteria and still grew rapidly to ensure speedy tissue repair and organ regeneration in vivo.

The inventor believes that a bacterial cell has a differential response to the incorporation of sterol into its membrane. The difference in membrane composition and fluidity may account for the differential responses in morphological changes and the cell cyclebetween eukaryotic and prokaryotic cells.

In prokaryotic cells such as bacteria, division of the DNA and of the cytoplasm are coupled in a direct way. When DNA replicates, the two copies of the chromosome are attached to specialized regions of the plasma membrane and are separated gradually by the growth of the membrane between. Fission takes place between the two attachments, so that each daughter cell captures one chromosome.

Gram-negative bacteria such as E. coli, have double membranes: the inner plasma membrane and the outer membrane. Between the inner and outer lipid bilayer membranes there is highly porous, rigid peptidoglycan composed of protein and polysaccharide that constitutes the bacterial cell wall; it is attached to lipoprotein molecules in the outer membrane and fills the periplasmic space. This space also contains a variety of soluble protein molecules. Gram-positive bacteria such as staphylococci and streptococci have single membranes but thicker cell walls. Their single membrane is analogous to the inner (plasma) membrane of gram-negative bacteria.

The bacterial membrane is formed by lipid bilayers, the universal basis for cell-membrane structure. Membrane lipids are amphiphilic molecules that are insoluble in water but dissolve readily in organic solvents. They constitute about 50% of the mass of most animal cell membranes, nearly all of the remainder being protein. The most abundant are the phospholipids that have a polar head group and two hydrophobic hydrocarbon tails. The tails are usually fatty acids, and they can differ in length (normally containing 14–24 carbon atoms). Differences in the length and satuation of the fatty acid tails are important because they influence the ability of phospholipid molecules to pack against one another, and for this reason they affect the fluidity of the membrane.

The lipid bilayer is a two-dimensional fluid which allows individual lipid molecules to diffuse freely within lipid bilayers. The precise fluidity of cell membranes is biologically important. Certain membrane transport processes and enzymatic activities, for example, can be shown to cease when the bilayer viscosity is increased beyond a threshold level. The fluidity of a lipid bilayer depends on both its composition and temperature. Bacteria, yeast, and other organisms whose temperatures fluctuate with that of their environment adjust the fatty acid composition of their membrane lipids so as to maintain a relatively constant fluidity.

Eucaryotic plasma membrane contain especially large amounts of cholesterol—up to one molecule for every phospholipid molecule. The cholesterol molecules enhance the permeability-barrier properties of the lipid bilayer. They orient themselves in the bilayer with their hydroxyl groups close to the polar head groups of the phospholipid molecules; their rigid, plate-like steroid rings interact with and partly immobilize those regions of the hydrocarbon chains that are closest to the polar head groups. By decreasing the mobility of the first few CH2 groups of the hydrocarbon chains of the phospholipid molecules, cholesterol makes the lipid bilayer less deformable in this region and thereby decreases the permeability of the bilayers to small water-soluble molecules.

The plasma membranes of most eucaryotic cells are varied, no only in containing large amounts of cholesterol, but also in containing a mixture of different phospholipids. Four major phospholipids predominate in the plasma membrane of many mammalian cells: phosphatidylcholine, sphingomyelin, phosphatidylserine, and phosphatidylethanolamine.

In contrast, bacterial plasma membranes are often composed of one main type of phospholipid and contain no cholesterol. The mechanical stability of these membranes is enhanced by the overlying cell wall. Thus, incorporation of animal sterol such as cholesterol or phytosterol such as sitosterol changes the normal composition and structure of the bacterial membrane, resulting changes in fluidity and permeability. Bacterial cell division may be inhibited as a result of changes in fluidity, manifesting as the growth of giant or elongated cells without reduction in DNA replication.

This unique mechanism exerted by the sterol may be exploited to provide novel antibacterial compositions having a wide variety of uses in pharmaceutical, nutraceutical, cosmetics and regular household reagents such as mouthwash, toothpaste without causing side effects as an antibiotic often does.

7. Composition for Promoting Stem Cell Growth in Vitro

The present invention also provides methods and compositions for culturing eukaryotic cells in vitro, such as human cells. In particular, a method is provided for culturing stem cells in vitro. The method comprises: contacting a culture of stem cells with a composition comprising a fatty acid-containing oil at a concentration at least 10% by weight based on the total weight of the composition; and a sterol compound added to and dissolved in said oil at a concentration at least 1% by weight based on the total weight of the composition.

The method may further comprise: removing waste in the cell culture after at least 1 day of culturing in the presence of the composition; and adding the composition to the culture again to maintain the growth of the stem cells.

According to the method, the stem cells may be included in one or more tissue pieces (e.g., skin pieces) immersed in the culture. The tissue may be isolated from an adult or fetal mammal, or from human foreskin.

Optionally, the stem cells may be embryonic stem cells of a vertebrate, preferably a mammal, and more preferably a human.

Also according to the method, the composition may further comprise baicalin, preferably at a concentration ranging from about 0.001 to 2% by weight based on the total weight of the composition, or an extract of huangqin huangqin in an amount of 10–90% by weight based on the total weight of the composition, wherein the amount of huangqin is 2–60% by weight based on the total weight of the oil.

In addition to the composition, the culture of stem cell may further include a regular tissue culture medium such as DMEM, MEM, etc.

The compositions and methods may be used to promote cell growth without involvement of mutagenesis or the action of transforming genes. Preferably, the cells in the culture may divide without limit and are prevented from differentiation.

The compositions and methods may also be used to establish primary cell lines with transferring heterologous genes into the cells. Primary cultures are prepared from the tissue of an organism, either with or without an initial cell-fractionation step. In most cases, cells in primary cultures can be removed from the culture dish and used to form a large number of secondary cultures; they may be repeatedly subcultured in this way for weeks or months. Such cells often display many of the differentiated properties appropriate to their origin: fibroblasts continue to secrete collagen; cells derived from embryonic skeletal muscles fuse to form giant muscle fibers that spontaneously contract in the culture dish; nerve cells extend axons that are electrically excitable and make synapses with other nerve cells; and epithelial cells form extensive sheets with many of the properties of an intact epithelium. However, primary cultures usually die after 50 generations under normal conditions. As demonstrated in the experiment on mouse skin cells growing in a culture medium containing the inventive composition (Example 2, FIG. 15A-D), the cells could proliferate without showing any abnormal or transformed phenotype.

The composition may be added to the regular tissue culture medium at an amount suitable for grow a specific type of cells or tissue(s). Although tissue culture media contain specified quantities of small molecules such as salts, glucose, amino acids and vitamins, most media also include a poorly defined mixture of macromolecules in the form of horse serum or fetal calf serum or a crude extract made from chick embryos. Serum-free, chemically-defined media include various growth factors for cell survival and proliferation in culture. This type of media also include transferrin which carries iron into cells. Also other protein signaling molecules that are essential for the survival, development, and proliferation of specific cell types.

The inventive composition may further some or all of the compositions of a typical medium suitable for the cultivation of mammalian cells. Examples of these reagents for tissue culture include, but are not limited to, a) Amino acids such as arginine, cystine, glutamine, histidine, isoleusine, leucine, lysine, methionine, phenylalanine, threonine, tryptophan, tyrosine, and valine; b) Vitamins such as biotin, choline, folate, nicotinamide, pantothenate, pyridoxal, thiamine, and riboflavin; c) Salts such as NaCl, KCl, NaH2PO4, NaHCO3, CaCl2, and MgCl2, d) Proteins such as insulin, transferrin, specific growth factors; and e) Miscellaneous: glucose, penicillin, streptomycin, phenol red, whole serum.

EXAMPLE

Example 1

Manufacturing Process of an Embodiment of the Inventive Composition

The following is a description the manufacturing process of an embodiment of the inventive composition according to the present invention.

First, raw materials for the production of the composition were purified according to industrial standards. Sesame oil was filtered and transferred to an oil tank. Roots of the plant huangqin (Radix Scutellariae) were washed, cut into small pieces, pulverized, sieved, and transferred into a stock tank. Beeswax was purified by aqueous decoction.

Second, the purified sesame oil was added to a reaction tank and heated at 140–160° C. for 20 minutes with stirring, and huangqin prepared above, huangbai, and earthworm was added to the reaction tank containing sesame oil, each at a weight ratio of 10 kg:100 kg. The mixture of huangqin and sesame oil was stirred and heated at 150–160° C. for 20–30 minutes. The dreg was filtered and discarded, and the clear oil filtrate was retained.

Third, sitosterol isolated from rice bran oil with 85–90% purity was added to the oil filtrate prepared above at a weight ratio of 5:95 and stirred at 140–150° C. for 15–20 minutes.

Fourth, purified beeswax was added to the oil filtrate containing sitosterol prepared above at a weight ratio of 10:90, and stirred at 130–140° C. for 10–15 min. This mixture was cooled to ambient temperature to produce the inventive composition (abbreviated the "IC").

Example 2

Growth of Mammalian Cells in Culture Media Containing the Inventive Composition

In this example, in vitro experiments were designed to demonstrate that the inventive composition has unique activities in promoting proliferation and tissue-specific adhesion of normal differentiated mammalian cells and mammalian stem cells, as well as maintaining the integrity of skin structure. Skin tissue cells, hair follicle stem cells and skin pieces were sampled from rats or mice and cultured in vitro. The cell or tissue culture is divided into two groups: the control group cultured in normal cell culture media (complete MEM) and the treatment group cultured in complete MEM with the addition of the inventive composition.

An embodiment of the inventive composition, the IC prepared in Example 1, was used in the in vitro experiment.

1) Mouse Skin Cell Culture

Mouse skin cells were harvested from fresh skin of mice immediately after sacrifice and cultured in MEM in 6-well culture plates (about $10^4$ cells/ml, 7 ml/well). After three days, the cells appeared to grow normally and adhered to the substrate of the cell culture plates at the $8^{th}$ day of culture. About 3 g of the inventive composition was added to the treatment group and 2 ml of MEM was added to the control group. Growth media in the cultures in both groups were changed every 4~5 days and microscopic appearance of cultures was recorded every 2~3 days.

FIGS. 15A-D show the results of the in vitro experiments on mouse skin cell culture in the presence and absence of the inventive composition. Pictures of the right column were obtained from the control group and those of the left column from the treatment group. On day 10 cells in both groups appeared to grow healthily (FIG. 15A). However, there was a dramatic change in cell survival and growth in the two groups. In the control group, cells started to die on day 30 whereas cells in the treatment group survived and retained normal morphology (FIG. 15B). On day 49 there was more cell death in the control group whereas the cells in the treatment continued to proliferate actively (FIG. 15C). On day 70 cells in the control group all died. In sharp contrast, cells in the treatment group still grew strongly and almost reached confluency (FIG. 15D). During the observation period of 6 months, cells in the treatment group still kept proliferation without showing abnormal morphology.

These results show that the inventive composition is capable of promoting the growth of primary cell, presumably by transforming primary skin cells into epidermal stem cells with a potential of continual proliferation. This is consistent with the effects on adult cells in human treated with the inventive composition.

2) Rat Hair Follicle Stem Cell Culture

Rat hair follicle stem cells were obtained from the bulge of hair follicles in the rats immediately after sacrifice and cultured in MEM in culture plates and cultured in MEM/5% FCS in 24-well culture plates (about 2 ml/well). After 5 days, the cells appeared to grow normally and adhered to the substrate of the cell culture plates. About 1 g of the inventive composition was added to the treatment group and 1 ml of MEM was added to the control group. The cultures were observed for 41 days and microscopic appearance of cultures was recorded.

FIGS. 16A-C show the results of the in vitro experiments on rat hair follicle stem cell culture in the presence and absence of the inventive composition. Pictures of the right column were obtained from the control group and those of the left column from the treatment group. As shown in pictures in the right column of FIG. 16, the stem cells in the control group survived but grew as individual cells. In contrast, stem cells in the treatment group proliferated and started to adhere to each other and form clones (left column of FIG. 16). On day 41 there were many clones formed in the treatment group, manifesting a tissue-like morphology, whereas the cells in the control group, although proliferative, remained scattered without forming any clone.

These results demonstrate that the inventive composition is capable of promoting not only proliferation but also tissue-specific adhesion of stem cells. This is also consistent with the effects on adult cells in human treated with the inventive composition.

3) Mouse Skin Tissue Culture

Mouse skin were obtained from fresh skin of mice immediately after sacrifice, cut into small pieces and cultured in MEM in culture plates and cultured in MEM/15% FCS in 6-well culture plates (5 ml/well containing 3 skin pieces). After 4 days, the skin pieces adhered to the substrate of the cell culture plates. About 6 g of the inventive composition was added to the treatment group and 6 ml of MEM was added to the control group. The cultures were observed for 44 days and microscopic appearance of cultures was recorded.

FIGS. 17A-C show the results of the in vitro experiments on mouse skin tissue culture in the presence and absence of the inventive composition. Pictures of the right column were obtained from the control group and those of the left column from the treatment group. As shown in pictures in the right column of FIG. 17, there was migration and scattering of cells in the control group. In contrast, there was little migration and scattering of cells in the treatment group and the newly generated cells remained adhered to the skin pieces (left column of FIG. 16). On day 44 cells in the treatment group continued to proliferate and integrated into the skin pieces which showed clear margins under microscope. In contrast, the cells continued to dislodge from the skin pieces and scattered in the culture.

These results demonstrate that the inventive composition is capable of promoting adhesion of cells to its cognate tissue and maintaining the integrity of a normal skin structure. This is also consistent with the effects on adult cells in human treated with the inventive composition.

Example 3

Treatment of Diabetic Skin Ulcer with the IC

Eight patients (three males and 5 females, age 40–68 yr) suffering from type II-diabetic skin ulcer were treated with the IC. Most of the patients had surface ulcer in the lower limb with ulcer areas ranging from 1% to 3% of the body surface area. The depths of ulcer in these patients either reached the dermis, hypodermis, or the muscle layer. Necrotic tissues were surgically debrided with scissors while avoiding injury to the viable tissue surrounding the ulceric area. The IC was applied topically to the ulceric area 3–5 times a day in a sufficient amount to cover the area at about 1 mm thickness. Four patients with smaller ulceric areas healed within 1 week of the treatment; two patients with deep ulcer (which caused exposure of the tendon ligaments)

healed within 2 weeks of treatment; one patient with a large surface ulcer in the buttocks (about 2% of the body surface area) healed within 3 weeks of treatment; and one patient with a large surface ulcer in the left lower limb (about 3% of the body surface area) healed within 4 weeks of treatment.

Example 4

Treatment of Radiation Skin Ulcer with the IC

Twenty-six patients (17 males and 9 females, age 3 mon-56 yr) suffering from skin ulcer after radiation treatment of tumors or cancer. The area of the ulcers ranged from 3×2 cm$^2$ to 13×4 cm$^2$. The IC was applied topically to the ulceric area every 1–2 days in a sufficient amount to cover the area at about 4 mm thickness. Prior to replacement with fresh IC necrotic tissues in the ulceric area were removed with sterile gauze while avoiding injury to the viable tissue the surrounding area. The ulceric area covered by the IC was dressed with sterile bandages. All of the 26 patients healed within 10–75 days of the treatment.

Example 5

Treatment of Lower Limb Terminal Vein Ulcer with the IC

Nineteen patients (13 males and 6 females, age 31–80 yr) suffering from terminal vein ulcer in the lower limbs were treated with the IC. The size of the ulcers ranged from 2 cm to 10 cm. The IC was applied topically to the ulceric area 1–2 times a day in a sufficient amount to cover the area at about 2–3 mm thickness. Prior to replacement with fresh IC necrotic tissues in the ulceric area were removed with tweezers while avoiding injury to the viable tissue the surrounding area. The leg with ulcer covered by the IC was bound by sterile bandages covered with surgical dressing. All of the 19 patients healed withing 16–113 days of the treatment.

Example 6

Induction and Propagation of Epidermal Stem Cells In Vivo and In Situ

The following example demonstrates for the first time that embryonic epidermal stem cells are induced or activated and able to proliferate in adult human under conditions favorable for physiological tissue repair and organ regeneration. Such regenerative conditions are provided by applying the methodology and compositions disclosed in the present invention. Further, dynamic changes in the level of these embryonic epidermal stem cells were detected in the skin undergoing skin regeneration in response to the treatment using the methodology and the composition.

During the treatment of an adult who suffered a superficial third degree burn, regenerative stem cells needed for regenerating various skin tissues were activated under the optimal condition provided by the inventive composition. Among these regenerative cells, embryonic epidermal stem cells expressing the marker keratin-19, i.e., K-19 keratinocytes, were specifically detected by using immunohistochemical and immunofluorescence techniques. Dynamic changes in the level of K-19 expressing regenerative cells were also monitored at different time points during the period of skin regeneration of this patient.

A 20 years-old female sustained a gasoline burn in her limbs (FIG. 18) with 35% total burn surface area (TBSA). Pathological analysis revealed 15% deep partial-thickness burn and 20% superficial full-thickness burn. Microscopic examination of sections of the tissues from the burn wounds revealed full-thickness necrosis of skin cells, degeneration and structural disturbance of collagenous fibers in dermis and microcirculation stasis (FIG. 19).

Skin and tissue of the injured areas were taken from the patient at 24 hour and on days 4, 7, 14, 21 and 28 post burn and were preserved in tubes frozen with liquid nitrogen and then were embedded in Tissue-Tek OCT Compound and frozen with liquid nitrogen. Sections of a thickness of 10 µm, were made in a thermostatic freezing chamber.

Indirect immunofluorescence staining was performed on the sections using a biotin-avidin DCS system. The frozen sections were incubated with 10% horse serum at 4° C. for 20 min, then a diluted (1:20) solution of mouse anti-human keratin type 19 monoclone antibody (the $1^{st}$ antibody) was added in. The sections were incubated again at 4° C. overnight. After washing with phosphate buffer solution, 5 µg/ml of biotinized horse anti-mouse IgG antibody, (the $2^{nd}$ antibody) (Vector Laboratories Burlingame, Calif., USA) was added to the sections, which were then incubated at 4° C. for one hour. After washing again with phosphate buffer solution, 10 µg/ml of biotin-avidin DCS (Vector Laboratories Burlingame, Calif., USA) was added to the sections, which were incubated at 4° C. for one hour. The sections were washed and mounted in glycerin containing 10% PBS and 1% para-phenylenediamine. Sections of normal skin as controls were stained in the same way, but no $1^{st}$ antibody was added. The specimens were observed under Olympus reflecting fluorescence microscope and photos were taken using ASA400 KODAK films.

In this example, the immunohistochemical examinations of normal and burned skins were performed by treating with specific mouse anti-human keratin type 19 monoclone antibody. The results revealed that in the normal epidermis of this patient, few cells were K-19 positive (FIG. 20A).

In contrast, for skin in the wounds, there was a moderate amount of regenerative epidermal stem cells which were stained positive for K-19 24 hr post burn (FIG. 20B). On day 4 post burn, the number of regenerative epidermal stem cells increased around the sweat gland, capillaries and follicles (FIG. 20C). Microscopic examination of the sections of skin undergoing regeneration revealed that there was active proliferation of nascent epithelial tissues, collagenous fibers and the skin embryonic base (EB) (FIGS. 21 and 22).

On days 7 (FIG. 20D) and 14 (FIG. 20E) epidermal stem cells continued to increase, reaching a peak value during this period. Until day 21 (FIG. 20F) and day 28, the number of regenerative stem cells decreased to a low level.

On day 20 post burn, microscopic examination of the sections taken from the healing wound site revealed that hemidesmosome junction formed between epithelial cells and the basement membrane (FIG. 29). Further, desmosome junctions also formed between echinocytes (FIG. 28).

On day 30 post burn, electron microscopic examination of the sections taken from the new skin of the patient revealed that the skin regenerated by using the methodology of the present invention retains its normal, physiological structure (FIG. 24). Also, the collagenous fibers in the regenerated new skin were normal in both size and spatial arrangement, measured 0.1–05 µm and with characteristic light and dark periodic cross striation (64 nm) (FIG. 26). Argentaffin staining of the section showed that after the treatment with the inventive method and composition for 30 days, the basal membrane in basal lamina of epidermis was actively regenerative (FIG. 25).

To confirm that the skin was regenerated from the patient's own body not from exogenous sources, immunohistochemical staining was performed on sections taken from the regenerated skin of this patient 30 days post burn. Immunohistochemical analysis of the section stained with $AE_3$ revealed positive protein of squamous epithelium, indicating spontaneous self-regeneration of the skin (FIG. 27A). Consistently, the section stained with $AE_1$ showed negative protein of glandular epithelium (FIG. 27B). These results demonstrated for the first time that a new human organ can be regenerated in vivo and in situ with normal, physiological structures and functions at both cellular and tissue levels (FIG. 23).

In burn wounds of deep second degree (deep partial-thickness burn) or worse, epidermal stem cells residing in the basal layer of epidermis are destroyed. More interestingly and challengingly, in burn wounds of superfacial third degree (full-thickness burn), the whole epidermis and dermis are destroyed with only hypodermis, the fatty layer of the skin, remaining viable. Treatment of full-thickness burn with conventional methods such as dry therapy and skin grafts results in wound-closure with disfiguring scars and substantial loss of normal functions of appendages of the skin. However, as shown above, an adult sustained both deep second degree and third degree burn could recover with skin regenerated without substantial loss of its structures and functions. What is the source(s) of cells that compose to form the tissues which constitute the regenerated organ?

The present invention provides the answer herein by demonstrating clinically that at least part, if not all, of the epidermal cells are originated from regenerative epidermal stem cells. As shown in FIGS. 20B–G, these stem cells were stained positive for K-19 while the body underwent active tissue repair and skin regeneration. These regenerative epidermal stem cells proliferated and differentiated to produce specific types of keratinocytes capable of synthesizing other types of keratin, e.g., keratin type 9 and 16, which moved upward towards the epidermis. These differentiated cells continued to move upward and further differentiated to produce keratinocytes capable of synthesizing harder keratin (e.g., keratin type 1 and 10), which is the typical keratin of mature epidermal cells.

However, it should be noted that only the regenerative epidermal stem cells were labeled here by using K-19 as a detectable marker. Regenerative stem cells for other tissues, such as blood vessels, hair follicles, collagenous fiber, interstitium and nerves, were also activated, proliferate, and differentiate to produce all cells needed for regeneration of a fully functional organ in vivo and in situ (FIGS. 6 and 11).

The next question to be answered is: "where did the regenerative cells come from?" Under normal physiological conditions, some cells long stay at phase $G_o$ or $G_1$ of the cell cycle and their proliferation starts only when the condition becomes favorable. However, some cells proliferate continuously through out the body's life, thus demanding a continuous supply of stem cells. Part of the daughter-cells of stem cells differentiate to become mature, specialized cells and part of them keep their proliferation ability. For an intact, normal skin, stem cells in the basal layer of epidermis are capable of proliferating continuously. Newly proliferated cells move upward towards the epidermis. When reaching the deep area of the spinous layer, they proliferate again two or three times and then lose their proliferation ability.

As discussed above, in deep second and third degree burn wounds, epidermis and dermis deep layers are injured, and stem cells in the basal layer of epidermis are destroyed. Based on the observation of the wound healing process at both the cellular and the tissue levels, the inventor believes that the residual surviving mesenchymal cells around the follicles, sweat glands and capillaries in subdermal tissue (FIG. 31) may provide most, if not all, of the regenerative stem cells, including the multipotent epidermal stem cells. The mesenchymal cells in the remaining viable tissues are activated and converted to adult stem cells (ASCs) in response to injury of the body and/or by the stimulation of the active ingredients in the inventive composition. These ASCs are multipotent, and under the regenerative conditions provided by the inventive composition can be induced to differentiate directionally into various tissue stem cells for tissues, such as dermis, epidermis, blood vessels, hair follicles, collagenous fiber, interstitium and nerves. These specialized tissue stem cells are cultivated under the regenerative conditions provided by the inventive composition to produce daughter stem cells, part of which are induced to differentiate tissue-specifically into various cells needed for regeneration of a fully functional organ in vivo and in situ.

For example, epidermal stem cells that supply various types of keratinocytes may be originated from the mesenchymal cells. In response to injury and under the regenerative conditions provided by the inventive composition the mesenchymal cells in the residual viable tissues at the injured site are converted to ASCs, part of which then directionally differentiate into regenerative epidermal stem cells. Such epidermal stem cells can synthesize specific cellular keratin type 19, therefore can be identified by immunocytochemical method. Here, by using anti-human keratin type 19 monoclone antibody regenerative epidermal stem cells were specifically detected in the hypodermal tissue in deep second and superficial third degree burn wounds.

As shown above, after treated with the methodology of the present invention, the number of K-19 expressing regenerative stem cells increased as the wound healing progressed, reached a peak value and then declined when almost all of the tissues were regenerated. These results show that even for a third degree burn which causes complete destruction of the epidermis and dermis, regenerative epidermal stem cells can still be activated or induced from the residual viable tissues under the conditions provided by using the methodology of the present invention.

With administration of the inventive composition to the wound and proper clinical management, the regenerative stem cells of the body were activated and proliferate to ensure the spontaneous, physiological regeneration of healthy skin without scars for deep second degree burns, and with only smooth and soft scars for superficial third degree burns.

The above results indicate that embryonic epidermal stem cells (K-19 keratinocytes) were induced or activated in response to burn wounds and able to proliferate under the regenerative conditions provided by the inventive composition. The amount of these stem cells changed dynamically in the course of skin regeneration, revealing for the first time in vivo and in situ how an adult body conducted self-tissue repair and organ regeneration through activation and proliferation of its own stem cells under favorable conditions provided exogenously. These regenerative stem cells are believed to provide the source of epidermal cells, if not all, needed for regenerating skin.

Further, based on clinical observation at the tissue and cellular levels, the inventor believes that after the tissue stem cells are produced from the ASCs, the tissue stem cells of a specific tissue type (e.g. an epidermal stem cell) are induced to produce various types of cells needed for regenerating their cognate tissue (e.g., keratinocytes of various types such as K-1, -9, -10 and -16). These cells communicate with each other by forming junctions specific and characteristic for their cognate tissue (e.g., the desmosome junctions between two echinocytes as shown in FIG. 28), which results in the regeneration of the nascent tissue. The regenerated nascent tissues are cultivated under the favorable conditions provided by the inventive composition and communicate with each other by forming junctions specific and characteristic for their cognate organ, such as the hemidesmosome injunction between epithelial cells and the basement membrane as showed in FIG. 29. Further, these nascent tissues are assembled organ-specifically to constitute a nascent organ. Finally the tissues in the nascent organ mature into their corresponding adult tissues which constitute the regenerated, fully functional organ. Through these cell-cell, cell-tissue and tissue-tissue communications within a live body, tissues and organs can be regenerated with restoration of their physiological structures and functions. For example, as demonstrated above, an adult who lost the epidermis and dermis in a significantly large area of her body can recover with new skin that is normal in both structure and function (FIGS. 23 and 24).

These discoveries and inventions are significant theoretically and practically. First, they reveal for the first time that adult tissues and organs can be repaired and regenerated with restoration of full physiological functions through cultivation of stem cells in vivo and in situ. This outcome has been dreamed by scientists and physicians in the art but never achieved clinically. The inventor believes that although transplantation of stem cells cultivated in vitro has enjoyed limited successes in repairing damaged epidermis and dermis, the healing of the wounds is not physiological. In other words, the skin repaired by using the transplantation method sustains disfiguring scars and loss of physiological functions of the appendages such as hair follicles, apocrine and eccrine sweat glands. Microscopically, only in the present invention is demonstrated that junctions between cells in the same tissue and between neighboring tissues (e.g., between epidermis and dermis) are restored structurally and functionally to the full physiological extent. By contrast, junctions between tissues repaired by using other methods in the art are reconstructed pathologically, manifesting abnormal structures and functions.

Second, it is for the first time that multipotent embryonic stem cells are induced or activated in a fully developed human body during its self-tissue repair and organ regeneration. As shown above, a large number of regenerative stem cells on the wounds expressed K-19 during the physiological wound healing process directed by using the methodology of the present invention. It has been well acknowledged that keratin 19 is expressed in the basal cell layer of fetal epidermis and in the bulge of the developing hair of human fetuses. Thus the cultivation of these embryonic stem cells in vivo and in situ for adult tissue repair and organ regeneration is not only innovative in medicine but also has a profound impact on developmental and cell biology.

What is claimed is:

1. A method for regenerating skin with normal physiological structure at a wound site of the skin in a mammal comprising:
  administering in vivo to said mammal at the site of the wound a composition comprising
  beeswax at a concentration of 1%–20% by weight and a fatty acid-containing oil at a concentration of at least 10% by weight based on the total weight of the composition; and a sterol compound added to and dissolved in said oil at a concentration of at least 1% by weight based on the total weight of the composition, such that keratin-19 expressing keratinocytes are activated at the wound site to regenerate the skin with normal physiological structure.

2. The method according to claim 1, wherein the wound is an acute wound resulted from physical trauma, thermal, wind, frost, optical or electric injury.

3. The method according to claim 1, further comprising:
  liquefying a necrotic tissue of the wound; and
  removing the liquefied necrotic tissues from the wound site without surgical debridement.

4. The method according to claim 1, wherein the wound is a chronic wound.

5. The method according to claim 4, wherein the chronic wound is selected from the group consisting of chronic surface ulcer, diabetic ulcer, decubital ulcer, chronic wound as a result of a lower limb vascular disease, chronic wound as a result of poor blood flow, wound due to cancer or cancer metastasis, erosion caused by bacterial or viral infection, herpes simplex corneal ulcer, subcutaneous tissue ulcer, radiation-caused skin ulcer, vaginitis, cervical erosion, gingivitis, wounds due to dilation and enlargement of veins, and hemorrhoid.

6. The method according to claim 4, further comprising:
  debriding the chronic wound before administering the composition to the wound.

7. The method according to claim 6, wherein debriding the wound includes surgically removing necrotic tissues from the wound.

8. The method according to claim 6, wherein debriding the wound includes chemically removing necrotic tissues from the wound.

9. The method according to claim 1, wherein the mammal is human and the composition is administered topically to the wound.

10. The method according to claim 1, wherein the mammal is human and the composition is administered to the wound at least three times a day.

11. The method according to claim 1, wherein the composition is administered in a sufficient amount to the wound such that the wound site is maintained moist.

12. The method according to claim 1, wherein the composition is in a form of ointment and is administered in a sufficient amount to cover the wound at a thickness of 0.5–5 mm of the ointment.

13. The method according to claim 1, wherein the composition is in a form of ointment and is administered in a sufficient amount to cover the wound at a thickness of 1–3 mm of the ointment.

14. The method according to claim 1, wherein the sterol compound is esterified by the fatty acid in the oil in the composition.

15. The method according to claim 1, wherein a fatty acid-containing oil is at a concentration at least 50% by weight based on the total weight of the composition.

16. The method according to claim 1, wherein a fatty acid-containing oil is at a concentration at least 80% by weight based on the total weight of the composition.

17. The method according to claim 1, wherein the concentration of the sterol compound is about 1.2–40% by weight.

18. The method according to claim 1, wherein the concentration of the sterol compound is about 1.2–20% by weight.

19. The method according to claim 1, wherein the concentration of the sterol compound is about 1.5–15% by weight.

20. The method according to claim 1, wherein the concentration of the sterol compound is about 2–6% by weight.

21. The method according to claim 1, wherein the beeswax in the composition forms a pigeon-hole like structure at ambient temperature or below.

22. The method according to claim 1, wherein the dimension of at least one of the holes in the pigeon-hole like structure is below 50 micron.

23. The method according to claim 1, wherein the dimension of at least one of the holes in the pigeon-hole like structure is below 20 micron.

24. The method according to claim 1, wherein the dimension of at least one of the holes in the pigeon-hole like structure is between 10–50 micron.

25. The method according to claim 1, wherein the composition further comprises baicalin.

26. The method according to claim 25, wherein the composition further comprises an extract of huangqin in an amount of 10–90% by weight based on the total weight of the composition, wherein the amount of huangqin is 2–60% by weight based on the total weight of the oil.

27. The method according to claim 1, wherein the oil is animal or vegetable oil.

28. The method according to claim 1, wherein the oil is vegetable oil selected from the group consisting of corn oil, peanut oil, cottonseed oil, rice bran oil, safflower oil, tea tree oil, pine nut oil, macadamia nut oil, camellia seed oil, rose hip oil, sesame oil, olive oil, soybean oil and combinations thereof.

29. The method according to claim 1, wherein the oil is a pharmaceutically acceptable oil.

30. The method according to claim 1, wherein the oil is an injectable oil.

31. The method according to claim 1, wherein the fatty acid is selected from the group consisting of palmitic acid, linoleic acid, oleic acid, trans-oleic acid, stearic acid, arachidic acid, and tetracosanoic acid.

32. The method according to claim 1, wherein the sterol compound is animal sterol or phytosterol.

33. The method according to claim 1, wherein the sterol compound is a phytosterol selected from the group consisting of stigmasterol, campesterol, β-sitosterol, chalinosterol, clionasterol, brassicasterol, α-spinasterol, daucosterol, desmosterol, avenasterol, cycloartenol, poriferasterol, and natural or synthesized, isomeric forms and derivatives thereof.

34. The method according to claim 1, wherein the sterol compound is a combination of stigmasterol and β-sitosterol.

35. The method according to claim 1, wherein the sterol compound is a combination of brassicasterol and β-sitosterol.

36. The method according to claim 1, wherein the sterol compound is a combination of brassicasterol, stigmasterol and β-sitosterol.

37. The method according to claim 1, wherein the sterol compound is a combination of campesterol, stigmasterol and β-sitosterol.

\* \* \* \* \*